United States Patent
Ogura et al.

(10) Patent No.: US 8,022,072 B2
(45) Date of Patent: Sep. 20, 2011

(54) AZOLYLMETHYLIDENEHYDRAZINE DERIVATIVE AND USE THEREOF

(75) Inventors: Hironobu Ogura, Kyoto (JP); Yoshiyuki Tatsumi, Kyoto (JP); Yuji Fukamizu, Kyoto (JP)

(73) Assignee: Kaken Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 12/664,834

(22) PCT Filed: Jun. 17, 2008

(86) PCT No.: PCT/JP2008/061061
§ 371 (c)(1), (2), (4) Date: Dec. 15, 2009

(87) PCT Pub. No.: WO2008/156092
PCT Pub. Date: Dec. 24, 2008

(65) Prior Publication Data
US 2010/0190754 A1     Jul. 29, 2010

(30) Foreign Application Priority Data
Jun. 18, 2007   (JP) .................................. 2007-160777

(51) Int. Cl.
*A61K 31/4025* (2006.01)
*C07D 233/64* (2006.01)
*C07D 409/02* (2006.01)
*C07D 409/06* (2006.01)

(52) U.S. Cl. .............. 514/237.2; 514/397; 514/399; 540/603; 544/139; 544/370; 546/210; 548/312.1; 548/312.7; 548/314.7; 548/336.1

(58) Field of Classification Search .......... None
See application file for complete search history.

(56) References Cited

U.S. PATENT DOCUMENTS

| 4,351,948 A | 9/1982 | Fellner et al. | |
| 4,623,655 A * | 11/1986 | Gayer et al. | .............. 514/399 |

FOREIGN PATENT DOCUMENTS

| JP | 56-150069 A | 11/1981 |
| JP | 63-223650 A | 9/1988 |
| JP | 63-227586 A | 9/1988 |
| JP | 06-161136 A | 6/1994 |
| WO | WO 2004/099371 A2 | 11/2004 |

OTHER PUBLICATIONS

Roberts et al., "Guidelines for Treatment of Onychomycosis'", British Journal of Dermatology, 148, 402-410, 2003.*
Furue et al., *Dermatologic Therapy*, 19(2): 118-126 (2006).
Sayanna et al., *Heterocycles*, 23(9): 2183-2186 (1985).
Tatsumi et al., *Antimicrobial Agents and Chemotherapy*, 46(12): 3797-3801 (Dec. 2002).

* cited by examiner

*Primary Examiner* — Fiona T Powers
(74) *Attorney, Agent, or Firm* — Leydig, Voit & Mayer, Ltd.

(57) ABSTRACT

An azolylmethylidenehydrazine derivative represented by the formula (I)

$$\begin{array}{c} R^1 \\ \diagdown \\ N-N=C \\ \diagup \quad\quad\quad \diagdown \\ R^2 \quad\quad\quad N-X \\ \quad\quad\quad\quad \diagdown\diagup \\ \quad\quad\quad\quad N \end{array} \quad\quad Ar \quad\quad (I)$$

wherein Ar is an aryl group optionally having substituent(s) or a heteroaryl group optionally having substituent(s), $R^1$ and $R^2$ are the same or different and each is an alkyl group, a cycloalkyl group, an aralkyl group optionally having substituent(s), an aryl group optionally having substituent(s), a heteroarylalkyl group optionally having substituent(s), or $R^1$ and $R^2$ are bonded to each other to form a nitrogen-containing heterocyclic group optionally having substituent(s), and X is CH or a nitrogen atom, or a pharmacologically acceptable salt thereof is useful as a medicament, particularly as an antifungal agent, or an anti-inflammatory agent or an antiallergic agent.

20 Claims, No Drawings

AZOLYLMETHYLIDENEHYDRAZINE DERIVATIVE AND USE THEREOF

TECHNICAL FIELD

The present invention relates to an azolylmethylidenehydrazine derivative or a salt thereof, and a medicament containing same as an active ingredient.

BACKGROUND ART

Generally, antifungal agents are used for the treatment of superficial mycosis (trichophytosis, tinea versicolor, cutaneous candidiasis etc.). In recent years, therapeutic agents for tinea pedis such as luliconazole, amorolfine, lanoconazole and the like, which have a superior anti-*Trichophyton* activity, and therapeutic agents for tinea unguium such as terbinafine and itraconazole have been clinically applied. Nevertheless, the number of patients has not decreased, and the number of domestic patients with tinea pedis is estimated to be 25 million and that of domestic patients with tinea unguium is estimated to be 12 million.

Normally, the treatment of tinea pedis takes 4 weeks. However, the necessity of 4-month topical treatment for complete cure has been reported. When subjective symptoms such as flare, itch and the like disappear, patients cease treatment on self-judgment, which permits fungi present in the affected part to grow and often cause recurrence or relapse. Furthermore, reinfection with *Trichophyton* unleashed by family or patients themselves is considered to also prevent the number of tinea pedis patients from decreasing. Therefore, the development of an external antifungal agent which completely cures tinea pedis by application for a short period of time and causes less relapse has been desired.

Among the superficial mycosis, tinea unguium is particularly intractable, and commercially available external antifungal agents are not expected to penetrate thick nail plates. Therefore, oral antifungal agents such as terbinafine, itraconazole and the like are generally used for the treatment. Since the treatment requires oral administration of the medicament for at least 3 months, medication compliance of the patients is low. Moreover, while many of the tinea unguium patients are persons of middle or advanced age or elderly persons, patients with pre-existing disease such as diabetes and the like often interrupt or cease treatment due to side effects of oral preparation (e.g., hepatopathy, gastrointestinal disorder and the like) or drug interaction. These make it difficult to completely cure tinea unguium and cause many incidents of recurrence. Hence, an antifungal agent highly effective against tinea unguium by topical application free from systemic side effects and drug interaction is demanded in clinical practice.

Since *Trichophyton* parasitizes in the keratinous tissues of stratum corneum layer, nail and hair, for an antifungal agent to exhibit a superior treatment effect, (1) superior anti-*Trichophyton* activity, (2) good penetrability and accumulability in stratum corneum, and (3) less decrease in the activity due to adsorption to keratin, a keratinous component, are required. Many of the commercially available superficial mycosis therapeutic agents are superior in the anti-*Trichophyton* activity and penetrability and accumulability in the stratum corneum, but show high adsorbability to keratin, as a result of which the activity decreases in the stratum corneum layer (see, for example, non-patent document 3). This is considered to be one of the reasons why a treatment by application of commercially available antifungal agents cannot cure tinea pedis or tinea unguium in a short time.

Inflammation, inflammation causing allergic disease and allergic reaction are generally divided into type I to type IV. In type I, inflammation and allergic reaction mainly in mastocytes are induced, as observed in allergic rhinitis, urticaria, pruritus and the like. Such immediate phase inflammation and allergic reaction are induced by chemical mediators such as histamine, leukotriene and the like, which are released from mastocytes, and anti-histamine drugs and chemical mediator-free suppressants and the like show treatment effects. In the late phase reaction following the immediate phase, intradermal infiltration of many eosinophils to occur to further aggravate inflammation. While type IV reaction is seen in diseases such as atopic dermatitis, contact dermatitis, psoriasis and the like, the treatment effects of anti-histamine drugs and chemical mediator-free suppressants are limited, and therefore, steroids are used as main therapeutic drugs. In addition, immunosuppressants such as cyclosporine, tacrolimus and the like show treatment effects against these diseases. However, those medicaments show various side effects. Steroids cause side effects such as infections, skin atrophy, diabetes and the like. Tacrolimus causes side effects such as severe skin irritation and the like in atopic dermatitis patients (see, for example, non-patent document 1). In consideration of the above, the development of a safer anti-inflammatory agent or antiallergic agent for inflammation and allergic reactions of type I, type IV and the like has been desired.

While compounds having an azolyl group such as triazolyl group, imidazolyl group and the like and a hydrazone structure in a molecule have been reported (see, for example, non-patent document 2 and patent documents 1 to 3), they have different structures of $-N(R^1)(R^2)$ in the formula (I) from that of the present invention. Moreover, usefulness as an antifungal agent, anti-inflammatory agent or antiallergic agent is not described.

[patent document 1] JP-A-63-227586
[patent document 2] JP-A-6-161136
[patent document 3] WO 2004099371
[non-patent document 1] Dermatologic Therapy, 19(2), 118-126, 2006
[non-patent document 2] Heterocycles, 23(9), 2183-2186, 1985
[non-patent document 3] Antimicrobial Agents and Chemotherapy, 46(12), 3797-3801, 2002

DISCLOSURE OF THE INVENTION

Problems to be Solved by the Invention

Accordingly, it is one of the objects of the present invention to provide a compound highly effective for tinea pedis, tinea unguium and the like based on a superior antifungal activity against *Trichophyton*, *Candida* and *Malassezia*, which are pathogenic fungi of superficial mycosis.

Another object of the present invention is to provide a compound having a superior treatment effect on various inflammations and allergic diseases.

Means of Solving the Problems

The present inventors have synthesized a number of azolylmethylidenehydrazine derivatives and salts thereof and conducted intensive studies of antifungal activity thereof. As a result, they have found that a novel azolylmethylidenehydrazine derivative represented by the formula (I) or a salt thereof shows a superior antifungal activity against various pathogenic fungi of superficial mycosis, which resulted in the completion of the first embodiment of the present invention.

Furthermore, the present inventors have conducted intensive studies of anti-inflammatory and antiallergic actions and found that the derivative shows a superior therapeutic effect on various inflammations and allergic diseases, which resulted in the completion of the second embodiment of the present invention.

Accordingly, the present invention provides the following.

[1] An azolylmethylidenehydrazine derivative represented by the formula (I)

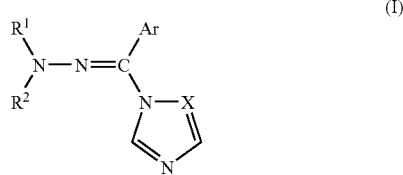

wherein Ar is an aryl group optionally having 1 to 5 substituents selected from substituent group A or a heteroaryl group optionally having 1 to 5 substituents selected from substituent group A, $R^1$ and $R^2$ are the same or different and each is a C1-8 alkyl group, a C3-8 cycloalkyl group, a C7-15 aralkyl group optionally having 1 to 5 substituents selected from substituent group A, an aryl group optionally having 1 to 5 substituents selected from substituent group A, a heteroarylalkyl group optionally having 1 to 5 substituents selected from substituent group A, or $R^1$ and $R^2$ are bonded to each other to form a nitrogen-containing heterocyclic group optionally having 1 to 5 substituents selected from substituent group A, X is CH or a nitrogen atom, substituent group A is a C1-8 alkyl group optionally having 1 to 5 substituents selected from substituent group B, a C2-8 alkenyl group optionally having 1 to 5 substituents selected from substituent group B, a C3-8 cycloalkyl group, a C7-15 aralkyl group optionally having 1 to 5 substituents selected from substituent group B, a C1-8 alkoxy group optionally having 1 to 5 substituents selected from substituent group B, a C1-8 alkylthio group optionally having 1 to 5 substituents selected from substituent group B, an amino group, a mono- or di-(C1-8 alkyl)amino group optionally having 1 to 5 substituents selected from substituent group B (two alkyls may be the same or different), a C1-8 alkylsulfinyl group optionally having 1 to 5 substituents selected from substituent group B, a C1-8 alkylsulfonyl group optionally having 1 to 5 substituents selected from substituent group B, a C1-8 alkylsulfonylamino group, an acyl group, an acyloxy group, an acylamino group, a C1-8 alkoxycarbonyl group, a halogen atom, a hydroxyl group, a carboxyl group, a nitro group, a cyano group, an aryl group optionally having 1 to 5 substituents selected from substituent group B, an aryloxy group optionally having 1 to 5 substituents selected from substituent group B, a heteroaryloxy group, an arylthio group, a C7-15 aralkyloxy group optionally having 1 to 5 substituents selected from substituent group B, a C2-8 alkenyloxy group optionally having 1 to 5 substituents selected from substituent group B, a C2-8 alkynyloxy group optionally having 1 to 5 substituents selected from substituent group B, a heterocyclylalkyl group optionally having 1 to 5 substituents selected from substituent group B or a heterocyclylalkyloxy group optionally having 1 to 5 substituents selected from substituent group B, substituent group B is a C1-8 alkyl group optionally having 1 to 5 substituents selected from substituent group C, a C1-8 alkoxy group optionally having 1 to 5 substituents selected from substituent group C, an amino group, a mono- or di-(C1-8 alkyl)amino group (two alkyls may be the same or different), an acyloxy group, an acylamino group, a halogen atom, a cyano group, an aryl group optionally having 1 to 5 substituents selected from substituent group C, an aryloxy group optionally having 1 to 5 substituents selected from substituent group C, a C7-15 aralkyloxy group, an arylthio group or a heteroaryloxy group, and substituent group C is a halogen atom, a C1-8 alkyl group or a C1-8 alkoxy group, or a pharmacologically acceptable salt thereof.

[2] The azolylmethylidenehydrazine derivative according to the above-mentioned [1], wherein Ar is a phenyl group optionally having 1 to 5 substituents selected from substituent group A, and $R^1$ and $R^2$ are methyl groups, or a pharmacologically acceptable salt thereof.

[3] The azolylmethylidenehydrazine derivative according to the above-mentioned [1] or [2], wherein Ar is 2-ethylphenyl group, 2-ethoxyphenyl group, 2-propoxyphenyl group, 2-isopropoxyphenyl group, 2-butoxyphenyl group, 2-allyloxyphenyl group, 2-(2-phenoxyethoxy)phenyl group, 2-trifluoromethoxyphenyl group, 2-propynyloxyphenyl group, 2-methylthiophenyl group, 2-ethylthiophenyl group, 2-propylthiophenyl group, 2-butylthiophenyl group, 2-phenethylthiophenyl group, 2-(4-methoxybenzyloxy)phenyl group, 2-(4-fluorophenethyloxy)phenyl group, 2-(4-dimethylaminophenethyloxy)phenyl group, 2-[2-(4-methoxyphenoxy)ethoxy]phenyl group or 2-(3-phenoxypropoxy)phenyl group, or a pharmacologically acceptable salt thereof.

[4] The azolylmethylidenehydrazine derivative according to any of the above-mentioned [1] to [3], which is selected from N'-[1-(2-ethylphenyl)-1-imidazol-1-ylmethylidene]-N,N-dimethylhydrazine, N'-[1-(2-ethoxyphenyl)-1-imidazol-1-ylmethylidene]-N,N-dimethylhydrazine, N'-[1-imidazol-1-yl-1-(2-propoxyphenyl)methylidene]-N,N-dimethylhydrazine, N'-[1-imidazol-1-yl-1-(2-isopropoxyphenyl)methylidene]-N,N-dimethylhydrazine, N'-[1-(2-butoxyphenyl)-1-imidazol-1-ylmethylidene]-N,N-dimethylhydrazine, N'-[1-(2-allyloxyphenyl)-1-imidazol-1-ylmethylidene]-N,N-dimethylhydrazine, N'-[1-imidazol-1-yl-1-[2-(2-phenoxyethoxy)phenyl]methylidene]-N,N-dimethylhydrazine, N'-[1-imidazol-1-yl-1-(2-trifluoromethoxyphenyl)methylidene]-N,N-dimethylhydrazine, N'-[1-imidazol-1-yl-1-(2-methylthiophenyl)methylidene]-N,N-dimethylhydrazine, N'-[1-(2-ethylthiophenyl)-1-imidazol-1-ylmethylidene]-N,N-dimethylhydrazine, N'-[1-imidazol-1-yl-1-(2-propylthiophenyl)methylidene]-N,N-dimethylhydrazine, N'-[1-(2-butylthiophenyl)-1-imidazol-1-ylmethylidene]-N,N-dimethylhydrazine, N'-[1-imidazol-1-yl-1-(2-phenethylthiophenyl)methylidene]-N,N-dimethylhydrazine, N'-[1-imidazol-1-yl-1-[2-(4-methoxybenzyloxy)phenyl]methylidene]-N,N-dimethylhydrazine, N'-[1-[2-[2-(4-fluorophenyl)ethoxy]phenyl]-1-imidazol-1-ylmethylidene]-N,N-dimethylhydrazine, N'-[1-imidazol-1-yl-1-[2-(4-dimethylaminophenethyloxy) phenyl]methylidene]-N,N-dimethylhydrazine, N'-[1-imidazol-1-yl-1-[2-[2-(4-methoxyphenoxy)ethoxy] phenyl]methylidene]-N,N-dimethylhydrazine, and N'-[1-imidazol-1-yl-1-[2-(3-phenoxypropoxy)phenyl]methylidene]-N,N-dimethylhydrazine, or a pharmacologically acceptable salt thereof.

[5] A medicament comprising the azolylmethylidenehydrazine derivative according to any of the above-mentioned [1] to [4] or a pharmacologically acceptable salt thereof, and a pharmacologically acceptable carrier.

[6] The medicament according to the above-mentioned [5], which is an antifungal agent.

[7] The medicament according to the above-mentioned [5], which is an anti-inflammatory agent or antiallergic agent.

[8] The azolylmethylidenehydrazine derivative according to any of the above-mentioned [1] to [4] or a pharmacologically acceptable salt thereof for use as an antifungal agent.

[9] The azolylmethylidenehydrazine derivative according to any of the above-mentioned [1] to [4] or a pharmacologically acceptable salt thereof for use as an anti-inflammatory agent or an antiallergic agent.

[10] A method for the prophylaxis or treatment of mycosis, comprising administering an effective amount of the azolylmethylidenehydrazine derivative according to any of the above-mentioned [1] to [4] or a pharmacologically acceptable salt thereof to a mammal in need thereof.

[11] A method for the prophylaxis or treatment of inflammation or allergy, comprising administering an effective amount of the azolylmethylidenehydrazine derivative according to any of the above-mentioned [1] to [4] or a pharmacologically acceptable salt thereof to a mammal in need thereof.

Effect of the Invention

The azolylmethylidenehydrazine derivative of the present invention or a salt thereof shows a superior antifungal activity against pathogenic fungi of deep mycosis and superficial mycosis, and an antifungal agent containing same as an active ingredient is useful for the prophylaxis or treatment of infection with fungi in mammalian animals including human.

In addition, the azolylmethylidenehydrazine derivative of the present invention or a salt thereof is useful for the treatment of various inflammations or allergic diseases.

BEST MODE FOR CARRYING OUT THE INVENTION

The terms to be used in the present invention are explained.

Examples of the "halogen atom" include fluorine atom, chlorine atom, bromine atom and iodine atom.

Examples of the "C1-8 alkyl group" include a straight chain or branched alkyl group having a carbon number of 1 to 8, and examples thereof include methyl, ethyl, propyl, isopropyl, butyl, isobutyl, s-butyl, t-butyl, pentyl, isopentyl, neopentyl, hexyl, heptyl, octyl and the like.

Examples of the "C1-8 alkoxy group" is a straight chain or branched alkoxy group having a carbon number of 1 to 8 and examples thereof include methoxy, ethoxy, propoxy, isopropoxy, butoxy, isobutoxy, s-butoxy, t-butoxy, pentyloxy, isopentyloxy, neopentyloxy, hexyloxy, heptyloxy, octyloxy and the like.

Examples of the "C3-8 cycloalkyl group" is a cyclic alkyl group having a carbon number of 3 to 8 and examples thereof include cyclopropyl, cyclobutyl, cyclopentyl, cyclohexyl, cycloheptyl, cyclooctyl, norbornyl, bicyclo[3.3.0]octyl and the like.

Examples of the "C2-8 alkenyl group" is a straight chain or branched alkenyl group having a carbon number of 2 to 8 and examples thereof include vinyl, allyl, 1-propenyl, 1-butenyl, 2-methyl-2-propenyl, 1-pentenyl, 1-hexenyl, 1-heptenyl, 1-octenyl and the like.

Examples of the "C2-8 alkenyloxy group" is a straight chain or branched alkenyloxy group having a carbon number of 2 to 8 and examples thereof include vinyloxy, allyloxy, 1-propenyloxy, 1-butenyloxy, 2-methyl-2-propenyloxy, 1-pentenyloxy, 1-hexenyloxy, 1-heptenyloxy, 1-octenyloxy and the like.

Examples of the "C2-8 alkynyloxy group" is a straight chain or branched alkynyloxy group having a carbon number of 2 to 8 and examples thereof include ethynyloxy, 2-propynyloxy, 2-butynyloxy, 3-butynyloxy, 2-pentynyloxy, 3-pentynyloxy, 4-pentynyloxy, 4-methyl-2-pentynyloxy, 2-hexynyloxy, 2-heptynyloxy, 2-octynyloxy and the like.

Examples of the "C1-8 alkylthio group" is a straight chain or branched alkylthio group having a carbon number of 1 to 8 and examples thereof include methylthio, ethylthio, propylthio, isopropylthio, butylthio, isobutylthio, s-butylthio, t-butylthio, pentylthio, isopentylthio, neopentylthio, hexylthio, heptylthio, octylthio and the like.

Examples of the "mono- or di-(C1-8 alkyl)amino group" is an amino group mono- or di-substituted by straight chain or branched alkyl having a carbon number of 1 to 8. When di-substituted, two alkyl groups may be the same or different. Examples thereof include monomethylamino, dimethylamino, N-ethyl-N-methylamino, diethylamino, N-propyl-N-methylamino, N-isopropyl-N-methylamino, dipropylamino, N-butyl-N-methylamino, N-pentyl-N-methylamino, N-isopentyl-N-methylamino, N-neopentyl-N-methylamino, N-hexyl-N-methylamino, N-heptyl-N-methylamino, N-octyl-N-methylamino and the like.

Examples of the "C1-8 alkylsulfinyl group" is a straight chain or branched alkylsulfinyl group having a carbon number of 1 to 8 and examples thereof include methanesulfinyl, ethanesulfinyl, propanesulfinyl, 2-propanesulfinyl, butanesulfinyl, 2-butanesulfinyl, 2-methyl-2-propanesulfinyl, pentanesulfinyl, isopentanesulfinyl, neopentanesulfinyl, hexanesulfinyl, heptanesulfinyl, octanesulfinyl and the like.

Examples of the "C1-8 alkylsulfonyl group" is a straight chain or branched alkylsulfonyl group having a carbon number of 1 to 8 and examples thereof include methanesulfonyl, ethanesulfonyl, propanesulfonyl, 2-propanesulfonyl, butanesulfonyl, 2-butanesulfonyl, 2-methyl-2-propanesulfonyl, pentanesulfonyl, isopentanesulfonyl, neopentanesulfonyl, hexanesulfonyl, heptanesulfonyl, octanesulfonyl and the like.

Examples of the "C1-8 alkylsulfonylamino group" is a straight chain or branched alkylsulfonylamino group having a carbon number of 1 to 8 and examples thereof include methanesulfonylamino, ethanesulfonylamino, propanesulfonylamino, 2-propanesulfonylamino, butanesulfonylamino, 2-butanesulfonylamino, 2-methyl-2-propanesulfonylamino, pentanesulfonylamino, isopentanesulfonylamino, neopentanesulfonylamino, hexanesulfonylamino, heptanesulfonylamino, octanesulfonylamino and the like.

Examples of the "C1-8 alkoxycarbonyl group" is a straight chain or branched alkoxy-carbonyl group having a carbon number of 1 to 8 and examples thereof include methoxycarbonyl, ethoxycarbonyl, propoxycarbonyl, isopropoxycarbonyl, butoxycarbonyl, isobutoxycarbonyl, s-butoxycarbonyl, t-butoxycarbonyl, pentyloxycarbonyl, isopentyloxycarbonyl, neopentyloxycarbonyl, hexyloxycarbonyl, heptyloxycarbonyl, octyloxycarbonyl and the like.

Examples of the "aryl group" is an aromatic hydrocarbon group having a carbon number of 6 to 14 and examples thereof include phenyl, naphthyl, anthryl and the like.

The "heteroaryl group" is a 5- to 9-membered, preferably 5- or 6-membered, aromatic monocyclic group, or 8- to 14-membered, preferably 8- to 10-membered, aromatic fused cyclic group, each of which has, besides carbon atom, 1 to 4, preferably 1 or 2, hetero atoms selected from nitrogen atom, oxygen atom and sulfur atom, and examples thereof include monocyclic heteroaryl groups such as pyridyl, pyrimidyl, pyridazinyl, pyrazyl, furyl, thienyl, pyrrolyl, pyrazolyl, imidazolyl, oxazolyl, isoxazolyl, thiazolyl, triazolyl, tetrazolyl and the like, fused heteroaryl groups such as indolyl, isoindolyl, quinolizinyl, isoquinolyl, quinolyl, naphthyridyl, quinazolinyl, benzofuranyl, benzothienyl, benzothiazolyl and the like, and the like.

The "C7-15 aralkyl group" is an "aryl-alkyl group" having a total carbon number of 7 to 15, which is constituted with the aforementioned "aryl group" and "C1-8 alkyl group", and examples thereof include benzyl, phenethyl, phenylpropyl, phenylbutyl, naphthylmethyl, anthrylmethyl and the like.

The "heteroarylalkyl group" is an "heteroaryl-alkyl group" constituted with the aforementioned "heteroaryl group" and "C1-8 alkyl group", and examples thereof include pyridylmethyl, furylmethyl, thienylmethyl, thiazolylmethyl, imidazolylmethyl, benzothienylmethyl, pyridylethyl, pyridylpropyl, pyridylpentyl and the like.

The "nitrogen-containing heterocyclic group" formed by $R^1$ and $R^2$ bonded to each other is a 5- to 7-membered, preferably 5- or 6-membered, aromatic or nonaromatic monocyclic group, or 8- to 14-membered, preferably 8- to 10-membered, aromatic or nonaromatic fused cyclic group, each of which has at least one nitrogen atom and optionally has, besides carbon atom, 1 to 4, preferably 1 or 2, hetero atoms selected from nitrogen atom, oxygen atom and sulfur atom, and which is bonded at the nitrogen atom on the ring. Examples of —N($R^1$)($R^2$) of the formula (I) include monocyclic groups such as 1-pyrrolidinyl, 1-piperidinyl, 1-homopiperidinyl, 1-piperazinyl, 1-homopiperazinyl, 4-morpholinyl, 1-pyrrolyl, 1-triazolyl and the like, fused cyclic groups such as 1-indolyl, 1-benzimidazolyl, 3-aza-bicyclo[3.3.0]octan-3-yl, 2-isoindolyl, 1,2-dihydroisoindol-2-yl and the like, and the like. As the nitrogen-containing heterocyclic group, 1-pyrrolidinyl is preferable.

The "aryloxy group" is an "aryl-oxy group" constituted with the aforementioned "aryl group" and oxygen atom, and examples thereof include phenoxy, naphthyloxy, anthryloxy and the like.

The "arylthio group" is an "aryl-thio group" constituted with the aforementioned "aryl group" and sulfur atom, and examples thereof include phenylthio, naphthylthio, anthrylthio and the like.

The "heteroaryloxy group" is a "heteroaryl-oxy group" constituted with the aforementioned "heteroaryl group" and oxygen atom, and examples thereof include pyridyloxy, thienyloxy, quinolyloxy, isoquinolyloxy, indolyloxy and the like.

The "C7-15 aralkyloxy group" is an "aryl-alkoxy group" having a total carbon number of 7 to 15, which is constituted with the aforementioned "aryl group" and "C1-8 alkoxy group", and examples thereof include benzyloxy, phenethyloxy, phenylpropyloxy, phenylbutyloxy, naphthylmethyloxy, anthrylmethyloxy and the like.

The "heterocyclyl" is a 5- to 9-membered, preferably 5- or 6-membered, aromatic or nonaromatic monocyclic group, or 8- to 14-membered, preferably 8- to 10-membered, aromatic or nonaromatic fused cyclic group, each of which has, besides carbon atom, 1 to 4, preferably 1 or 2, hetero atoms selected from nitrogen atom, oxygen atom and sulfur atom, and examples thereof include monocyclic heterocyclyl groups such as pyridyl, pyrimidyl, pyridazinyl, pyrazyl, furyl, thienyl, pyrrolyl, pyrazolyl, imidazolyl, oxazolyl, isoxazolyl, thiazolyl, triazolyl, tetrazolyl, pyrrolidinyl, piperidinyl, homopiperidinyl, piperazinyl, homopiperazinyl, morpholinyl, dioxolyl, dioxanyl and the like, fused heterocyclyl groups such as indolyl, isoindolyl, quinolizinyl, isoquinolyl, quinolyl, naphthyridyl, quinazolinyl, benzofuranyl, benzothienyl, benzothiazolyl, benzodioxolyl, benzodioxanyl and the like, and the like.

The "heterocyclylalkyl group" is a "heterocyclyl-alkyl group" constituted with the aforementioned "heterocyclyl" and "C 1-8 alkyl group", and examples thereof include pyridylmethyl, thiazolylmethyl, quinolylmethyl, benzothienylmethyl, benzodioxanylmethyl, piperidinylmethyl, piperazinylmethyl, piperidinylethyl, piperidinylpropyl, piperidinylpentyl and the like.

The "heterocyclylalkyloxy group" is a "heterocyclyl-alkoxy group" constituted with the aforementioned "heterocyclyl" and "C1-8 alkoxy group", and examples thereof include pyridylmethyloxy, thiazolylmethyloxy, quinolylmethyloxy, benzothienylmethyloxy, benzodioxanylmethyloxy, piperidinylmethyloxy, piperazinylmethyloxy, piperidinylethyloxy, piperidinylpropyloxy, piperidinylpentyloxy and the like.

The "acyl group" is a group constituted with a hydrogen atom, the aforementioned "C1-8 alkyl group", "C3-8 cycloalkyl group", "C2-8 alkenyl group", "aryl group" or "C7-15 aralkyl group", and carbonyl, and examples thereof include formyl, acetyl, propionyl, butyryl, isobutyryl, valeryl, isovaleryl, pivaloyl, benzoyl and the like.

The "acyloxy group" is an "acyl-oxy group" constituted with the aforementioned "acyl group" and oxygen atom, and examples thereof include formyloxy, acetyloxy, propionyloxy, butyryloxy, isobutyryloxy, valeryloxy, isovaleryloxy, pivaloyloxy, benzoyloxy and the like.

The "acylamino group" is an "acyl-amino group" constituted with the aforementioned "acyl group" and an amino group, and examples thereof include formylamino, acetylamino, propionylamino, butyrylamino, isobutyrylamino, valerylamino, isovalerylamino, pivaloylamino, benzoylamino and the like.

The "pharmacologically acceptable salt" of compound (I) is not particularly limited as long as it is a pharmacologically acceptable salt. Examples thereof include inorganic acid salts such as hydrochloride, hydrobromide, nitrate, sulfate, phosphate and the like, carboxylic acid salts such as acetate, oxalate, fumarate, maleate, malonate, citrate, succinate, malate and the like, sulfonates such as methanesulfonate, benzenesulfonate, p-toluenesulfonate and the like, alkali metal salts such as lithium salt, sodium salt, potassium salt and the like, alkaline earth metal salts such as calcium salt, magnesium salt and the like, and the like.

Since compound (I) of the present invention has an imine structure, a geometric isomer having a (E) or (Z) configuration exists. The present invention encompasses respective isomers and a mixture of two isomers.

In addition, when an optical isomer of the compound (I) of the present invention exists, respective isomers and a mixture of the isomers are encompassed.

Here, the compound (I) of the present invention also encompasses prodrug.

The "prodrug" is a derivative of the compound of the present invention, which has a chemically or metabolically decomposable group, and, after administration to the body, restores to the original compound and shows the inherent efficacy. It includes a complex and a salt free from a covalent bond.

Examples of the prodrug of the compound (I) of the present invention include a compound (I), wherein the carboxyl group is modified by ethyl group, pivaloyloxymethyl group, 1-(acetyloxy)ethyl group, 1-(ethoxycarbonyloxy)ethyl group, 1-(cyclohexyloxycarbonyloxy)ethyl group, carboxylmethyl group, (5-methyl-2-oxo-1,3-dioxol-4-yl)methyl group, phenyl group, o-tolyl group and the like; a compound (I), wherein the hydroxyl group is modified by acetyl group, propionyl group, isobutyryl group, pivaloyl group, benzoyl group, 4-methylbenzoyl group, dimethylcarbamoyl group or sulfonyl group; a compound (I), wherein the amino group is modified by hexylcarbamoyl group, 3-methylthio-1-(acetylamino)propylcarbonyl group, 1-sulfo-1-(3-ethoxy-4-hydroxyphenyl)methyl group, (5-methyl-2-oxo-1,3-dioxol-4-yl)methyl group and the like; and the like.

Preferable examples of the symbols used in the present invention are explained in the following.

In the formula (I), $R^1$ and $R^2$ are the same or different and each is preferably a C1-6 alkyl group (e.g., methyl, ethyl, propyl, hexyl, isopentyl, neopentyl etc.), a C3-8 cycloalkyl group, a C7-10 aralkyl group (e.g., benzyl, 2-phenethyl, 3-phenylpropyl etc.) optionally having 1 to 5 substituents selected from substituent group A or a phenyl group optionally having one substituent selected from substituent group A, a heteroarylalkyl group optionally having one substituent selected from substituent group A, or a nitrogen-containing heterocyclic group formed by binding to each other (1-pyrrolidinyl, 3-aza-bicyclo[3.3.0]octan-3-yl, 1,2-dihydroisoindol-2-yl, 1-indolyl, 1-piperidinyl, 1-homopiperidinyl, 4-morpholinyl, 1-piperazinyl etc.), more preferably methyl, ethyl, propyl, hexyl, isopentyl, neopentyl, cyclopentyl, benzyl, 4-methylbenzyl, 4-isopropylbenzyl, 4-t-butylbenzyl, 4-trifluoromethylbenzyl, 4-methoxybenzyl, 2,4-dichlorobenzyl, 4-chlorophenethyl, 3-phenylpropyl, phenyl, 4-chlorophenyl, 2,4-dichlorophenyl, 4-t-butylphenyl or 3-furylmethyl, or 1-pyrrolidinyl, 3-aza-bicyclo[3.3.0]octan-3-yl, 1,2-dihydroisoindol-2-yl, 5-trifluoromethyl-1,2-dihydroisoindol-2-yl, 3-chloro-1-indolyl, 1-piperidinyl, 2,6-dimethyl-1-piperidinyl, 1-homopiperidinyl, 4-morpholinyl or N-methylpiperazin-1-yl, which is formed by binding to each other, and more preferably a methyl group.

As X, CH is preferable.

As Ar, a phenyl group optionally having 1 or 2 substituents selected from substituent group A or a heteroaryl group optionally having 1 or 2 substituents selected from substituent group A is preferable, 2-methylphenyl, 3-methylphenyl, 4-methylphenyl, 2,4-dimethylphenyl, 2-ethylphenyl, 2-trifluoromethylphenyl, 2-phenoxymethylphenyl, 2-phenylthiomethylphenyl, 2-benzylphenyl, 2-phenethylphenyl, 2-phenylpropylphenyl, 2-methoxyphenyl, 2-ethoxyphenyl, 2-propoxyphenyl, 2-butoxyphenyl, 2-pentyloxyphenyl, 2-hexyloxyphenyl, 2-trifluoromethoxyphenyl, 2-(2-ethoxyethoxy)phenyl, 2-(2-phenoxyethoxy)phenyl, 2-[2-(4-chlorophenoxy)ethoxy]phenyl, 2-(3-phenoxypropoxy)phenyl, 2-(4-chlorophenoxy)methoxyphenyl, 2-(3-cyanopropoxy) phenyl, 2-(3-morpholinylpropoxy)phenyl, 2-methylthiophenyl, 2-ethylthiophenyl, 2-propylthiophenyl, 2-butylthiophenyl, 2-pentylthiophenyl, 2-hexylthiophenyl, 2-dimethylaminophenyl, 2-ethylmethylaminophenyl, 2-diethylaminophenyl, 2-methylpropylaminophenyl, 2-butylmethylaminophenyl, 2-methylpentylaminophenyl, 2-benzylmethylaminophenyl, 2-methanesulfonylphenyl, 2-acetylphenyl, 2-benzoylphenyl, 2-acetoxyphenyl, 2-methoxycarbonylphenyl, 2-fluorophenyl, 2-chlorophenyl, 3-chlorophenyl, 4-chlorophenyl, 2,4-dichlorophenyl, 2-hydroxyphenyl, 4-carboxyphenyl, 2-nitrophenyl, 2-cyanophenyl, biphenyl, 2-phenoxyphenyl, 2-benzyloxyphenyl, 2-(3-chlorobenzyloxy)phenyl, 2-(2,4-dichlorobenzyloxy)phenyl, 2-(4-fluorobenzyloxy)phenyl, 2-(4-isopropylbenzyloxy) phenyl, 2-(4-trifluoromethoxybenzyloxy)phenyl, 2-phenethyloxyphenyl, 2-phenylethoxyphenyl, 2-allyloxyphenyl, 3-pentyloxypyridin-2-yl, 3-methylthiopyridin-2-yl, 2-methylfuran-3-yl, 3-methylthiophen-2-yl, 2,5-dichlorothiophen-3-yl, N-hexylpyrrol-2-yl, 3-methylbenzofuran-2-yl group and the like are more preferable, and a phenyl group having a substituent at the 2-position, for example, 2-ethylphenyl group, 2-ethoxyphenyl group, 2-propoxyphenyl group, 2-isopropoxyphenyl group, 2-butoxyphenyl group, 2-allyloxyphenyl group, 2-(2-phenoxyethoxy)phenyl group, 2-trifluoromethoxyphenyl group, 2-methylthiophenyl group, 2-ethylthiophenyl group, 2-propylthiophenyl group, 2-butylthiophenyl group, 2-phenethylthiophenyl group, 2-(4-methoxybenzyloxy) phenyl group, 2-(4-fluorophenethyloxy)phenyl group, 2-(4-dimethylaminophenethyloxy)phenyl group, 2-[2-(4-methoxyphenoxy)ethoxy]phenyl group, 2-(3-phenoxypropoxy)phenyl group and the like are particularly preferable.

Specific examples of preferable compound of the present invention are as follows.

N'-[1-(2-ethylphenyl)-1-imidazol-1-ylmethylidene]-N,N-dimethylhydrazine (compound No. 4),
N'-[1-(2-ethoxyphenyl)-1-imidazol-1-ylmethylidene]-N,N-dimethylhydrazine (compound No. 16),
N'-[1-imidazol-1-yl-1-(2-propoxyphenyl)methylidene]-N,N-dimethylhydrazine (compound No. 17),
N'-[1-imidazol-1-yl-1-(2-isopropoxyphenyl)methylidene]-N,N-dimethylhydrazine (compound No. 19),
N'-[1-(2-butoxyphenyl)-1-imidazol-1-ylmethylidene]-N,N-dimethylhydrazine (compound No. 23),
N'-[1-(2-allyloxyphenyl)-1-imidazol-1-ylmethylidene]-N,N-dimethylhydrazine (compound No. 20),
N'-[1-imidazol-1-yl-1-[2-(2-phenoxyethoxy)phenyl]methylidene]-N,N-dimethylhydrazine (compound No. 66),
N'-[1-imidazol-1-yl-1-(2-trifluoromethoxyphenyl)methylidene]-N,N-dimethylhydrazine (compound No. 32),
N'-[1-imidazol-1-yl-1-(2-methylthiophenyl)methylidene]-N,N-dimethylhydrazine (compound No. 79),
N'-[1-(2-ethylthiophenyl)-1-imidazol-1-ylmethylidene]-N,N-dimethylhydrazine (compound No. 80),
N'-[1-imidazol-1-yl-1-(2-propylthiophenyl)methylidene]-N,N-dimethylhydrazine (compound No. 81),
N'-[1-(2-butylthiophenyl)-1-imidazol-1-ylmethylidene]-N,N-dimethylhydrazine (compound No. 82),
N'-[1-imidazol-1-yl-1-(2-phenethylthiophenyl)methylidene]-N,N-dimethylhydrazine (compound No. 84),
N'-[1-imidazol-1-yl-1-[2-(4-methoxybenzyloxy)phenyl]methylidene]-N,N-dimethylhydrazine (compound No. 52),
N'-[1-[2-[2-(4-fluorophenyl)ethoxy]phenyl]-1-imidazol-1-ylmethylidene]-N,N-dimethylhydrazine (compound No. 57), N'-[1-imidazol-1-yl-1-[2-(4-dimethylaminophenethyloxy)phenyl]methylidene]-N,N-dimethylhydrazine (compound No. 60), N'-[1-imidazol-1-yl-1-[2-[2-(4-methoxyphenoxy)ethoxy]phenyl]methylidene]-N,N-dimethylhydrazine (compound No. 69), and N'-[1-imidazol-1-yl-1-[2-(3-phenoxypropoxy)phenyl]methylidene]-N,N-dimethylhydrazine (compound No. 70).

The following Table 1 and Table 2 show specific examples of the compound represented by the formula (I). However, the present invention is not limited to the following compounds.

In the following Tables, Ph is phenyl. The "higher polar" and "lower polar" shows either (E)-form or (Z)-form, and a compound showing a smaller Rf value by thin layer chromatography is indicated as higher polar.

TABLE 1

| Compound No. | R$^1$ | R$^2$ | X | Ar |
|---|---|---|---|---|
| 1 | CH$_3$— | CH$_3$— | CH | 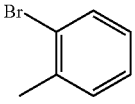 |
| 2 | CH$_3$— | CH$_3$— | CH | 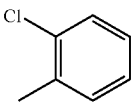 |
| 3 | CH$_3$— | CH$_3$— | CH | 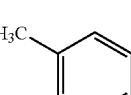 |
| 4 | CH$_3$— | CH$_3$— | CH | 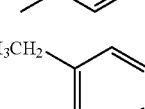 |
| 5 | CH$_3$— | CH$_3$— | CH | 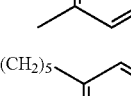 |
| 6 | CH$_3$— | CH$_3$— | CH | 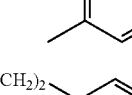 |
| 7 | CH$_3$— | CH$_3$— | CH | 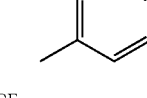 |
| 8 | CH$_3$— | CH$_3$— | CH | 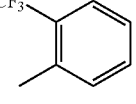 |
| 9 | CH$_3$— | CH$_3$— | CH | 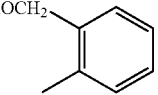 |
| 10 | CH$_3$— | CH$_3$— | CH | 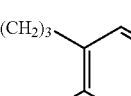 |
| 11 | CH$_3$— | CH$_3$— | CH | 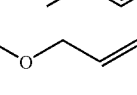 |
| 12 | CH$_3$— | CH$_3$— | CH | 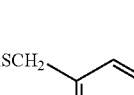 |

TABLE 1-continued
| Compound No. | R¹ | R² | X | Ar |
|---|---|---|---|---|
| 13 | CH₃— | CH₃— | CH | 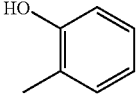 |
| 14 | CH₃— | CH₃— | CH | 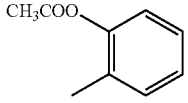 |
| 15 | CH₃— | CH₃— | CH | 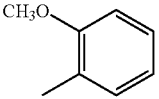 |
| 16 | CH₃— | CH₃— | CH | 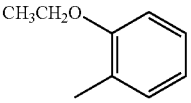 |
| 17 | CH₃— | CH₃— | CH | 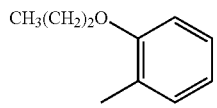 |
| 18 | CH₃— | CH₃— | N | 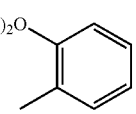 |
| 19 | CH₃— | CH₃— | CH | 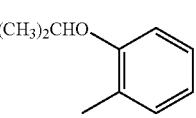 |
| 20 | CH₃— | CH₃— | CH | 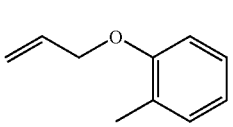 |
| 21 | CH₃— | CH₃— | CH | 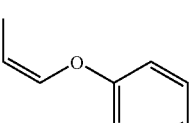 |
| 22 | CH₃— | CH₃— | CH | 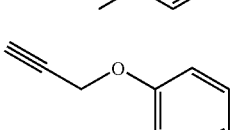 |
| 23 | CH₃— | CH₃— | CH | 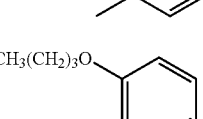 |
| 24 | CH₃— | CH₃— | CH | 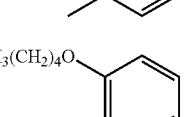 |
| 25 | CH₃— | CH₃— | CH | 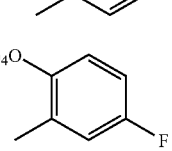 |

TABLE 1-continued

| Compound No. | R¹ | R² | X | Ar |
|---|---|---|---|---|
| 26 | $CH_3-$ | $CH_3-$ | CH | 3-($O(CH_2)_4CH_3$)-2-methylphenyl |
| 27 | $CH_3-$ | $CH_3-$ | CH | 4-($O(CH_2)_4CH_3$)-3-methylphenyl |
| 28 | $CH_3-$ | $CH_3-$ | CH | 2-($CH_3(CH_2)_5O$)-6-methylphenyl |
| 29 | $CH_3-$ | $CH_3-$ | CH | 2-($CH_3(CH_2)_2OCH_2O$)-6-methylphenyl |
| 30 | $CH_3-$ | $CH_3-$ | CH | 2-($CH_3CH_2O(CH_2)_2O$)-6-methylphenyl |
| 31 | $CH_3-$ | $CH_3-$ | CH | 2-($NC(CH_2)_3O$)-6-methylphenyl |
| 32 | $CH_3-$ | $CH_3-$ | CH | 2-($CF_3O$)-6-methylphenyl |
| 33 | $CH_3-$ | $CH_3-$ | CH | 2-($CHF_2CF_2O$)-6-methylphenyl |
| 34 | $CH_3-$ | $CH_3-$ | CH | 2-(benzyloxy)-6-methylphenyl |
| 35 | $CH_3-$ | $CH_3-$ | CH | 2-((4-fluorobenzyl)oxy)-6-methylphenyl |
| 36 | $CH_3-$ | $CH_3-$ | CH | 2-((3-fluorobenzyl)oxy)-6-methylphenyl |

TABLE 1-continued
| Compound No. | R¹ | R² | X | Ar |
|---|---|---|---|---|
| 37 | CH₃— | CH₃— | CH | 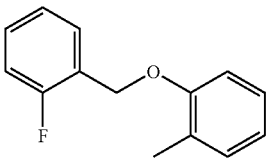 |
| 38 | CH₃— | CH₃— | CH | 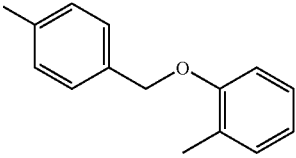 |
| 39 | CH₃— | CH₃— | N | 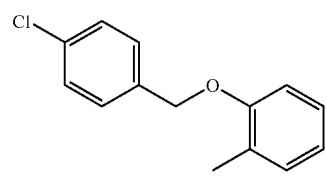 |
| 40 | CH₃— | CH₃— | CH | 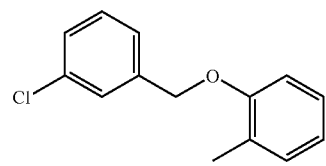 |
| 41 | CH₃— | CH₃— | CH | 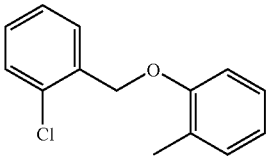 |
| 42 | CH₃— | CH₃— | CH | 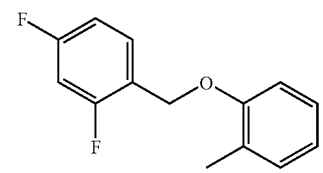 |
| 43 | CH₃— | CH₃— | CH | 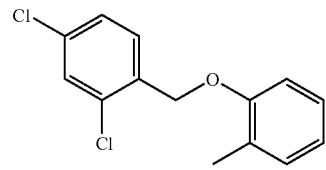 |
| 44 | CH₃— | CH₃— | CH | 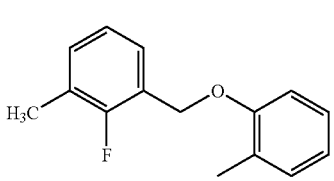 |

TABLE 1-continued

| Compound No. | R¹ | R² | X | Ar |
|---|---|---|---|---|
| 45 | CH₃— | CH₃— | CH | pentafluorobenzyl-O-(2-methylphenyl) |
| 46 | CH₃— | CH₃— | CH | 4-methylbenzyl-O-(2-methylphenyl) |
| 47 | CH₃— | CH₃— | CH | 2,4-dimethylbenzyl-O-(2-methylphenyl) |
| 48 | CH₃— | CH₃— | CH | 4-ethylbenzyl-O-(2-methylphenyl) |
| 49 | CH₃— | CH₃— | CH | 4-tert-butylbenzyl-O-(2-methylphenyl) |
| 50 | CH₃— | CH₃— | CH | 4-trifluoromethylbenzyl-O-(2-methylphenyl) |
| 51 | CH₃— | CH₃— | CH | 3-trifluoromethylbenzyl-O-(2-methylphenyl) |
| 52 | CH₃— | CH₃— | CH | 4-methoxybenzyl-O-(2-methylphenyl) |

TABLE 1-continued
| Compound No. | R¹ | R² | X | Ar |
|---|---|---|---|---|
| 53 | CH₃— | CH₃— | CH | 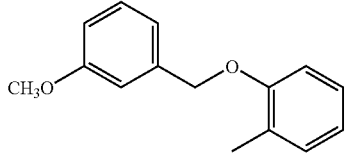 |
| 54 | CH₃— | CH₃— | CH | 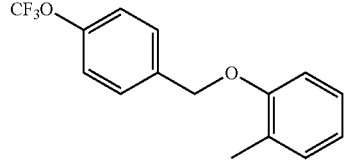 |
| 55 | CH₃— | CH₃— | CH | 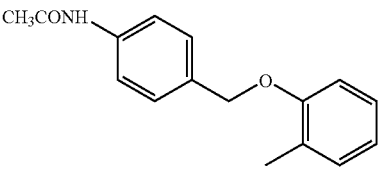 |
| 56 | CH₃— | CH₃— | CH | 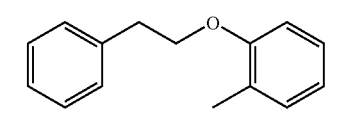 |
| 57 | CH₃— | CH₃— | CH | 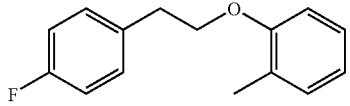 |
| 58 | CH₃— | CH₃— | CH | 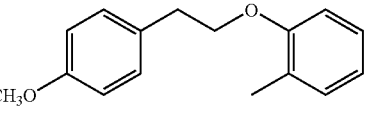 |
| 59 lower polar | CH₃— | CH₃— | CH | 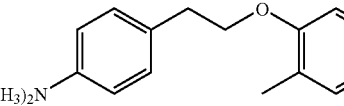 |
| 60 higher polar | CH₃— | CH₃— | CH | 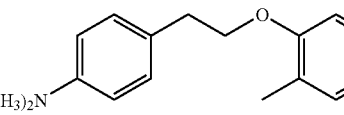 |
| 61 | CH₃— | CH₃— | CH | 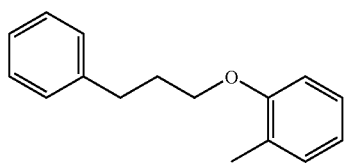 |
| 62 | CH₃— | CH₃— | CH | 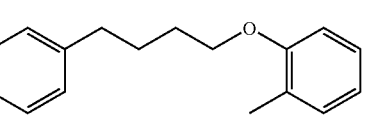 |
| 63 | CH₃— | CH₃— | CH | 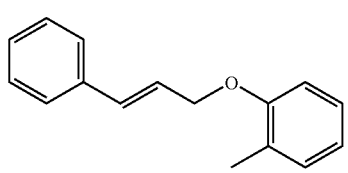 |

TABLE 1-continued
| Compound No. | R¹ | R² | X | Ar |
|---|---|---|---|---|
| 64 | CH₃— | CH₃— | CH | 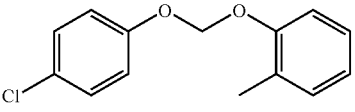 |
| 65 lower polar | CH₃— | CH₃— | CH | 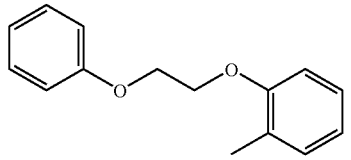 |
| 66 higher polar | CH₃— | CH₃— | CH | 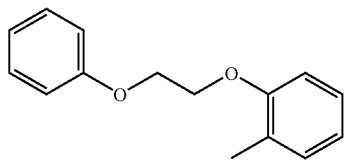 |
| 67 | CH₃— | CH₃— | N | 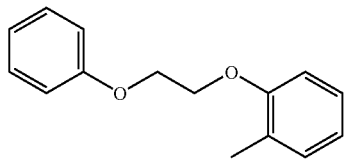 |
| 68 | CH₃— | CH₃— | CH | 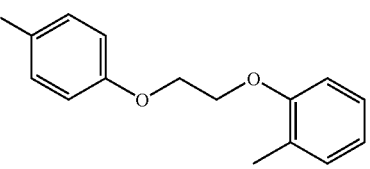 |
| 69 | CH₃— | CH₃— | CH | 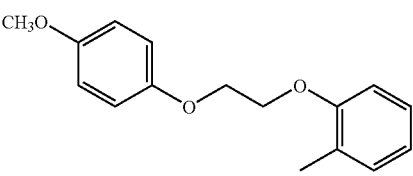 |
| 70 | CH₃— | CH₃— | CH | 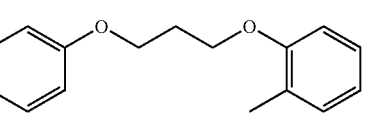 |
| 71 | CH₃— | CH₃— | CH | 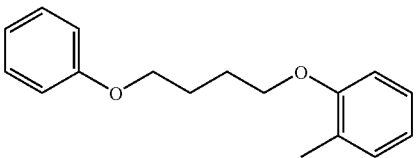 |
| 72 | CH₃— | CH₃— | CH | 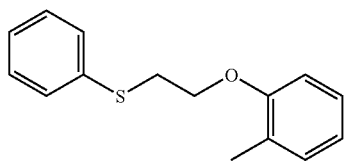 |

TABLE 1-continued

| Compound No. | R¹ | R² | X | Ar |
|---|---|---|---|---|
| 73 | CH₃— | CH₃— | CH | benzodioxane-CH₂-O-(2-methylphenyl) |
| 74 | CH₃— | CH₃— | CH | pyridin-2-yl-CH₂-O-(2-methylphenyl) |
| 75 | CH₃— | CH₃— | CH | pyridin-2-yl-CH₂CH₂-O-(2-methylphenyl) |
| 76 | CH₃— | CH₃— | CH | pyridin-3-yl-O-CH₂CH₂-O-(2-methylphenyl) |
| 77 | CH₃— | CH₃— | CH | 2-(4-chlorophenyl)thiazol-4-yl-CH₂-O-(2-methylphenyl) |
| 78 | CH₃— | CH₃— | CH | 5-chlorobenzothiophen-2-yl-CH₂-O-(2-methylphenyl) |
| 79 | CH₃— | CH₃— | CH | CH₃S-(2-methylphenyl) |
| 80 | CH₃— | CH₃— | CH | CH₃CH₂S-(2-methylphenyl) |
| 81 | CH₃— | CH₃— | CH | CH₃(CH₂)₂S-(2-methylphenyl) |
| 82 | CH₃— | CH₃— | CH | CH₃(CH₂)₃S-(2-methylphenyl) |
| 83 | CH₃— | CH₃— | CH | CH₃(CH₂)₄S-(2-methylphenyl) |

TABLE 1-continued

| Compound No. | R¹ | R² | X | Ar |
|---|---|---|---|---|
| 84 | CH₃— | CH₃— | CH | 2-methylphenyl with Ph(CH₂)₂S— at ortho position |
| 85 | CH₃— | CH₃— | CH | 2-methylphenyl with —S-CH₂CH₂-O-Ph at ortho position |
| 86 | CH₃— | CH₃— | CH | 2-methylphenyl with CH₃SO₂— at ortho position |
| 87 | CH₃— | CH₃— | CH | 2-methylphenyl with N(CH₃)(CH₂)₄CH₃ at ortho position |
| 88 | CH₃— | CH₃— | CH | 2-methylphenyl with N(CH₃)CH₂CH₂-O-Ph at ortho position |
| 89 | CH₃— | CH₃— | CH | 2-methylphenyl with N(CH₃)(CH₂Ph) at ortho position |
| 90 | CH₃— | CH₃— | CH | 2-methyl-4-bromophenyl with N(CH₃)(CH₂Ph) |
| 91 | CH₃— | CH₃— | CH | 2-methylphenyl with CH₃SO₂NH— at ortho position |
| 92 | CH₃— | CH₃— | CH | 2-methylnaphthalen-1-yl with CH₃(CH₂)₄O— |
| 93 | CH₃— | CH₃— | CH | 1-methylnaphthalen-2-yl with CH₃(CH₂)₄O— |

TABLE 1-continued
| Compound No. | R¹ | R² | X | Ar |
|---|---|---|---|---|
| 94 | CH₃— | CH₃— | CH | 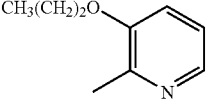 |
| 95 | CH₃— | CH₃— | CH | 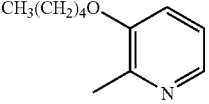 |
| 96 | CH₃— | CH₃— | CH | 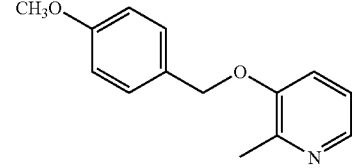 |
| 97 | CH₃— | CH₃— | CH | 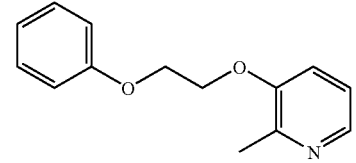 |
| 98 | CH₃— | CH₃— | CH | 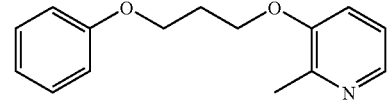 |
| 99 | CH₃— | CH₃— | CH | 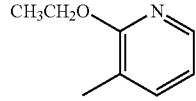 |
| 100 | CH₃— | CH₃— | CH | 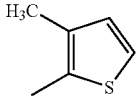 |
| 101 | CH₃— | CH₃— | CH | 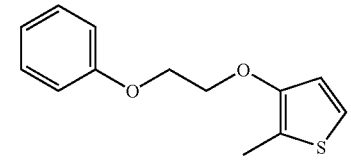 |
| 102 higher polar | CH₃— | CH₃— | CH | 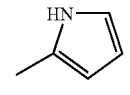 |
| 103 lower polar | CH₃— | CH₃— | CH | 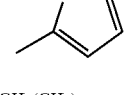 |
| 104 | CH₃— | CH₃— | CH | 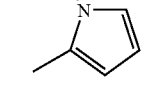 |
| 105 | CH₃— | CH₃— | CH | 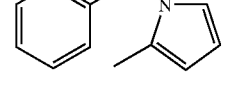 |

TABLE 1-continued
| Compound No. | R¹ | R² | X | Ar |
|---|---|---|---|---|
| 106 | CH₃— | CH₃— | CH | 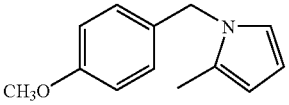 |
| 107 | CH₃— | CH₃— | CH | 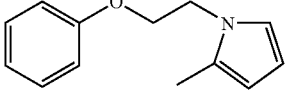 |
| 108 | CH₃— | CH₃— | CH | 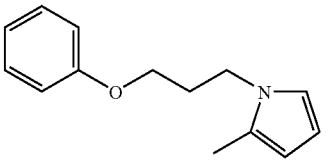 |
| 109 | CH₃— | CH₃— | CH | 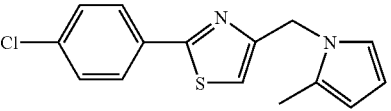 |
| 110 | CH₃— | CH₃— | CH | 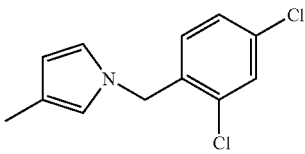 |
| 111 lower polar | CH₃— | CH₃— | CH | 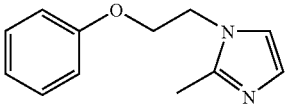 |
| 112 higher polar | CH₃— | CH₃— | CH | 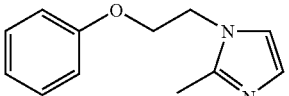 |
| 113 | CH₃CH₂— | CH₃— | CH | 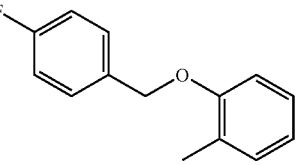 |
| 114 | CH₃CH₂— | CH₃— | CH | 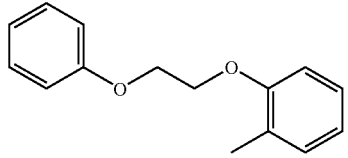 |
| 115 | CH₃CH₂— | CH₃— | CH | 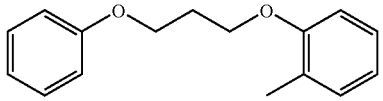 |
| 116 | CH₃CH₂— | CH₃— | CH | 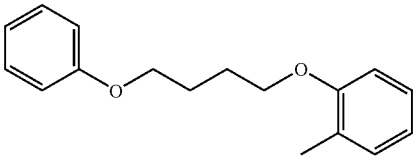 |

TABLE 1-continued
| Compound No. | R¹ | R² | X | Ar |
|---|---|---|---|---|
| 117 | CH₃CH₂— | CH₃CH₂— | CH | 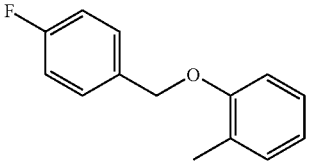 |
| 118 | CH₃CH₂— | CH₃CH₂— | CH | 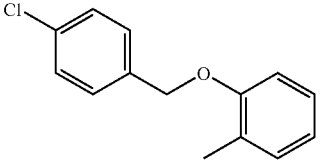 |
| 119 | CH₃CH₂— | CH₃CH₂— | CH | 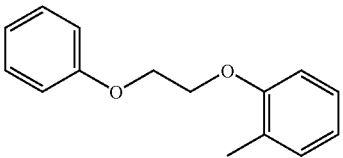 |
| 120 | CH₃CH₂— | CH₃CH₂— | CH | 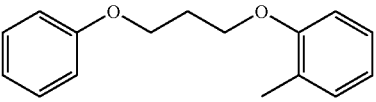 |
| 121 | CH₃(CH₂)₂— | CH₃(CH₂)₂— | CH | 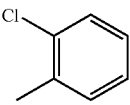 |
| 122 | CH₃(CH₂)₅— | CH₃CH₂— | CH | 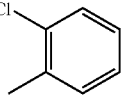 |
| 123 | CH₃(CH₂)₅— | CH₃(CH₂)₂— | CH | 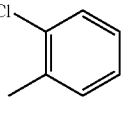 |
| 124 | CH₃(CH₂)₅— | CH₃(CH₂)₅— | CH | 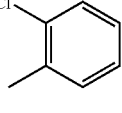 |
| 125 | (CH₃)₂CH(CH₂)₂— | CH₃CH₂— | CH | 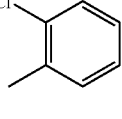 |
| 126 | (CH₃)₂CH(CH₂)₂— | (CH₃)₂CH(CH₂)₂— | CH | 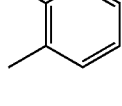 |
| 127 | (CH₃)₃CCH₂— | CH₃CH₂— | CH | 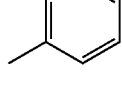 |

TABLE 1-continued

| Compound No. | R¹ | R² | X | Ar |
|---|---|---|---|---|
| 128 | Cyclopentyl- | $CH_3$— | CH | 2-(2-phenoxyethoxy)-methylphenyl |
| 129 | 4-Cl—$PhCH_2$— | $CH_3CH_2$— | CH | 2-Cl, methylphenyl |
| 130 | 2,4-diCl—$PhCH_2$— | $CH_3(CH_2)_2$— | CH | 2-Cl, methylphenyl |
| 131 | 2,4-diCl-$PhCH_2$— | $CH_3(CH_2)_5$— | CH | 2-Cl, methylphenyl |
| 132 | 4-$CH_3$—$PhCH_2$— | $CH_3$— | CH | 2-Cl, methylphenyl |
| 133 | 4-$CF_3$—$PhCH_2$— | $CH_3CH_2$— | CH | 2-$H_3C$, methylphenyl |
| 134 | 4-$(CH_3)_3C$—$PhCH_2$— | $CH_3(CH_2)_2$— | CH | 2-Cl, methylphenyl |
| 135 | 4-$CH_3O$—$PhCH_2$— | $CH_3CH_2$— | CH | 2-$H_3C$, methylphenyl |
| 136 | $Ph(CH_2)_3$— | $CH_3CH_2$— | CH | 2-Cl, methylphenyl |
| 137 | $Ph(CH_2)_3$— | $Ph(CH_2)_3$— | CH | 2-Cl, methylphenyl |
| 138 | Ph— | $CH_3$— | CH | 2-Cl, methylphenyl |
| 139 | Ph— | $CH_3$— | CH | 4-Cl, 3-methyl, (2-methylphenoxy)methyl |

TABLE 1-continued
| Compound No. | R¹ | R² | X | Ar |
|---|---|---|---|---|
| 140 | Ph— | CH₃— | CH | 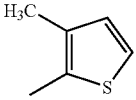 |
| 141 | 4-Cl—Ph— | CH₃— | CH | 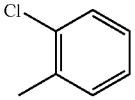 |
| 142 | 4-Cl—Ph— | CH₃— | CH | 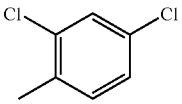 |
| 143 | 4-Cl—Ph— | CH₃— | CH | 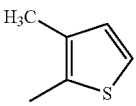 |
| 144 | 4-Cl—Ph— | CH₃CH₂— | CH | 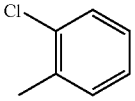 |
| 145 | 4-Cl—Ph— | CH₃(CH₂)₂— | CH | 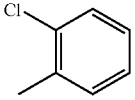 |
| 146 | 2,4-diCl—Ph— | CH₃— | CH | 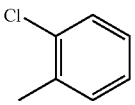 |
| 147 | 4-(CH₃)₂C—Ph— | CH₃— | CH | 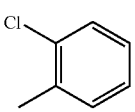 |
| 148 | 4-(CH₃)₃C—Ph— | CH₃CH₂— | CH | 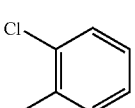 |
| 149 | Ph— | PhCH₂— | CH | 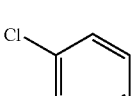 |
| 150 | Ph— | Ph— | CH | 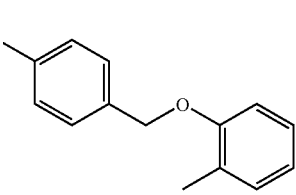 |
| 151 | 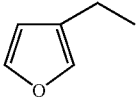 | CH₃CH₂— | CH | 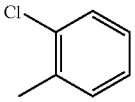 |

TABLE 2

| Compound No. | R¹R²N— | X | Ar |
|---|---|---|---|
| 152 | pyrrolidin-1-yl | CH | 2-chloro-6-methylphenyl |
| 153 | pyrrolidin-1-yl | CH | 2-hydroxy-6-methylphenyl |
| 154 lower polar | pyrrolidin-1-yl | CH | 2-(propoxy)-6-methylphenyl, CH₃(CH₂)₂O— |
| 155 higher polar | pyrrolidin-1-yl | CH | 2-(propoxy)-6-methylphenyl, CH₃(CH₂)₂O— |
| 156 lower polar | pyrrolidin-1-yl | CH | 2-(pentyloxy)-6-methylphenyl, CH₃(CH₂)₄O— |
| 157 higher polar | pyrrolidin-1-yl | CH | 2-(pentyloxy)-6-methylphenyl, CH₃(CH₂)₄O— |
| 158 | pyrrolidin-1-yl | CH | 2-[(4-fluorobenzyl)oxy]-6-methylphenyl |
| 159 | pyrrolidin-1-yl | CH | 2-[(3-fluorobenzyl)oxy]-6-methylphenyl |
| 160 lower polar | pyrrolidin-1-yl | CH | 2-[2-(phenoxy)ethoxy]-6-methylphenyl |
| 161 higher polar | pyrrolidin-1-yl | CH | 2-[2-(phenoxy)ethoxy]-6-methylphenyl |
| 162 | pyrrolidin-1-yl | CH | 2-[2-(4-fluorophenoxy)ethoxy]-6-methylphenyl |

TABLE 2-continued
| Compound No. | R¹R²N— | X | Ar |
|---|---|---|---|
| 163 | 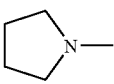 | CH | 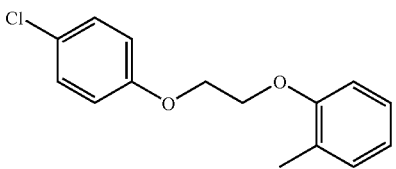 |
| 164 | 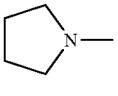 | CH | 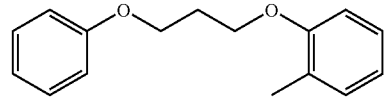 |
| 165 | 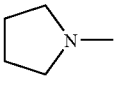 | CH | 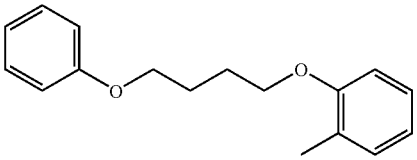 |
| 166 | 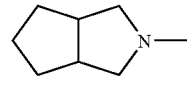 | CH | 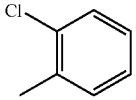 |
| 167 | 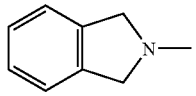 | CH | 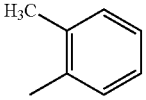 |
| 168 | 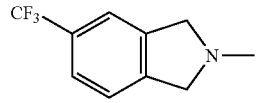 | CH | 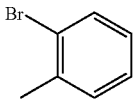 |
| 169 | 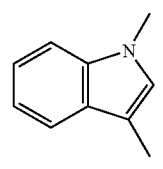 | CH | 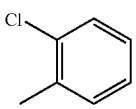 |
| 170 | 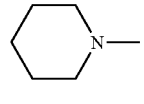 | CH | 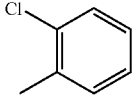 |
| 171 | 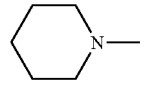 | CH | 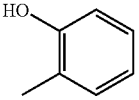 |
| 172 | 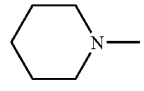 | CH | 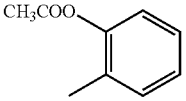 |
| 173 | 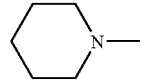 | CH | 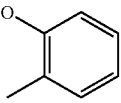 |

TABLE 2-continued

| Compound No. | R¹R²N— | X | Ar |
|---|---|---|---|
| 174 | piperidinyl-N— | CH | 2-methyl-(3-fluorobenzyloxy)phenyl |
| 175 | piperidinyl-N— | CH | 2-methyl-[2-(phenoxy)ethoxy]phenyl |
| 176 | 2,6-dimethylpiperidinyl-N— | CH | 2-chloro-6-methylphenyl |
| 177 | azepan-1-yl— | CH | 2-chloro-6-methylphenyl |
| 178 | azepan-1-yl— | CH | 2,4-dichloro-5-methylphenyl |
| 179 | azepan-1-yl— | CH | 2-chloro-5-bromo-3-methylphenyl |
| 180 | azepan-1-yl— | CH | 2-chloro-4-hydroxy-5-methylphenyl |
| 181 | azepan-1-yl— | CH | 2-chloro-4-(4-chlorobenzyloxy)-methylphenyl |
| 182 | azepan-1-yl— | CH | 2-chloro-4-{[4-chloro-2-(trifluoromethyl)quinolin-6-yl]methoxy}methylphenyl |
| 183 | azepan-1-yl— | CH | 2-bromo-3-methyl-4-methoxyphenyl |
| 184 | azepan-1-yl— | CH | 2-ethyl-6-methylphenyl |

TABLE 2-continued
| Compound No. | R¹R²N— | X | Ar |
|---|---|---|---|
| 185 | 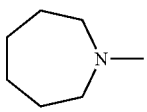 | CH | 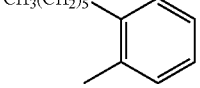 CH$_3$(CH$_2$)$_5$ |
| 186 | 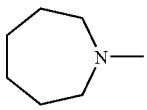 | CH | 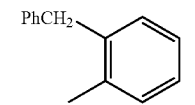 PhCH$_2$ |
| 187 | 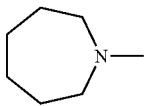 | CH | 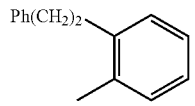 Ph(CH$_2$)$_2$ |
| 188 | 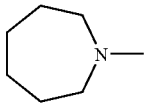 | CH | 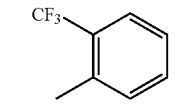 CF$_3$ |
| 189 | 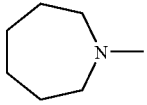 | CH | 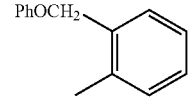 PhOCH$_2$ |
| 190 | 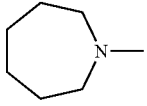 | CH | 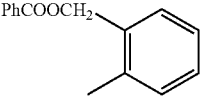 PhCOOCH$_2$ |
| 191 | 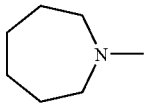 | CH | 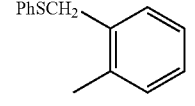 PhSCH$_2$ |
| 192 | 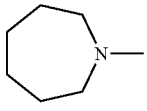 | CH | 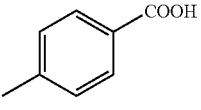 COOH |
| 193 | 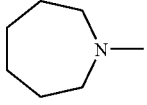 | CH | 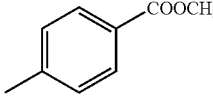 COOCH$_3$ |
| 194 | 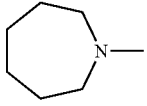 | CH | 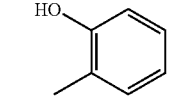 HO |
| 195 | 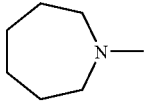 | CH | 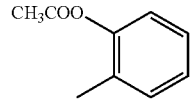 CH$_3$COO |
| 196 | 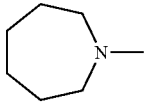 | CH | 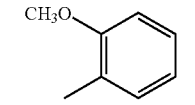 CH$_3$O |
| 197 | 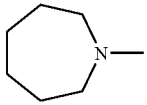 | CH | 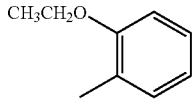 CH$_3$CH$_2$O |

TABLE 2-continued
| Compound No. | R¹R²N— | X | Ar |
|---|---|---|---|
| 198 | 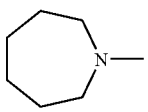 | CH | 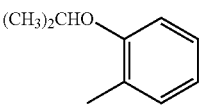 (CH₃)₂CHO— |
| 199 | 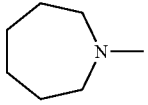 | CH | 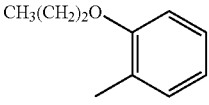 CH₃(CH₂)₂O— |
| 200 | 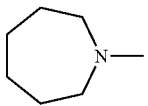 | CH | 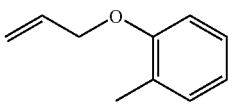 |
| 201 | 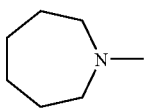 | CH | 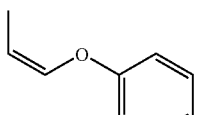 |
| 202 | 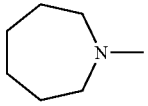 | CH | 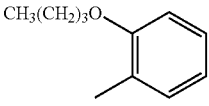 CH₃(CH₂)₃O— |
| 203 | 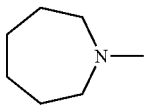 | CH | 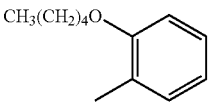 CH₃(CH₂)₄O— |
| 204 | 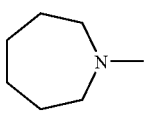 | N | 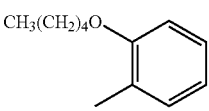 CH₃(CH₂)₄O— |
| 205 | 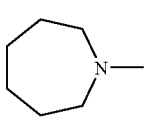 | CH | 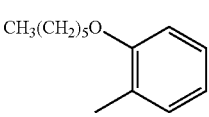 CH₃(CH₂)₅O— |
| 206 | 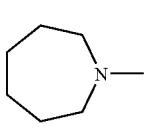 | CH | 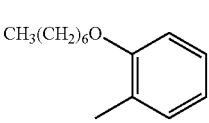 CH₃(CH₂)₆O— |
| 207 | 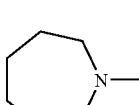 | CH | 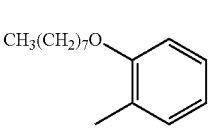 CH₃(CH₂)₇O— |
| 208 | 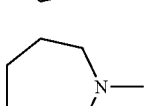 | CH | 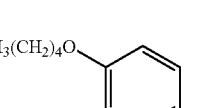 CH₃(CH₂)₄O—, F |
| 209 | 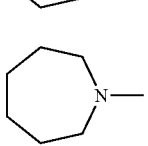 | CH | 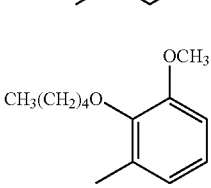 CH₃(CH₂)₄O—, OCH₃ |

TABLE 2-continued
| Compound No. | R¹R²N— | X | Ar |
|---|---|---|---|
| 210 | 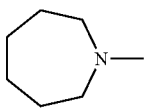 | CH | 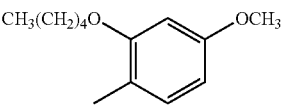 |
| 211 | 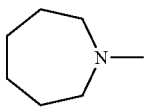 | CH | 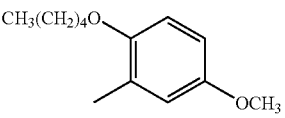 |
| 212 | 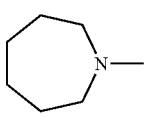 | CH | 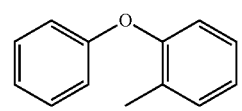 |
| 213 | 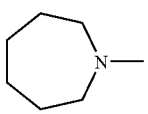 | CH | 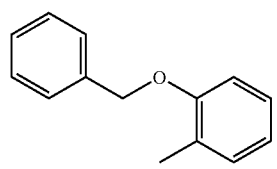 |
| 214 | 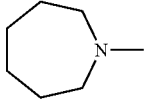 | CH | 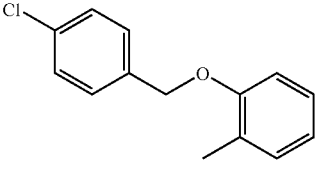 |
| 215 | 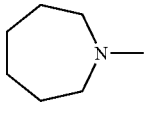 | CH | 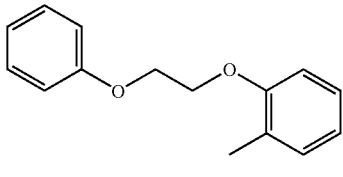 |
| 216 | 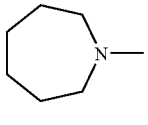 | CH | 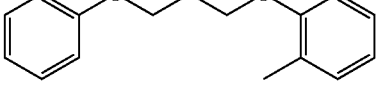 |
| 217 | 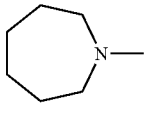 | CH | 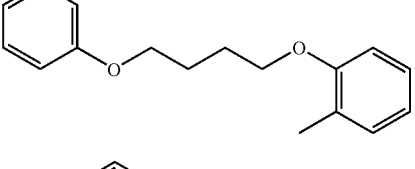 |
| 218 | 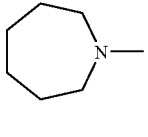 | CH | 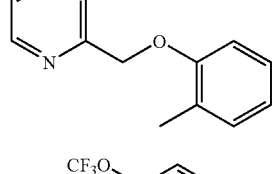 |
| 219 | 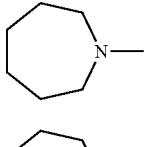 | CH | 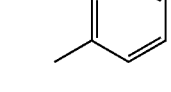 |
| 220 | 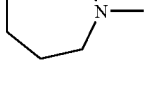 | CH | 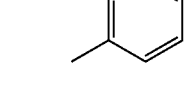 |

TABLE 2-continued
| Compound No. | R¹R²N— | X | Ar |
|---|---|---|---|
| 221 | 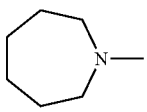 | CH | 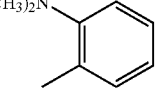 |
| 222 | 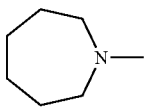 | CH | 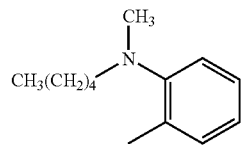 |
| 223 | 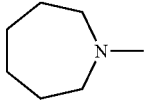 | CH | 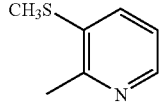 |
| 224 | 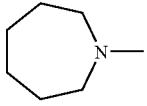 | CH | 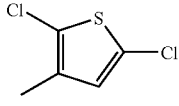 |
| 225 | 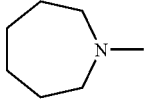 | CH | 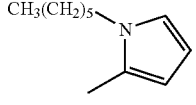 |
| 226 | 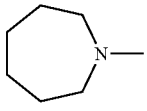 | CH | 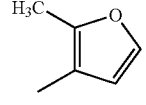 |
| 227 | 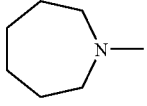 | CH | 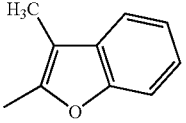 |
| 228 | 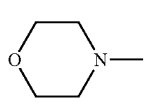 | CH | 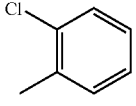 |
| 229 | 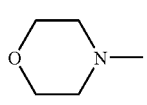 | CH | 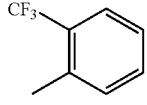 |
| 230 | 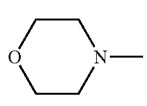 | CH | 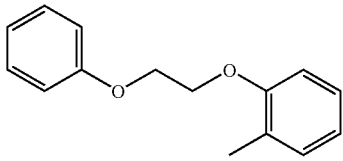 |
| 231 | 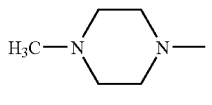 | CH | 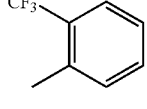 |
| 232 | 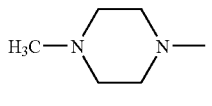 | CH | 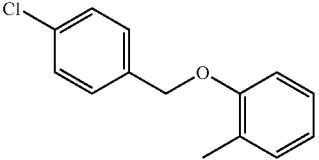 |

TABLE 2-continued

| Compound No. | R¹R²N— | X | Ar |
|---|---|---|---|
| 233 | H₃C—N(piperazine)N— | CH | phenyl-O-CH₂CH₂-O-(2-methylphenyl) |
| 234 | cyclopentyl-N(piperazine)N— | CH | (4-chlorophenyl)-CH₂-O-(2-methylphenyl) |

The compound of the formula (I) of the present invention can be produced according to, for example, the following reaction scheme.

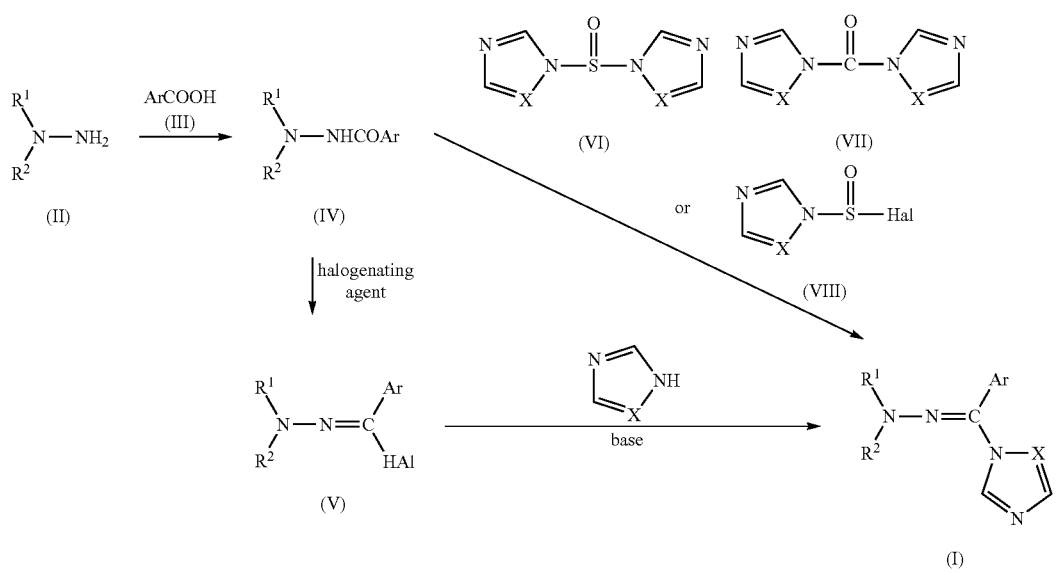

wherein Ar, R¹, R² and X are as defined above, and Hal is chlorine or bromine.

The above-mentioned production method is a method including converting acylhydrazine compound (IV) obtained by a condensation reaction of hydrazine compound (II) and carboxylic acid compound (III) to halide compound (V), and reacting the compound with imidazole or triazole in the presence of a base to give compound (I), or a method including reacting acylhydrazine compound (IV) with thionyldiazole (VI), carbonyldiazole (VII) or compound (VIII) to give compound (I). The method is explained in detail in the following.

When the condensation reaction of hydrazine compound (II) and carboxylic acid compound (III) is performed in the presence of a condensation agent, the condensation agent includes, for examples, carbodiimides such as dicyclohexylcarbodiimide and the like. When a active derivative of carboxylic acid compound (III) is obtained and reacted with hydrazine compound (II), examples of the derivatizing agent include thionyl chloride, phosphorus oxychloride, oxalyl chloride, methanesulfonyl chloride, phosgene, triphosgene, 1,1'-carbonyldiimidazole, ethyl chlorocarbonate and the like.

Examples of the halogenating agent for acylhydrazine compound (IV) include phosphorus pentachloride, phosphorus trichloride, phosphorus tribromide, phosgene, thionyl chloride, phosphorus oxychloride, halogenating agent made of triphenylphosphine and carbon tetrachloride or carbon tetrabromide and the like. The solvent to be used is not particularly limited as long as it is an inert solvent, and examples thereof include aromatic hydrocarbons such as benzene, toluene, xylene and the like, halogenated hydrocarbons such as dichloromethane, chloroform, 1,2-dichloroethane and the like, and nitriles such as acetonitrile, propionitrile and the like. The reaction temperature is generally from −20° C. to the boiling point of the solvent, preferably 0° C. to 80° C. While the reaction time varies depending on the compound, it is from 1 to 24 hr.

In the reaction of halide compound (V) with imidazole or triazole in the presence of a base to give compound (I), examples of the base include alkali metal hydroxides such as lithium hydroxide, sodium hydroxide, potassium hydroxide and the like, alkaline earth metal hydroxides such as magnesium hydroxide, calcium hydroxide and the like, alkali metal carbonates such as sodium carbonate, potassium carbonate, sodium hydrogen carbonate, potassium hydrogen carbonate and the like, metal hydrides such as sodium hydride, potassium hydride and the like, organic bases such as ammonium, triethylamine, diisopropylamine, pyridine, imidazole, triazole, 1,8-diazabicyclo[5.4.0]undec-7-ene and the like, and the like. The solvent to be used is not particularly limited as long as it is an inert solvent, and examples thereof include aromatic hydrocarbons such as benzene, toluene, xylene and the like, halogenated hydrocarbons such as dichloromethane, chloroform, 1,2-dichloroethane and the like, nitriles such as acetonitrile, propionitrile and the like, ketones such as acetone and the like, ethers such as diethyl ether, tetrahydrofuran, dioxane and the like, aprotic polar solvents such as N,N-dimethylformamide, N,N-dimethylacetamide, dimethylsulfoxide and the like, and the like. The reaction temperature is generally room temperature to the boiling point of the solvent, and 20° C. to 100° C. is preferable. While the reaction time varies depending on the compound, it is from 1 to 24 hr.

In the reaction of acylhydrazine compound (IV) with thionyldiazole (VI), carbonyldiazole (VII) or compound (VIII) to give compound (I), the solvent to be used is not particularly limited as long as it is an inert solvent, and examples thereof include aromatic hydrocarbons such as benzene, toluene, xylene and the like, halogenated hydrocarbons such as dichloromethane, chloroform, 1,2-dichloroethane and the like, nitriles such as acetonitrile, propionitrile and the like, ethers such as diethyl ether, tetrahydrofuran, dioxane and the like, aprotic polar solvents such as N,N-dimethylformamide, N,N-dimethylacetamide, dimethylsulfoxide and the like, and the like. The reaction temperature is generally −20° C. to the boiling point of the solvent, and 0° C. to 80° C. is preferable. While the reaction time varies depending on the compound, it is from 1 to 24 hr.

After completion of the above-mentioned reaction, the object compound (I) can be purified by solvent extraction, recrystallization, column chromatography and the like, as necessary.

Since the compound (I) of the present invention has an imine structure, a geometric isomer having an (E) or (Z) configuration is present, and can be separated by recrystallization, column chromatography and the like.

A thermodynamically unstable isomer or a mixture thereof can be isomerized to a thermodynamically stabler isomer by heating without solvent or in an inert solvent. Examples of the inert solvent include aromatic hydrocarbons such as benzene, toluene, xylene and the like, halogenated hydrocarbons such as dichloromethane, chloroform, 1,2-dichloroethane and the like, nitriles such as acetonitrile, propionitrile and the like, ketones such as acetone and the like, ethers such as diethyl ether, tetrahydrofuran, dioxane and the like, aprotic polar solvents such as N,N-dimethylformamide, N,N-dimethylacetamide, dimethylsulfoxide and the like, and the like. The reaction temperature is 40° C. to the boiling point of the solvent. While the reaction time varies depending on the compound, it is from 1 to 24 hr.

The compound (I) of the present invention can be converted to a salt by adding a pharmacologically acceptable salt in the solvent.

The solvent to be used is not particularly limited as long as it is an inert solvent, and examples thereof include, aromatic hydrocarbons such as benzene, toluene, xylene and the like, halogenated hydrocarbons such as dichloromethane, chloroform, 1,2-dichloroethane and the like, esters such as ethyl acetate and the like, nitriles such as acetonitrile, propionitrile and the like, ketones such as acetone and the like, ethers such as diethyl ether, tetrahydrofuran, dioxane and the like, alcohols such as methanol, ethanol, isopropanol and the like, hydrocarbons such as hexane, cyclohexane and the like, and the like.

The salt to be used is not particularly limited as long as it is a pharmacologically acceptable salt, and examples thereof include inorganic acid salts such as hydrochloride, hydrobromide, nitrate, sulfate, phosphate and the like, carboxylic acid salts such as acetate, oxalate, fumarate, maleate, malonate, citrate, succinate, malate and the like, sulfonates such as methanesulfonate, benzenesulfonate, p-toluenesulfonate and the like, alkali metal salts such as lithium salt, sodium salt, potassium salt and the like, alkaline earth metal salts such as calcium salt, magnesium salt and the like, and the like.

In a first embodiment of the present invention, compound (I) shows a superior antifungal activity, and is effective for the treatment or prophylaxis of infections caused by fungi (e.g., hyphomycetes such as *Trichophyton* genus, *Microsporum* genus, *Epidermophyton* genus, *Aspergillus* genus, *Fusarium* genus and the like or blastomycetes such as *Malassezia* genus, *Candida* genus, *Cryptococcus* genus and the like), diseases (e.g., dermatophytosis, malasseziosis, candidiasis, aspergillosis, cryptococcosis and fusariosis), particularly infections and diseases developed and aggravated by fungi such as *Trichophyton* genus, *Malassezia* genus or *Candida* genus. In addition, it is effective for the treatment of dermatomycosis, onychomycosis, keratomycosis, colpomycosis, stomatomycosis, deep mycosis and the like relating to the above-mentioned fungi.

In a second embodiment of the present invention, compound (I) shows a superior anti-inflammatory activity and a superior antiallergic activity, and is effective for the treatment or prophylaxis of various inflammations and allergic diseases, for example, atopic dermatitis, seborrheic dermatitis, psoriasis, asthma, COPD, allergic rhinitis, allergic conjunctivitis, food allergy, rheumatism, acne and the like, particularly, it is effective for the treatment of diseases relating to type I, type IV inflammation or allergic reaction.

A medicament containing the compound (I) of the present invention as an active ingredient is the compound alone or a mixture of the compound and a pharmacologically acceptable liquid or solid additive carrier, for example, excipient, binder, diluent, expander, disintegrant, stabilizer, preservative, buffer, emulsifier, aromatic, colorant, sweetening agent, thickening agent, corrigent, solubilizing agents, or other additives, which can be prepared by a conventional method in the technical field.

The medicament of the present invention can be administered orally or parenterally (e.g., external application, subcutaneous administration, intravenous administration, intramuscular administration and the like) to a mammal (e.g., human, monkey, bovine, horse, swine, dog, cat, rabbit, guinea pig, rat, mouse and the like). Where necessary, other medicaments may also be blended.

For administration as an external preparation, a dosage form such as cream, lotion, liquid, nail lacquer, adhesive preparation (e.g., tape, film and the like), gel, ointment, ophthalmic ointment, suppository, vaginal suppository, powder, emulsion and the like can be formulated. For formulation, pharmaceutically acceptable ones such as a water-soluble base, an oily base, an emulsifying base and the like can be used without any particular limitation, and they can be formulated according to a conventional method in the technical field.

Examples of the water-soluble base include polyethylene glycol (macrogol), ethanol, glycerol, propylene glycol and the like.

Examples of the oily base include mineral-derived petrolatum or paraffin, Plastibase obtained by gelling a polyethylene resin with liquid paraffin, biomass-derived beeswax and the like.

Examples of the emulsifying base include lanolin and the like.

Besides these, various additives can be used as necessary. Examples of the additive include stearyl alcohol (emulsifying base), polyoxyethylene hydrogenated castor oil 60 (non-ion surfactant), glyceryl monostearate (emulsifier), coating film forming agents such as methacrylic acid alkyl ester copolymer, hydroxypropylcellulose, hydroxypropylmethylcellulose, methylcellulose, ethylcellulose, polyvinyl alcohol and the like, solvents such as ethyl acetate, butyl acetate, acetone, methyl ethyl ketone, diisopropyl adipate, diethyl sebacate, triacetine and the like, methyl parahydroxybenzoate (preservative), p-hydroxybenzoic acid (preservative) and the like.

The content of the active ingredient is preferably 0.01 to 10 wt %. The dose can be adjusted appropriately according to the size of the affected part and symptoms.

For application to the skin as an external preparation, the dose thereof varies depending on the age and symptom of patients and each condition. It is preferably about 1 to 100000 μg/cm$^2$, more preferably 10 to 10000 μg/cm$^2$, as an active ingredient for an adult for one day.

For oral administration, it is used as powder, tablet, granule, capsule or syrup, and for parenteral administration, it is used as injection such as subcutaneous, intramuscular or intravenous injection and the like, each of which can be prepared by a conventional method in the technical field using various bases and additives such as lactose, calcium carboxymethylcellulose, hydroxymethylcellulose, crystalline cellulose and the like.

The dose in this case varies depending on the age and body weight of patients and each condition. It is 10 mg to 10 g, preferably 50 mg to 5 g, as an active ingredient for an adult for one day. The administration method is administration of the above-mentioned daily dose in one to several portions.

EXAMPLES

The present invention is explained in more detail in the following by referring to Examples, which are not to be construed as limitative.

For protone nuclear magnetic resonance ($^1$H-NMR) spectrum, JNM-EX270 nuclear magnetic resonance apparatus (270 MHz, manufactured by JEOL Ltd.) or JNM-ECA400 nuclear magnetic resonance apparatus (400 MHz, manufactured by JEOL Ltd.) was used. The chemical shift of $^1$H-NMR is shown in δ (ppm) value, and TMS (tetramethylsilane) was used as an internal standard material. The following abbreviations were used. s=singlet, d=doublet, t=triplet, q=quartet, quin=quintet, sex=sextet, sep=septet, m=multiplet, br=broad.

For mass spectrum (Fast Atom Bombardment ionization method; FAB-MS), JMS-HX110A mass spectrometry apparatus (manufactured by JEOL Ltd.) was used. The measurement was performed with resolution capability 1000, primary ion Xe, positive ion, primary accelerating voltage 6 KV, secondary accelerating voltage 10 KV, matrix Magic Bullet.

Example 1

N'-[1-(2-bromophenyl)-1-imidazol-1-ylmethylidene]-N,N-dimethylhydrazine (Compound No. 1)

To a solution of 2-bromobenzoic acid (10.3 g, 51.3 mmol) in 1,2-dichloroethane (200 ml) were added oxalyl chloride (5.34 ml, 61.5 mmol) and N,N-dimethylformamide (0.1 ml), and the mixture was stirred at room temperature for 2 hr. The reaction solvent was evaporated under reduced pressure, and the residue was dissolved in 1,2-dichloroethane (200 ml). N,N-Dimethylhydrazine (3.08 g, 51.3 mmol) and N-methylmorpholine (12.4 ml, 113 mmol) were added under ice-cooling, and the mixture was stirred at room temperature for 20 hr. The reaction mixture was washed successively with 5% aqueous sodium hydrogen carbonate solution (100 ml) and water (100 ml), and the organic layer was dried over sodium sulfate. The solvent was evaporated under reduced pressure, and the obtained residue was purified by silica gel column chromatography (hexane:ethyl acetate) to give an acylhydrazine compound N',N'-dimethyl-2-bromobenzohydrazide (8.00 g, 32.9 mmol, yield 64%) as a white powder.

Imidazole (44.8 g, 658 mmol) was suspended in 1,2-dichloroethane (270 ml), thionyl chloride (12.0 ml, 165 mmol) was added, and the mixture was stirred at room temperature for 30 min. The acylhydrazine compound N',N'-dimethyl-2-bromobenzohydrazide (8.00 g, 32.9 mmol) was added thereto, and the mixture was stirred at room temperature for 24 hr, and washed with water (200 ml). The organic layer was dried over sodium sulfate and evaporated under reduced pressure, and the obtained residue was purified by silica gel column chromatography (hexane:ethyl acetate) to give the object compound (3.10 g, 10.6 mmol, yield 33%) as a yellow liquid.

$^1$H-NMR spectrum (CDCl$_3$) δppm: 2.54 (6H, s), 7.06 (1H, s), 7.24 (1H, s), 7.35-7.50 (3H, m), 7.56 (1H, s), 7.70 (1H, d, J=8.2 Hz).

Mass spectrum m/z (FAB): 293 (M$^+$+1)

Example 2

N'-[1-(2-chlorophenyl)-1-imidazol-1-ylmethylidene]-N,N-dimethylhydrazine (Compound No. 2)

In the same manner as in Example 1, the object compound was obtained as a mixture of geometric isomers (pale-yellow powder, yield from acylhydrazine compound 23%).

$^1$H-NMR spectrum (CDCl$_3$) δppm: 2.53 (6H, s), 7.06 (1H, s), 7.26 (1H, s), 7.4-7.6 (5H, m).

Mass spectrum m/z (FAB): 249 (M$^+$+1)

Example 3

N'-[1-imidazol-1-yl-1-(2-methylphenyl)methylidene]-N,N-dimethylhydrazine (Compound No. 3)

To a solution of o-toluic acid (0.877 g, 6.44 mmol) in 1,2-dichloroethane (20 ml) were added oxalyl chloride (0.67 ml, 7.73 mmol) and N,N-dimethylformamide (0.01 ml), and the mixture was stirred at room temperature for 2 hr. The reaction solvent was evaporated under reduced pressure, and the residue was dissolved in 1,2-dichloroethane (15 ml). N,N-Dimethylhydrazine (0.54 ml, 7.11 mmol) and N-methylmorpholine (0.85 ml, 7.73 mmol) were added under ice-cooling, and the mixture was stirred at room temperature for 20 hr. The reaction mixture was washed with water (20 ml), and the organic layer was dried over sodium sulfate. The solvent was evaporated under reduced pressure, and the obtained residue was purified by silica gel column chromatography (hexane:ethyl acetate) to give an acylhydrazine compound N',N'-dimethyl-2-methylbenzohydrazide (0.726 g, 4.07 mmol, yield 63%) as a white powder.

Imidazole (5.57 g, 81.8 mmol) was suspended in 1,2-dichloroethane (60 ml), thionyl chloride (1.48 ml, 20.3 mmol) was added, and the mixture was stirred at room temperature for 30 min. The acylhydrazine compound N',N'-dimethyl-2-methylbenzohydrazide (0.724 g, 4.06 mmol) was added thereto, the mixture was stirred at room temperature for 24 hr, and washed with water (50 ml). The organic layer was dried over sodium sulfate and evaporated under reduced pressure, and the obtained residue was purified by silica gel column chromatography (hexane:ethyl acetate) to give the object compound (0.823 g, 3.60 mmol, yield 89%) as a yellow liquid.

Since the compound obtained here was a thermodynamically unstable isomer, the compound was isomerized to a thermodynamically stable geometric isomer according to the following method.

Unstable isomer (0.820 g, 3.59 mmol) was dissolved in toluene (10 ml), and the mixture was heated under reflux at 110° C. for 15 hr. The solvent was evaporated under reduced pressure, and the obtained residue was purified by silica gel column chromatography (hexane:ethyl acetate) to give a thermodynamically stable object compound (0.646 g, 2.83 mmol, yield from acylhydrazine compound 70%) as a yellow liquid.

$^1$H-NMR spectrum (CDCl$_3$) δppm: 2.20 (3H, s), 2.49 (6H, s), 7.04 (1H, s), 7.25-7.32 (4H, m), 7.38-7.42 (1H, m), 7.54 (1H, s).

Mass spectrum m/z (FAB): 229 (M$^+$+1)

Example 4

N'-[1-(2-ethylphenyl)-1-imidazol-1-ylmethylidene]-N,N-dimethylhydrazine (Compound No. 4)

In the same manner as in Example 3, the object compound was obtained (yellow liquid, yield from acylhydrazine compound 74%).

$^1$H-NMR spectrum (CDCl$_3$) δppm: 1.13 (3H, t, J=7.8 Hz), 2.49 (6H, s), 2.53 (2H, q, J=7.8 Hz), 7.04 (1H, s), 7.22-7.47 (5H, m), 7.55 (1H, s).

Mass spectrum m/z (FAB): 243 (M$^+$+1)

Example 5

N'-[1-(2-hexylphenyl)-1-imidazol-1-ylmethylidene]-N,N-dimethylhydrazine (Compound No. 5)

In the same manner as in Example 9, the object compound was obtained (yellow liquid, yield from acylhydrazine compound 67%).

$^1$H-NMR spectrum (CDCl$_3$) δppm: 0.84 (3H, t, J=6.9 Hz), 1.21-1.27 (6H, m), 1.41-1.57 (2H, m), 2.49 (6H, s), 2.41-2.56 (2H, m), 7.04 (1H, s), 7.20-7.31 (3H, m), 7.35 (1H, d, J=7.3 Hz), 7.41-7.45 (1H, m), 7.55 (1H, s).

Mass spectrum m/z (FAB): 299 (M$^+$+1)

Example 6

N'-[1-imidazol-1-yl-1-(2-phenethylphenyl)methylidene]-N,N-dimethylhydrazine (Compound No. 6)

In the same manner as in Example 9, the object compound was obtained (yellow liquid, yield from acylhydrazine compound 58%).

$^1$H-NMR spectrum (CDCl$_3$) δppm: 2.49 (6H, s), 2.80-2.89 (4H, m), 7.00-7.09 (3H, m), 7.15-7.47 (8H, m), 7.53 (1H, s).

Mass spectrum m/z (FAB): 319 (M$^+$+1)

Example 7

N'-[1-imidazol-1-yl-1-(2-trifluoromethylphenyl)methylidene]-N,N-dimethylhydrazine (Compound No. 7)

In the same manner as in Example 3, the object compound was obtained (yellow liquid, yield from acylhydrazine compound 21%).

$^1$H-NMR spectrum (CDCl$_3$) δppm: 2.46 (6H, s), 7.05 (1H, s), 7.25 (1H, s), 7.46 (2H, d, J=7.3 Hz), 7.51 (1H, s), 7.67-7.70 (2H, m), 7.81-7.83 (1H, m).

Mass spectrum m/z (FAB): 283 (M$^+$+1)

Example 8

N'-[1-imidazol-1-yl-1-(2-phenoxymethylphenyl)methylidene]-N,N-dimethylhydrazine (Compound No. 8)

In the same manner as in Example 1, the object compound was obtained (yellow liquid, yield from acylhydrazine compound 78%).

$^1$H-NMR spectrum (CDCl$_3$) δppm: 2.47 (6H, s), 5.14 (2H, s), 6.84 (2H, d, J=8.2 Hz), 6.90-6.97 (1H, m), 7.11 (1H, s), 7.20-7.67 (7H, m), 7.93 (1H, s).

Mass spectrum m/z (FAB): 321 (M$^+$+1)

Example 9

N'-[1-imidazol-1-yl-1-[2-(3-phenoxypropyl)phenyl]methylidene]-N,N-dimethylhydrazine (Compound No. 9)

To a solution of methyl 2-bromobenzoate (0.206 g, 0.96 mmol) in acetonitrile (3 ml) were added allyl phenyl ether (0.65 ml, 1.09 mmol), tri-o-tolylphosphine (0.014 g, 0.045 mmol), palladium acetate (0.006 g, 0.027 mmol) and triethylamine (0.16 ml, 1.15 mmol), and the mixture was stirred at 100° C. for 4 hr. The reaction mixture was filtered through celite, and ethyl acetate was added to the filtrate. The mixture was washed with water, and the organic layer was dried over sodium sulfate. The solvent was evaporated under reduced pressure, and the obtained residue was purified by silica gel column chromatography (hexane:ethyl acetate) to give methyl 2-(3-phenoxypropenyl)benzoate (0.037 g, 0.14 mmol, yield 15%).

The thus-obtained methyl 2-(3-phenoxypropenyl)benzoate (0.261 g, 0.972 mmol) was dissolved in methanol (6 ml), 10% palladium carbon (0.022 g) was added, and a hydrogenation reaction was performed at room temperature for 24 hr. The reaction mixture was filtered through celite, the filtrate was concentrated under reduced pressure, and the obtained residue was purified by silica gel column chromatography (hexane:ethyl acetate) to give methyl 2-(3-phenoxypropyl)benzoate (0.144 g, 0.533 mmol, yield 55%).

The thus-obtained methyl 2-(3-phenoxypropyl)benzoate (0.211 g, 0.781 mmol) was dissolved in methanol (3 ml), 1N-aqueous sodium hydroxide solution (4 ml) was added at room temperature, and the mixture was stirred at 60° C. for 6 hr. The reaction mixture was concentrated under reduced pressure and neutralized with 1N-aqueous hydrochloric acid solution, and the precipitated crystals were collected by filtration to give a carboxylic acid compound 2-(3-phenoxypropyl)benzoic acid (0.177 g, 0.691 mmol, yield 88%).

Using the obtained carboxylic acid compound and in the same manner as in Example 3, the object compound was obtained (yellow liquid, yield from acylhydrazine compound 27%).

$^1$H-NMR spectrum (CDCl$_3$) δppm: 1.90-2.05 (2H, m), 2.49 (6H, s), 2.72 (2H, t, J=8.2 Hz), 3.84-3.93 (2H, m), 6.83 (2H, d, J=7.8 Hz), 6.93 (1H, t, J=7.3 Hz), 7.04 (1H, s), 7.24-7.34 (5H, m), 7.38-7.47 (2H, m), 7.57 (1H, s).

Mass spectrum m/z (FAB): 349 (M$^+$+1)

Example 10

N'-[1-[2-((E)-3-benzyloxypropenyl)phenyl]-1-imidazol-1-ylmethylidene]-N,N-dimethylhydrazine
(Compound No. 10)

Methyl 2-(3-phenoxypropenyl)benzoate (0.320 g, 1.13 mmol) obtained in Example 9 was dissolved in methanol (4 ml), 1N-aqueous sodium hydroxide solution (4 ml) was added at room temperature, and the mixture was stirred at 60° C. for 3 hr. The reaction mixture was concentrated under reduced pressure and neutralized with 1N-aqueous hydrochloric acid solution, and the mixture was extracted with ethyl acetate. The extract was dried over sodium sulfate, and the solvent was evaporated under reduced pressure to give a carboxylic acid compound 2-(3-phenoxypropenyl)benzoic acid (0.302 g, 1.12 mmol, yield 99%). Using the obtained carboxylic acid compound and in the same manner as in Example 3, the object compound was obtained (yellow liquid, yield from acylhydrazine compound 9%).

$^1$H-NMR spectrum (CDCl$_3$) δppm: 2.49 (6H, s), 4.09-4.11 (2H, m), 4.45 (2H, s), 6.30-6.37 (1H, m), 6.46 (1H, d, J=16.0 Hz), 7.03 (1H, s), 7.25-7.39 (6H, m), 7.47 (1H, t, J=8.2 Hz), 7.54 (1H, s), 7.68 (1H, d, J=8.2 Hz).

Mass spectrum m/z (FAB): 361 (M$^+$+1)

Example 11

N'-[1-imidazol-1-yl-1-(2-phenylthiomethylphenyl)methylidene]-N,N-dimethylhydrazine
(Compound No. 11)

In the same manner as in Example 1, the object compound was obtained (yellow liquid, yield from acylhydrazine compound 76%).

$^1$H-NMR spectrum (CDCl$_3$) δppm: 2.48 (6H, s), 4.06 (2H, d, J=14.2 Hz), 4.19 (2H, d, J=14.2 Hz), 7.02 (1H, s), 7.1-7.5 (10H, m), 7.54 (1H, s).

Mass spectrum m/z (FAB): 337 (M$^+$+1)

Example 12

N'-[1-(2-benzoylphenyl)-1-imidazol-1-ylmethylidene]-N,N-dimethylhydrazine
(Compound No. 12)

In the same manner as in Example 1, the object compound was obtained (white powder, yield from acylhydrazine compound 69%).

$^1$H-NMR spectrum (CDCl$_3$) δppm: 2.38 (3H, br s), 2.99 (3H, br s), 6.90 (1H, s), 7.09 (1H, s), 7.19-7.21 (1H, m), 7.40-7.41 (5H, m), 7.54-7.56 (2H, m), 7.16 (1H, s), 7.87-7.89 (1H, m).

Mass spectrum m/z (FAB): 319 (M$^+$+1)

Example 13

N'-[1-(2-hydroxyphenyl)-1-imidazol-1-ylmethylidene]-N,N-dimethylhydrazine
(Compound No. 13)

The Compound No. 14 (0.190 g, 0.70 mmol) obtained in Example 14 was dissolved in methanol (1.5 ml), sodium methoxide (0.038 g, 0.70 mmol) was added, and the mixture was stirred at room temperature for 20 hr. The reaction mixture was concentrated under reduced pressure. The residue was dissolved in ethyl acetate, and the mixture was washed with water and dried over sodium sulfate. The solvent was evaporated under reduced pressure, and the obtained residue was purified by silica gel column chromatography (hexane:ethyl acetate) to give the object compound (0.114 g, 0.50 mmol, yield 71%) as a yellow liquid.

$^1$H-NMR spectrum (CDCl$_3$) δppm: 2.68 (6H, s), 6.91 (1H, td, J=6.9, 0.9 Hz), 7.07-7.11 (3H, m), 7.18 (1H, t, J=1.4 Hz), 7.48 (1H, td, J=6.9, 1.4 Hz), 7.80 (1H, s), 11.60 (1H, s).

Mass spectrum m/z (FAB): 231 (M$^+$+1)

Example 14

N'-[1-(2-acetoxyphenyl)-1-imidazol-1-ylmethylidene]-N,N-dimethylhydrazine
(Compound No. 14)

In the same manner as in Example 1, the object compound was obtained (yellow liquid, yield from acylhydrazine compound 33%).

$^1$H-NMR spectrum (CDCl$_3$) δppm: 2.12 (3H, s), 2.55 (6H, s), 7.10 (1H, s), 7.16 (1H, s), 7.25-7.4 (2H, m), 7.41 (1H, dd, J=7.3, 1.8 Hz), 7.55 (1H, td, J=7.3, 1.8 Hz), 7.87 (1H, s).

Mass spectrum m/z (FAB): 273 (M$^+$+1)

Example 15

N'-[1-imidazol-1-yl-1-(2-methoxyphenyl)methylidene]-N,N-dimethylhydrazine
(Compound No. 15)

In the same manner as in Example 3, the object compound was obtained (yellow liquid, yield from acylhydrazine compound 38%).

$^1$H-NMR spectrum (CDCl$_3$) δppm: 2.49 (6H, s), 3.76 (3H, s), 7.00-7.09 (3H, m), 7.31-7.33 (2H, m), 7.48 (1H, t, J=7.3 Hz), 7.55 (1H, s).

Mass spectrum m/z (FAB): 245 (M$^+$+1)

Example 16

N'-[1-(2-ethoxyphenyl)-1-imidazol-1-ylmethylidene]-N,N-dimethylhydrazine
(Compound No. 16)

In the same manner as in Example 3, the object compound was obtained (white crystal, yield from acylhydrazine compound 12%).

¹H-NMR spectrum (CDCl₃) δppm: 1.19 (3H, t, J=6.9 Hz), 2.50 (6H, s), 3.99 (2H, br s), 6.97-7.07 (3H, m), 7.29 (1H, s), 7.34 (1H, dd, J=7.3, 1.4 Hz), 7.42-7.47 (1H, m), 7.56 (1H, s).
Mass spectrum m/z (FAB): 259 (M⁺+1)

Example 17

N'-[1-imidazol-1-yl-1-(2-propoxyphenyl)methylidene]-N,N-dimethylhydrazine
(Compound No. 17)

In the same manner as in Example 3, the object compound was obtained (yellow liquid, yield from acylhydrazine compound 62%).
¹H-NMR spectrum (CDCl₃) δppm: 0.80 (3H, t, J=7.3 Hz), 1.59 (2H, sex, J=7.3 Hz), 2.49 (6H, s), 3.87 (2H, br s), 6.96-7.07 (3H, m), 7.28 (1H, s), 7.34 (1H, dd, J=7.8, 1.4 Hz), 7.42-7.47 (1H, m), 7.55 (1H, s).
Mass spectrum m/z (FAB): 273 (M⁺+1)

Example 18

N,N-dimethyl-N'-[1-(2-propoxyphenyl)-1-(1,2,4-triazol-1-yl)methylidene]hydrazine
(Compound No. 18)

To a solution of 2-propoxybenzoic acid (10.0 g, 55.5 mmol) in 1,2-dichloroethane (80 ml) were added oxalyl chloride (5.81 ml, 66.6 mmol) and N,N-dimethylformamide (0.1 ml), and the mixture was stirred at room temperature for 3 hr. The reaction solvent was evaporated under reduced pressure, and the residue was dissolved in 1,2-dichloroethane (200 ml), N,N-dimethylhydrazine (5.16 ml, 66.6 mmol) and N-methylmorpholine (7.32 ml, 66.6 mmol) were added under ice-cooling, and the mixture was stirred at room temperature for 20 hr. The reaction mixture was washed with water (100 ml), and the organic layer was dried over sodium sulfate. The solvent was evaporated under reduced pressure, and the obtained residue was purified by silica gel column chromatography (hexane:ethyl acetate) to give an acylhydrazine compound N',N'-dimethyl-2-propoxybenzohydrazide (10.77 g, 48.5 mmol, yield 87%) as a white powder.
The obtained acylhydrazine compound N',N'-dimethyl-2-propoxybenzohydrazide (0.40 g, 1.8 mmol) was dissolved in toluene (1 ml), phosphorus oxychloride (1 ml) was added, and the mixture was stirred at 60° C. for 3 hr. The reaction solvent was evaporated under reduced pressure, triazole (0.62 g, 9.0 mmol) and triethylamine (0.75 ml, 5.4 mmol) were added to a solution of the residue in 1,2-dichloroethane (10 ml), and the mixture was stirred at 60 to 70° C. for 3 hr. The reaction mixture was washed with water (30 ml), and the organic layer was dried over sodium sulfate and evaporated under reduced pressure. The residue was purified by silica gel column chromatography (hexane:ethyl acetate) to give the object compound (0.10 g, 0.37 mmol, yield 21%) as a yellow liquid.
¹H-NMR spectrum (CDCl₃) δppm: 0.78 (3H, t, J=7.3 Hz), 1.53 (2H, sex, J=7.3 Hz), 2.63 (6H, s), 3.84 (2H, br t, J=6.4 Hz), 6.95 (1H, d, J=8.2 Hz), 7.05 (1H, t, J=8.2 Hz), 7.41-7.47 (2H, m), 7.89 (1H, s), 8.51 (1H, s).
Mass spectrum m/z (FAB): 274 (M⁺+1)

Example 19

N'-[1-imidazol-1-yl-1-(2-isopropoxyphenyl)methylidene]-N,N-dimethylhydrazine
(Compound No. 19)

In the same manner as in Example 36, a carboxylic acid compound 2-isopropoxybenzoic acid was obtained. Then, in the same manner as in Example 3, the object compound was obtained (yellow liquid, yield from acylhydrazine compound 32%).
¹H-NMR spectrum (CDCl₃) δppm: 1.15 (6H, br s), 2.50 (6H, s), 4.53 (1H, quin, J=6.0 Hz), 6.94-7.06 (3H, m), 7.25 (1H, s), 7.34 (1H, dd, J=7.3, 1.4 Hz), 7.41-7.45 (1H, m), 7.56 (1H, s).
Mass spectrum m/z (FAB): 273 (M⁺+1)

Example 20

N'-[1-(2-allyloxyphenyl)-1-imidazol-1-ylmethylidene]-N,N-dimethylhydrazine
(Compound No. 20)

In the same manner as in Example 36, a carboxylic acid compound 2-allyloxybenzoic acid was obtained. Then, in the same manner as in Example 3, the object compound was obtained (yellow liquid, yield from acylhydrazine compound 22%).
¹H-NMR spectrum (CDCl₃) δppm: 2.50 (6H, s), 4.50 (2H, d, J=5.0 Hz), 5.17 (1H, dd, J=10.5, 1.4 Hz), 5.21 (1H, dd, J=17.4, 1.4 Hz), 5.81 (1H, ddt, J=17.4, 10.5, 5.0 Hz), 6.99 (1H, d, J=8.2 Hz), 7.02 (1H, s), 7.05-7.09 (1H, m), 7.30 (1H, s), 7.33-7.36 (1H, m), 7.42-7.47 (1H, m), 7.57 (1H, s).
Mass spectrum m/z (FAB): 271 (M⁺+1)

Example 21

N'-[1-imidazol-1-yl-1-(2-(Z)-propenyloxyphenyl)methylidene]-N,N-dimethylhydrazine
(Compound No. 21)

In the same manner as in Example 3, the object compound was obtained (pale-yellow powder, yield from acylhydrazine compound 4%).
¹H-NMR spectrum (CDCl₃) δppm: 1.47 (3H, dd, J=6.9, 1.8 Hz), 2.51 (6H, s), 4.88 (1H, qd, J=6.9, 0.9 Hz), 6.30-6.33 (1H, m), 7.03 (1H, s), 7.07 (1H, d, J=8.2 Hz), 7.13-7.18 (1H, m), 7.30 (1H, s), 7.38 (1H, dd, J=7.3, 1.8 Hz), 7.45-7.49 (1H, m), 7.62 (1H, s)
Mass spectrum m/z (FAB): 271 (M⁺+1)

Example 22

N'-[1-imidazol-1-yl-1-(2-propynyloxyphenyl)methylidene]-N,N-dimethylhydrazine
(Compound No. 22)

In the same manner as in Example 36, a carboxylic acid compound 2-propynyloxybenzoic acid was obtained. Then, in the same manner as in Example 3, the object compound was obtained (yellow liquid, yield from acylhydrazine compound 56%).
¹H-NMR spectrum (CDCl₃) δppm: 2.50 (6H, s), 4.67 (2H, d, J=2.3 Hz), 7.02 (1H, s), 7.12 (1H, td, J=7.3, 0.9 Hz), 7.16 (1H, d, J=8.2 Hz), 7.31-7.35 (3H, m), 7.47-7.52 (1H, m), 7.56 (1H, s).
Mass spectrum m/z (FAB): 269 (M⁺+1)

Example 23

N'-[1-(2-butoxyphenyl)-1-imidazol-1-ylmethylidene]-N,N-dimethylhydrazine
(Compound No. 23)

In the same manner as in Example 3, the object compound was obtained (yellow liquid, yield from acylhydrazine compound 15%).

¹H-NMR spectrum (CDCl₃) δppm: 0.84 (3H, t, J=7.3 Hz), 1.23 (2H, sex, J=7.3 Hz), 1.51-1.58 (2H, m), 2.49 (6H, s), 3.91 (2H, br s), 6.96-7.07 (3H, m), 7.28 (1H, s), 7.34 (1H, dd, J=7.3, 1.8 Hz), 7.42-7.47 (1H, m), 7.55 (1H, s).
Mass spectrum m/z (FAB): 287 (M⁺+1)

Example 24

N'-[1-imidazol-1-yl-1-(2-pentyloxyphenyl)methylidene]-N,N-dimethylhydrazine (Compound No. 24)

In the same manner as in Example 3, the object compound was obtained (yellow liquid, yield from acylhydrazine compound 34%).
¹H-NMR spectrum (CDCl₃) δppm: 0.84 (3H, t, J=6.9 Hz), 1.12-1.3 (4H, m), 1.56 (2H, quin, J=6.9 Hz), 2.49 (6H, s), 3.90 (2H, br s), 6.97 (1H, d, J=8.2 Hz), 7.01 (1H, s), 7.04 (1H, td, J=7.3, 0.9 Hz), 7.28 (1H, s), 7.34 (1H, dd, J=7.8, 1.8 Hz), 7.44 (1H, td, J=7.8, 1.8 Hz), 7.54 (1H, s).
Mass spectrum m/z (FAB): 301 (M⁺+1)

Example 25

N'-[1-(3-fluoro-6-pentyloxyphenyl)-1-imidazol-1-ylmethylidene]-N,N-dimethylhydrazine (Compound No. 25)

In the same manner as in Example 36, a carboxylic acid compound 3-fluoro-6-pentyloxybenzoic acid was obtained. Then, in the same manner as in Example 3, the object compound was obtained (yellow liquid, yield from acylhydrazine compound 3%).
¹H-NMR spectrum (CDCl₃) δppm: 0.84 (3H, t, J=7.3 Hz), 1.12-1.27 (4H, m), 1.51-1.58 (2H, m), 2.50 (6H, s), 3.86 (2H, br s), 6.90-6.93 (1H, m), 7.02 (1H, s), 7.08-7.17 (2H, m), 7.26 (1H, s), 7.56 (1H, s).
Mass spectrum m/z (FAB): 319 (M⁺+1)

Example 26

N'-[1-imidazol-1-yl-1-(3-pentyloxyphenyl)methylidene]-N,N-dimethylhydrazine (Compound No. 26)

In the same manner as in Example 36, a carboxylic acid compound 3-pentyloxybenzoic acid was obtained. Then, in the same manner as in Example 1, the object compound was obtained as a mixture of geometric isomers (yellow liquid, yield from acylhydrazine compound 32%).
¹H-NMR spectrum (CDCl₃) δppm: 0.91-0.95 (3H, m), 1.35-1.44 (4H, m), 1.73-1.79 (2H, m), 2.51, 2.57 (6H, s each), 3.92-3.97 (2H, m), 6.86-7.05 (3H, m), 7.15-7.24 (3H, m), 7.66, 7.73 (1H, s each).
Mass spectrum m/z (FAB): 301 (M⁺+1)

Example 27

N'-[1-imidazol-1-yl-1-(4-pentyloxyphenyl)methylidene]-N,N-dimethylhydrazine (Compound No. 27)

In the same manner as in Example 36, a carboxylic acid compound 4-pentyloxybenzoic acid was obtained. Then, in the same manner as in Example 1, the object compound was obtained as a mixture of geometric isomers (pale-yellow powder, yield from acylhydrazine compound 47%).
¹H-NMR spectrum (CDCl₃) δppm: 0.91-0.97 (3H, m), 1.33-1.50 (4H, m), 1.75-1.86 (2H, m), 2.49, 2.50 (6H, s each), 3.95-4.03 (2H, m), 6.85, 6.96 (2H, d each, J=8.7 Hz), 7.05-7.19 (2H, m), 7.33, 7.45 (2H, d each, J=8.7 Hz), 7.69, 7.76 (1H, s each).
Mass spectrum m/z (FAB): 301 (M⁺+1)

Example 28

N'-[1-(2-hexyloxyphenyl)-1-imidazol-1-ylmethylidene]-N,N-dimethylhydrazine (Compound No. 28)

In the same manner as in Example 3, the object compound was obtained (yellow liquid, yield from acylhydrazine compound 58%).
¹H-NMR spectrum (CDCl₃) δppm: 0.86 (3H, t, J=6.9 Hz), 1.16-1.3 (6H, m), 1.55 (2H, quin, J=6.9 Hz), 2.49 (6H, s), 3.90 (2H, br s), 6.97 (1H, d, J=8.2 Hz), 7.00 (1H, s), 7.04 (1H, t, J=7.8 Hz), 7.28 (1H, s), 7.34 (1H, dd, J=7.8, 1.8 Hz), 7.44 (1H, t, J=7.8 Hz), 7.54 (1H, s).
Mass spectrum m/z (FAB): 315 (M⁺+1)

Example 29

N'-[1-imidazol-1-yl-1-(2-propoxymethoxyphenyl)methylidene]-N,N-dimethylhydrazine (Compound No. 29)

To a solution of methyl salicylate (0.637 g, 4.19 mmol) in N,N-dimethylformamide (8 ml) were added chloromethyl propyl ether (0.50 ml, 4.54 mmol) and potassium carbonate (0.755 g, 5.46 mmol), and the mixture was stirred at room temperature for 20 hr. Ethyl acetate was added to the reaction mixture, the mixture was washed with water, and the organic layer was dried over sodium sulfate. The solvent was evaporated under reduced pressure, and the obtained residue was purified by silica gel column chromatography (hexane:ethyl acetate) to give methyl 2-propoxymethoxybenzoate (0.414 g, 1.85 mmol, yield 44%). This was dissolved in methanol (5 ml), 1N-aqueous sodium hydroxide solution (5 ml) was added at room temperature, and the mixture was stirred at room temperature for 20 hr. The reaction mixture was concentrated under reduced pressure and neutralized with 5% aqueous citric acid solution, and the mixture was extracted with ethyl acetate. The extract was dried over sodium sulfate, and the solvent was evaporated under reduced pressure to give a carboxylic acid compound 2-propoxymethoxybenzoic acid (0.374 g, 1.78 mmol, yield 96%).
Using the obtained carboxylic acid compound and in the same manner as in Example 1, the object compound was obtained as a mixture of geometric isomers (pale-yellow powder, yield from acylhydrazine compound 56%).
¹H-NMR spectrum (CDCl₃) δppm: 0.83-0.87 (3H, m), 1.46-1.88 (2H, m), 2.53, 2.57 (6H, s each), 3.35, 3.43 (2H, t each, J=6.9 Hz), 4.99, 5.15 (2H, s each), 7.03-7.16 (2H, m), 7.29-7.48 (5H, m), 7.66, 7.96 (1H, br s each).
Mass spectrum m/z (FAB): 303 (M⁺+1)

Example 30

N'-[1-(2-ethoxyethoxyphenyl)-1-imidazol-1-ylmethylidene]-N,N-dimethylhydrazine (Compound No. 30)

In the same manner as in Example 29, the object compound was obtained as a mixture of geometric isomers (yellow liquid, yield from acylhydrazine compound 57%).

$^1$H-NMR spectrum (CDCl$_3$) δppm: 1.12-1.19 (3H, m), 2.50, 2.55 (6H, each), 3.39-3.56 (4H, m), 3.92, 4.22 (2H, t each, J=6.0 Hz), 6.86-7.09 (3H, m), 7.34-7.47 (3H, m), 7.58, 7.90 (1H, br s each).

Mass spectrum m/z (FAB): 303 (M$^+$+1)

Example 31

N'-[1-[2-(3-cyanopropoxy)phenyl]-1-imidazol-1-ylmethylidene]-N,N-dimethylhydrazine
(Compound No. 31)

In the same manner as in Example 29, the object compound was obtained (pale-yellow powder, yield from acylhydrazine compound 5%).

$^1$H-NMR spectrum (CDCl$_3$) δppm: 1.81 (2H, quin, J=7 Hz), 2.17 (2H, t, J=7 Hz), 2.57 (6H, s), 3.91 (2H, t, J=6 Hz), 6.86 (1H, d, J=8 Hz), 7.0-7.15 (2H, m), 7.4-7.45 (2H, m), 7.50 (1H, dd, J=8, 2 Hz), 7.90 (1H,s).

Mass spectrum m/z (FAB): 298 (M$^+$+1)

Example 32

N'-[1-imidazol-1-yl-1-(2-trifluoromethoxyphenyl)methylidene]-N,N-dimethylhydrazine
(Compound No. 32)

In the same manner as in Example 3, the object compound was obtained (yellow liquid, yield from acylhydrazine compound 9%).

$^1$H-NMR spectrum (CDCl$_3$) δppm: 2.49 (6H, s), 7.06 (1H, s), 7.26 (1H, s), 7.38-7.45 (3H, m), 7.55-7.60 (1H, m), 7.61 (1H, s).

Mass spectrum m/z (FAB): 299 (M$^+$+1)

Example 33

N'-[1-imidazol-1-yl-1-[2-(1,1,2,2-tetrafluoroethoxy)phenyl]methylidene]-N,N-dimethylhydrazine
(Compound No. 33)

In the same manner as in Example 3, the object compound was obtained (yellow liquid, yield from acylhydrazine compound 31%).

$^1$H-NMR spectrum (CDCl$_3$) δppm: 2.49 (6H, s), 5.61 (1H, tt, J=53.1, 2.8 Hz), 7.05 (1H, s), 7.21 (1H, s), 7.38-7.42 (1H, m), 7.46-7.48 (2H, m), 7.54-7.58 (1H, m), 7.61 (1H, s).

Mass spectrum m/z (FAB): 331 (M$^+$+1)

Example 34

N'-[1-(2-benzyloxyphenyl)-1-imidazol-1-ylmethylidene]-N,N-dimethylhydrazine
(Compound No. 34)

In the same manner as in Example 1, the object compound was obtained (yellow liquid, yield from acylhydrazine compound 90%).

$^1$H-NMR spectrum (CDCl$_3$) δppm: 2.50 (6H, s), 5.04 (2H, s), 7.00-7.14 (5H, m), 7.24-7.34 (4H, m), 7.37 (1H, d, J=7.8 Hz), 7.44 (1H, t, J=7.8 Hz), 7.61 (1H, s).

Mass spectrum m/z (FAB): 321 (M$^+$+1)

Example 35

N'-[1-[2-(4-fluorobenzyloxy)phenyl]-1-imidazol-1-ylmethylidene]-N,N-dimethylhydrazine
(Compound No. 35)

In the same manner as in Example 3, the object compound was obtained (yellow liquid, yield from acylhydrazine compound 68%).

$^1$H-NMR spectrum (CDCl$_3$) δppm: 2.49 (6H, s), 4.98 (2H, s), 6.95-7.12 (7H, m), 7.28 (1H, t, J=1.4 Hz), 7.38 (1H, dd, J=7.8, 1.4 Hz), 7.45 (1H, td, J=7.8, 1.4 Hz), 7.58 (1H, s).

Mass spectrum m/z (FAB): 339 (M$^+$+1)

Example 36

N'-[1-[2-(3-fluorobenzyloxy)phenyl]-1-imidazol-1-ylmethylidene]-N,N-dimethylhydrazine
(Compound No. 36)

To a solution of methyl salicylate (1.512 g, 9.93 mmol) in N,N-dimethylformamide (15 ml) were added 3-fluorobenzyl bromide (1.3 ml, 10.6 mmol) and potassium carbonate (1.780 g, 12.88 mmol), and the mixture was stirred at 80° C. for 5 hr. Ethyl acetate was added to the reaction mixture, the mixture was washed with water, and the organic layer was dried over sodium sulfate. The solvent was evaporated under reduced pressure, and the obtained residue was purified by silica gel column chromatography (hexane:ethyl acetate) to give methyl 2-(3-fluorobenzyloxy)benzoate (1.991 g, 7.65 mmol, yield 77%). This was dissolved in methanol (15 ml), 1N-aqueous sodium hydroxide solution (15 ml) was added at room temperature, and the mixture was stirred at 60° C. for 5 hr. The reaction mixture was concentrated under reduced pressure and neutralized with 1N-aqueous hydrochloric acid solution, and the mixture was extracted with ethyl acetate. The extract was dried over sodium sulfate, and the solvent was evaporated under reduced pressure to give a carboxylic acid compound 2-(3-fluorobenzyloxy)benzoic acid (1.790 g, 7.27 mmol, yield 95%).

Using the obtained carboxylic acid compound and in the same manner as in Example 3, the object compound was obtained (yellow liquid, yield from acylhydrazine compound 33%).

$^1$H-NMR spectrum (CDCl$_3$) δppm: 2.51 (6H, s), 5.03 (2H, s), 6.87-7.12 (7H, m), 7.24-7.31 (1H, m), 7.38 (1H, dd, J=7.8, 1.4 Hz), 7.43-7.47 (1H, m), 7.59 (1H, s).

Mass spectrum m/z (FAB): 339 (M$^+$+1)

Example 37

N'-[1-[2-(2-fluorobenzyloxy)phenyl]-1-imidazol-1-ylmethylidene]-N,N-dimethylhydrazine
(Compound No. 37)

In the same manner as in Example 36, carboxylic acid compound 2-(2-fluorobenzyloxy)benzoic acid was obtained. Then, in the same manner as in Example 3, the object compound was obtained (yellow liquid, yield from acylhydrazine compound 60%).

$^1$H-NMR spectrum (CDCl$_3$) δppm: 2.49 (6H, s), 5.11 (2H, s), 6.96-7.14 (6H, m), 7.22-7.30 (2H, m), 7.37 (1H, dd, J=7.8, 1.8 Hz), 7.47 (1H, t, J=8.7 Hz), 7.60 (1H, s).

Mass spectrum m/z (FAB): 339 (M$^+$+1)

Example 38

N'-[1-[2-(4-chlorobenzyloxy)phenyl]-1-imidazol-1-ylmethylidene]-N,N-dimethylhydrazine
(Compound No. 38)

In the same manner as in Example 3, the object compound was obtained (yellow liquid, yield from acylhydrazine compound 66%).

$^1$H-NMR spectrum (CDCl$_3$) δppm: 2.49 (6H, s), 4.99 (2H, s), 7.0-7.05 (4H, m), 7.10 (1H, t, J=7.3 Hz), 7.25-7.3 (3H, m), 7.38 (1H, dd, J=7.8, 1.8 Hz), 7.46 (1H, td, J=7.8, 1.8 Hz), 7.58 (1H, s).

Mass spectrum m/z (FAB): 355 (M$^+$+1)

Example 39

N'-[1-[2-(4-chlorobenzyloxy)phenyl]-1-(1,2,4-triazol-1-yl)methylidene]-N,N-dimethylhydrazine
(Compound No. 39)

In the same manner as in Example 18, the object compound was obtained (pale-yellow powder, yield from acylhydrazine compound 81%).

$^1$H-NMR spectrum (CDCl$_3$) δppm: 2.63 (6H, s), 4.96 (2H, s), 6.98-7.03 (3H, m), 7.10 (1H, t, J=7.3 Hz), 7.28 (2H, d, J=7.3 Hz), 7.46 (2H, d, J=7.3 Hz), 7.91 (1H, s), 8.54 (1H, s).

Mass spectrum m/z (FAB): 356 (M$^+$+1)

Example 40

N'-[1-[2-(3-chlorobenzyloxy)phenyl]-1-imidazol-1-ylmethylidene]-N,N-dimethylhydrazine
(Compound No. 40)

In the same manner as in Example 3, the object compound was obtained (yellow liquid, yield from acylhydrazine compound 22%).

$^1$H-NMR spectrum (CDCl$_3$) δppm: 2.51 (6H, s), 5.01 (2H, s), 6.96-7.03 (2H, m), 7.06 (1H, s), 7.10 (1H, t, J=7.3 Hz), 7.18 (1H, s), 7.22-7.26 (2H, m), 7.31 (1H, s), 7.38 (1H, dd, J=7.8, 1.8 Hz), 7.45 (1H, td, J=7.8, 1.8 Hz), 7.59 (1H, s).

Mass spectrum m/z (FAB): 355 (M$^+$+1)

Example 41

N'-[1-[2-(2-chlorobenzyloxy)phenyl]-1-imidazol-1-ylmethylidene]-N,N-dimethylhydrazine
(Compound No. 41)

In the same manner as in Example 3, the object compound was obtained (yellow liquid, yield from acylhydrazine compound 52%).

$^1$H-NMR spectrum (CDCl$_3$) δppm: 2.50 (6H, s), 5.14 (2H, s), 7.03 (1H, s), 7.04-7.13 (3H, m), 7.16-7.24 (2H, m), 7.3-7.35 (2H, m), 7.38 (1H, d, J=7.8 Hz), 7.47 (1H, t, J=7.8 Hz), 7.63 (1H, s).

Mass spectrum m/z (FAB): 355 (M$^+$+1)

Example 42

N'-(1-[2-(2,4-difluorobenzyloxy)phenyl-1-imidazol-1-ylmethylidene]-N,N-dimethylhydrazine
(Compound No. 42)

In the same manner as in Example 36, carboxylic acid compound 2-(2,4-difluorobenzyloxy)benzoic acid was obtained. Then, in the same manner as in Example 3, the object compound was obtained (yellow liquid, yield from acylhydrazine compound 25%).

$^1$H-NMR spectrum (CDCl$_3$) δppm: 2.49 (6H, s), 5.05 (2H, s), 6.79 (2H, q, J=7.8 Hz), 6.97-7.13 (5H, m), 7.38 (1H, dd, J=7.8, 1.8 Hz), 7.48 (1H, td, J=7.8, 1.8 Hz), 7.58 (1H, s).

Mass spectrum m/z (FAB): 357 (M$^+$+1)

Example 43

N'-[1-[2-(2,4-dichlorobenzyloxy)phenyl]-1-imidazol-1-ylmethylidene]-N,N-dimethylhydrazine
(Compound No. 43)

In the same manner as in Example 3, the object compound was obtained (pale-yellow powder, yield from acylhydrazine compound 59%).

$^1$H-NMR spectrum (CDCl$_3$) δppm: 2.50 (6H, s), 5.09 (2H, s), 6.99-7.07 (3H, m), 7.13 (1H, t, J=7.3 Hz), 7.18 (1H, dd, J=8.2, 2.3 Hz), 7.31 (1H, s), 7.36 (1H, d, J=2.3 Hz), 7.40 (1H, dd, J=7.8, 1.8 Hz), 7.48 (1H, td, J=7.8, 1.8 Hz), 7.60 (1H, s).

Mass spectrum m/z (FAB): 389 (M$^+$+1)

Example 44

N'-[1-[2-(2-fluoro-3-methylbenzyloxy)phenyl]-1-imidazol-1-ylmethylidene]-N,N-dimthylhydrazine
(Compound No. 44)

In the same manner as in Example 36, carboxylic acid compound 2-(2-fluoro-3-methylbenzyloxy)benzoic acid was obtained. Then, in the same manner as in Example 3, the object compound was obtained (yellow liquid, yield from acylhydrazine compound 24%).

$^1$H-NMR spectrum (CDCl$_3$) δppm: 2.26 (3H, d, J=2.3 Hz), 2.49 (6H, s), 5.10 (2H, s), 6.88 (1H, t, J=6.4 Hz), 6.95 (1H, t, J=7.8 Hz), 7.02 (1H, s), 7.07-7.11 (3H, m), 7.27 (1H, s), 7.36 (1H, dd, J=7.8, 1.8 Hz), 7.46 (1H, td, J=7.8, 1.8 Hz), 7.59 (1H, s).

Mass spectrum m/z (FAB): 353 (M$^+$+1)

Example 45

N'-[1-imidazol-1-yl-1-[2-(2,3,4,5,6-pentafluorobenzyloxy)phenyl]methylidene]-N,N-dimethylhydrazine
(Compound No. 45)

In the same manner as in Example 36, carboxylic acid compound 2-(2,3,4,5,6-pentafluorobenzyloxy)benzoic acid was obtained. Then, in the same manner as in Example 3, the object compound was obtained (yellow liquid, yield from acylhydrazine compound 22%).

$^1$H-NMR spectrum (CDCl$_3$) δppm: 2.46 (6H, s), 5.10 (2H, s), 6.97 (1H, s), 7.12-7.18 (3H, m), 7.35 (1H, dd, J=7.3, 1.8 Hz), 7.49 (1H, s), 7.52 (1H, td, J=7.3, 1.8 Hz).

Mass spectrum m/z (FAB): 411 (M$^+$+1)

Example 46

N'-[1-imidazol-1-yl-1-[2-(4-methylbenzyloxy)phenyl]methylidene]-N,N-dimethylhydrazine
(Compound No. 46)

In the same manner as in Example 3, the object compound was obtained (yellow liquid, yield from acylhydrazine compound 68%).

¹H-NMR spectrum (CDCl₃) δppm: 2.32 (3H, s), 2.49 (6H, s), 4.99 (2H, s), 6.98-7.12 (7H, m), 7.27 (1H, t, J=1.4 Hz), 7.36 (1H, dd, J=7.3, 1.8 Hz), 7.43 (1H, td, J=7.3, 1.8 Hz), 7.60 (1H, s).
Mass spectrum m/z (FAB): 335 (M⁺+1)

Example 47

N'-[1-imidazol-1-yl-1-[2-(2,4-dimethylbenzyloxy)phenyl]methylidene]-N,N-dimethylhydrazine
(Compound No. 47)

In the same manner as in Example 36, carboxylic acid compound 2-(2,4-dimethylbenzyloxy)benzoic acid was obtained. Then, in the same manner as in Example 3, the object compound was obtained (yellow liquid, yield from acylhydrazine compound 27%).
¹H-NMR spectrum (CDCl₃) δppm: 2.13 (3H, s), 2.28 (3H, s), 2.47 (6H, s), 4.97 (2H, s), 6.90-7.02 (4H, m), 7.06-7.14 (2H, m), 7.25 (1H, t, J=1.4 Hz), 7.34 (1H, dd, J=7.3, 1.8 Hz), 7.46 (1H, td, J=7.3, 1.8 Hz), 7.56 (1H, s).
Mass spectrum m/z (FAB): 349 (M⁺+1)

Example 48

N'-[1-[2-(4-ethylbenzyloxy)phenyl]-1-imidazol-1-ylmethylidene]-N,N-dimethylhydrazine
(Compound No. 48)

In the same manner as in Example 36, carboxylic acid compound 2-(4-ethylbenzyloxy)benzoic acid was obtained. Then, in the same manner as in Example 3, the object compound was obtained (yellow liquid, yield from acylhydrazine compound 43%).
¹H-NMR spectrum (CDCl₃) δppm: 1.22 (3H, t, J=7.8 Hz), 2.49 (6H, S), 2.62 (2H, g, J=7.8 Hz), 5.00 (2H, s), 7.00-7.10 (5H, m), 7.13 (2H, d, J=8.2 Hz), 7.28 (1H, s), 7.36 (1H, d, J=7.8 Hz), 7.44 (1H, t, J=7.8 Hz), 7.61 (1H, s).
Mass spectrum m/z (FAB): 349 (M⁺+1)

Example 49

N'-[1-[2-(4-tert-butylbenzyloxy)phenyl]-1-imidazol-1-ylmethylidene]-N,N-dimethylhydrazine
(Compound No. 49)

In the same manner as in Example 36, carboxylic acid compound 2-(4-tert-butylbenzyloxy)benzoic acid was obtained. Then, in the same manner as in Example 3, the object compound was obtained (yellow liquid, yield from acylhydrazine compound 33%).
¹H-NMR spectrum (CDCl₃) δppm: 1.30 (9H, s), 2.49 (6H, s), 5.01 (2H, s), 7.00-7.10 (5H, m), 7.25-7.48 (5H, m), 7.64 (1H, s).
Mass spectrum m/z (FAB): 327 (M⁺+1)

Example 50

N'-[1-imidazol-1-yl-1-[2-(4-trifluoromethylbenzyloxy)phenyl]methylidene]-N,N-dimethylhydrazine
(Compound No. 50)

In the same manner as in Example 36, carboxylic acid compound 2-(4-trifluoromethylbenzyloxy)benzoic acid was obtained. Then, in the same manner as in Example 3, the object compound was obtained (yellow liquid, yield from acylhydrazine compound 28%).

¹H-NMR spectrum (CDCl₃) δppm: 2.50 (6H, s), 5.08 (2H, s), 7.00-7.06 (2H, m), 7.12 (1H, t, J=7.8 Hz), 7.22 (2H, d, J=8.2 Hz), 7.31 (1H, s), 7.40 (1H, dd, J=7.8, 1.8 Hz), 7.47 (1H, t, J=7.8 Hz), 7.56 (2H, d, J=8.2 Hz), 7.61 (1H, s).
Mass spectrum m/z (FAB): 389 (M⁺+1)

Example 51

N'-[1-imidazol-1-yl-1-[2-(3-trifluoromethylbenzyloxy)phenyl]methylidene]-N,N-dimethylhydrazine
(Compound No. 51)

In the same manner as in Example 36, carboxylic acid compound 2-(3-trifluoromethylbenzyloxy)benzoic acid was obtained. Then, in the same manner as in Example 1, the object compound was obtained as a mixture of geometric isomers (yellow liquid, yield from acylhydrazine compound 28%).
¹H-NMR spectrum (CDCl₃) δppm: 2.46, 2.70 (6H, s each), 5.03, 5.08 (2H, s each), 7.00-7.15 (3H, m), 7.20-7.35 (2H, m), 7.40-7.60 (5H, m), 7.91, 8.25 (1H, d each, J=8.7 Hz).
Mass spectrum m/z (FAB): 389 (M⁺+1)

Example 52

N'-[1-imidazol-1-yl-1-[2-(4-methoxybenzyloxy)phenyl]methylidene]-N,N-dimethylhydrazine
(Compound No. 52)

In the same manner as in Example 36, carboxylic acid compound 2-(4-methoxybenzyloxy)benzoic acid was obtained. Then, in the same manner as in Example 3, the object compound was obtained (yellow liquid, yield from acylhydrazine compound 15%).
¹H-NMR spectrum (CDCl₃) δppm: 2.49 (6H, s), 3.79 (3H, s), 4.96 (2H, br s), 6.82 (2H, d, J=8.7 Hz), 7.02-7.09 (5H, m), 7.26 (1H, s), 7.36 (1H, dd, J=7.3, 1.8 Hz), 7.42-7.47 (1H, m), 7.60 (1H, s).
Mass spectrum m/z (FAB): 351 (M⁺+1)

Example 53

N'-[1-imidazol-1-yl-1-[2-(3-methoxybenzyloxy)phenyl]methylidene]-N,N-dimethylhydrazine
(Compound No. 53)

In the same manner as in Example 36, carboxylic acid compound 2-(3-methoxybenzyloxy)benzoic acid was obtained. Then, in the same manner as in Example 3, the object compound was obtained (yellow liquid, yield from acylhydrazine compound 17%).
¹H-NMR spectrum (CDCl₃) δppm: 2.50 (6H, s), 3.75 (3H, s), 5.02 (2H, s), 6.72-6.74 (2H, m), 6.79-6.82 (1H, m), 7.03-7.10 (3H, m), 7.21 (1H, t, J=7.8 Hz), 7.31 (1H, s), 7.36 (1H, dd, J=7.8, 1.8 Hz), 7.42-7.47 (1H, m), 7.61 (1H, s).
Mass spectrum m/z (FAB): 351 (M⁺+1)

Example 54

N'-[1-imidazol-1-yl-1-[2-(4-trifluoromethoxybenzyloxy)phenyl]methylidene]-N,N-dimethylhydrazine
(Compound No. 54)

In the same manner as in Example 36, carboxylic acid compound 2-(4-trifluoromethoxybenzyloxy)benzoic acid was obtained. Then, in the same manner as in Example 3, the object compound was obtained (yellow liquid, yield from acylhydrazine compound 31%).

$^1$H-NMR spectrum (CDCl$_3$) δppm: 2.49 (6H, s), 5.02 (2H, s), 7.00-7.18 (7H, m), 7.29 (1H, s), 7.39 (1H, d, J=7.3 Hz), 7.47 (1H, t, J=7.3 Hz), 7.60 (1H, s).

Mass spectrum m/z (FAB): 405 (M$^+$+1)

Example 55

N'-[1-[2-(4-acetamidobenzyloxy)phenyl]-1-imidazol-1-ylmethylidene]-N,N-dimethylhydrazine (Compound No. 55)

In the same manner as in Example 64, the object compound was obtained (yellow liquid, yield 21%).

$^1$H-NMR spectrum (CDCl$_3$) δppm: 2.10 (3H, s), 2.50 (6H, s), 4.96 (2H, s), 6.96-7.12 (5H, m), 7.27 (1H, s), 7.34-7.52 (4H, m), 7.59 (1H, s), 8.73 (1H, s).

Mass spectrum m/z (FAB): 378 (M$^+$+1)

Example 56

N'-[1-imidazol-1-yl-1-(2-phenethoxyphenyl)methylidene]-N,N-dimethylhydrazine (Compound No. 56)

In the same manner as in Example 3, the object compound was obtained (yellow liquid, yield from acylhydrazine compound 47%).

$^1$H-NMR spectrum (CDCl$_3$) δppm: 2.40 (6H, s), 2.85 (2H, t, J=6.9 Hz), 4.11 (2H, t, J=6.9 Hz), 6.95 (1H, d, J=8.2 Hz), 7.03-7.10 (4H, m), 7.18-7.33 (5H, m), 7.41-7.45 (1H, m), 7.58 (1H, br s).

Mass spectrum m/z (FAB): 335 (M$^+$+1)

Example 57

N'-[1-[2-[2-(4-fluorophenyl)ethoxy]phenyl]-1-imidazol-1-ylmethylidene]-N,N-dimethylhydrazine (Compound No. 57)

In the same manner as in Example 36, carboxylic acid compound 2-[2-(4-fluorophenyl)ethoxy]benzoic acid was obtained. Then, in the same manner as in Example 3, the object compound was obtained (yellow liquid, yield from acylhydrazine compound 38%).

$^1$H-NMR spectrum (CDCl$_3$) δppm: 2.39 (6H, s), 2.82 (2H, t, J=6.4 Hz), 4.08 (2H, t, J=6.4 Hz), 6.89-6.96 (3H, m), 7.00-7.08 (4H, m), 7.31-7.34 (2H, m), 7.42-7.46 (1H, m), 7.56 (1H, s).

Mass spectrum m/z (FAB): 353 (M$^+$+1)

Example 58

N'-[1-imidazol-1-yl-1-[2-[2-(4-methoxyphenyl)ethoxy]phenyl]methylidene]-N,N-dimethylhydrazine (Compound No. 58)

In the same manner as in Example 36, carboxylic acid compound 2-[2-(4-methoxyphenyl)ethoxy]benzoic acid was obtained. Then, in the same manner as in Example 3, the object compound was obtained (yellow liquid, yield from acylhydrazine compound 39%).

$^1$H-NMR spectrum (CDCl$_3$) δppm: 2.41 (6H, s), 2.79 (2H, t, J=6.9 Hz), 3.78 (3H, s), 4.06 (2H, t, J=6.4 Hz), 6.75-6.79 (2H, m), 6.95 (1H, d, J=8.2 Hz), 7.00 (2H, d, J=8.7 Hz), 7.03-7.07 (2H, m), 7.30 (1H, s), 7.32 (1H, dd, J=7.6, 1.8 Hz), 7.41-7.45 (1H, m), 7.58 (1H, s).

Mass spectrum m/z (FAB): 365 (M$^+$+1)

Example 59

N'-[1-imidazol-1-yl-1-[2-(4-dimethylaminophenethyloxy)phenyl]methylidene]-N,N-dimethylhydrazine (Compound No. 59, lower polar isomer)

In the same manner as in Example 1, the object compound was obtained (yellow liquid, yield from acylhydrazine compound 19%).

$^1$H-NMR spectrum (CDCl$_3$) δppm: 2.56 (6H, s), 2.64 (2H, t, J=7.3 Hz), 2.91 (6H, s), 3.92 (2H, t, J=7.3 Hz), 6.66 (2H, d, J=8.7 Hz), 6.83 (1H, d, J=8.2 Hz), 6.92-7.07 (4H, m), 7.07 (1H, s), 7.28-7.46 (3H, m), 7.91 (1H, s).

Mass spectrum m/z (FAB): 378 (M$^+$+1)

Example 60

N'-[1-imidazol-1-yl-1-[2-(4-dimethylaminophenethyloxy)phenyl]methylidene]-N,N-dimethylhydrazine (Compound No. 60, higher polar isomer)

Since the compound obtained in Example 59 was a thermodynamically unstable isomer, the compound was isomerized to a thermodynamically stable geometric isomer in the same manner as in Example 3 to give the object compound (yellow liquid, isomerization yield 29%).

$^1$H-NMR spectrum (CDCl$_3$) δppm: 2.44 (6H, s), 2.75 (2H, t, J=7.3 Hz), 2.90 (6H, s), 4.04 (2H, br s), 6.63 (2H, d, J=8.7 Hz), 6.94-6.98 (3H, m), 7.02-7.06 (2H, m), 7.30-7.33 (2H, m), 7.40-7.44 (1H, m), 7.60 (1H, br s).

Mass spectrum m/z (FAB): 378 (M$^+$+1)

Example 61

N'-[1-imidazol-1-yl-1-[2-(3-phenylpropoxy)phenyl]methylidene]-N,N-dimethylhydrazine (Compound No. 61)

In the same manner as in Example 3, the object compound was obtained (yellow liquid, yield from acylhydrazine compound 40%).

$^1$H-NMR spectrum (CDCl$_3$) δppm: 1.85-1.92 (2H, m), 2.51 (6H, s), 2.51-2.57 (2H, m), 3.91 (2H, br s), 6.93 (1H, d, J=8.2 Hz), 7.04-7.09 (4H, m), 7.15-7.19 (1H, m), 7.24-7.28 (2H, m), 7.32 (1H, br s), 7.37 (1H, dd, J=7.8, 1.4 Hz), 7.41-7.46 (1H, m), 7.59 (1H, br s).

Mass spectrum m/z (FAB): 349 (M$^+$+1)

Example 62

N'-[1-imidazol-1-yl-1-[2-(4-phenylbutoxy)phenyl]methylidene]-N,N-dimethylhydrazine (Compound No. 62)

In the same manner as in Example 36, a carboxylic acid compound 2-(4-phenylbutoxy)benzoic acid was obtained. Then, in the same manner as in Example 3, the object compound was obtained (yellow liquid, yield from acylhydrazine compound 39%).

$^1$H-NMR spectrum (CDCl$_3$) δppm: 1.54-1.61 (4H, m), 2.48 (6H, s), 2.54-2.57 (2H, m), 3.91 (2H, br s), 6.94-7.19 (6H, m), 7.25-7.29 (3H, m), 7.34 (1H, dd, J=7.8, 1.4 Hz), 7.42-7.46 (1H, m), 7.54 (1H, br s).

Mass spectrum m/z (FAB): 363 (M$^+$+1)

Example 63

N'-[1-(2-cinnamyloxyphenyl)-1-imidazol-1-ylmethylidene]-N,N-dimethylhydrazine
(Compound No. 63)

In the same manner as in Example 36, a carboxylic acid compound 2-cinnamyloxybenzoic acid was obtained. Then, in the same manner as in Example 3, the object compound was obtained (yellow liquid, yield from acylhydrazine compound 30%).

$^1$H-NMR spectrum (CDCl$_3$) δppm: 2.51 (6H, s), 4.67 (2H, d, J=5.0 Hz), 6.13 (1H, dt, J=16.0, 5.0 Hz), 6.50 (1H, d, J=16.0 Hz), 7.04 (1H, s), 7.05 (1H, d, J=8.2 Hz), 7.08 (1H, t, J=7.3 Hz), 7.22-7.38 (7H, m), 7.46 (1H, t, J=8.2 Hz), 7.62 (1H, s).

Mass spectrum m/z (FAB): 347 (M$^+$+1)

Example 64

N'-[1-[2-(4-chlorophenoxymethoxy)phenyl]-1-imidazol-1-ylmethylidene]-N,N-dimethylhydrazine
(Compound No. 64)

To a solution of the Compound No. 13 (0.20 g, 0.869 mmol) obtained in Example 13 in N,N-dimethylformamide (3 ml) were added α,4-dichloroanisole (0.175 g, 0.989 mmol) and potassium carbonate (0.17 g, 1.23 mmol), and the mixture was stirred at room temperature for 20 hr. Ethyl acetate was added to the reaction mixture, the mixture was washed with water, and the organic layer was dried over sodium sulfate. The solvent was evaporated under reduced pressure, and the obtained residue was purified by silica gel column chromatography (hexane:ethyl acetate) to give the object compound (0.202 g, 0.545 mmol, yield 63%).

$^1$H-NMR spectrum (CDCl$_3$) δppm: 2.43 (6H, s), 5.62 (2H, s), 6.85 (2H, d, J=9.2 Hz), 7.00 (1H, s), 7.15-7.2 (4H, m), 7.35 (1H, dd, J=7.8, 1.8 Hz), 7.38 (1H, d, J=8.2 Hz), 7.50 (1H, td, J=7.8, 1.8 Hz), 7.58 (1H, s).

Mass spectrum m/z (FAB): 371 (M$^+$+1)

Example 65

N'-[1-imidazol-1-yl-1-[2-(2-phenoxyethoxy)phenyl]methylidene]-N,N-dimethylhydrazine (Compound No. 65, lower polar isomer)

In the same manner as in Example 36, a carboxylic acid compound 2-(2-phenoxyethoxy)benzoic acid was obtained. Then, in the same manner as in Example 1, the object compound was obtained (pale-yellow powder, yield from acylhydrazine compound 42%).

$^1$H-NMR spectrum (CDCl$_3$) δppm: 2.53 (6H, s), 3.93 (2H, t, J=5.0 Hz), 4.13 (2H, t, J=5.0 Hz), 6.85 (2H, d, J=8.2 Hz), 6.92-6.98 (3H, m), 7.04 (1H, t, J=7.3 Hz), 7.24-7.30 (2H, m), 7.35 (1H, s), 7.42 (1H, td, J=7.3, 1.8 Hz), 7.47 (1H, dd, J=7.3, 1.8 Hz), 7.81 (1H, s).

Mass spectrum m/z (FAB): 351 (M$^+$+1)

Example 66

N'-[1-imidazol-1-yl-1-[2-(2-phenoxyethoxy)phenyl]methylidene]-N,N-dimethylhydrazine (Compound No. 66, higher polar isomer)

To a solution of methyl salicylate (100.0 g, 657 mmol) in N,N-dimethylformamide (100 ml) were added β-bromophenetole (138.8 g, 690 mmol) and potassium carbonate (136.3 g, 986 mmol), and the mixture was stirred at 80° C. for 10 hr. After cooling the reaction mixture, water (1000 ml) was added, and the precipitated insoluble material was filtered to give methyl 2-(2-phenoxyethoxy)benzoate. This was suspended in methanol (250 ml), aqueous solution (200 ml) of sodium hydroxide (32 g, 800 mmol) was added at room temperature, and the mixture was stirred at 70° C. for 2 hr. After cooling, the mixture was neutralized with 6N-aqueous hydrochloric acid solution, and the precipitated insoluble material was filtered to give a carboxylic acid compound 2-(2-phenoxyethoxy)benzoic acid (160.8 g, 623 mmol, yield 95%). The obtained carboxylic acid compound (160.8 g, 623 mmol) was suspended in toluene (320 ml), thionyl chloride (81.5 g, 685 mmol) was added, and the mixture was stirred at 40° C. for 4 hr. N,N-Dimethylhydrazine (82.2 g, 1.37 mol) was added under ice-cooling, and the mixture was further stirred at room temperature for 0.5 hr. The reaction mixture was added dropwise to water (1000 ml), and the precipitated insoluble material was filtered to give an acylhydrazine compound N',N'-dimethyl-2-(2-phenoxyethoxy)benzohydrazide 131.6 g (yield 70%) as a white powder.

The obtained acylhydrazine compound (60.1 g, 200 mmol) was dissolved with heating in toluene (600 ml), thionyl chloride (29.7 g, 250 mmol) was added, and the mixture was stirred at 50° C. for 4 hr. Imidazole (68.1 g, 1.00 mol) was added thereto, and the mixture was stirred at 80° C. for 1 hr. The reaction mixture was washed with water, and the organic layer was extracted with 1N-aqueous hydrochloric acid solution. The aqueous layer was neutralized with 2N-aqueous sodium hydroxide solution, and the precipitated insoluble material was filtered to give the object compound (56.0 g) as an amorphous solid. This was crystallized from a mixed solvent of isopropanol-water to give the object compound (36.4 g, 104 mmol, yield 52%) as white crystals.

$^1$H-NMR spectrum (CDCl$_3$) δppm: 2.48 (6H, s), 4.10 (2H, t, J=5.0 Hz), 4.28 (2H, br s), 6.82 (2H, d, J=7.8 Hz), 6.95 (1H, t, J=7.3 Hz), 7.00 (1H, s), 7.07 (1H, d, J=7.8 Hz), 7.11 (1H, d, J=7.3 Hz), 7.24-7.29 (3H, m), 7.35 (1H, dd, J=7.8, 1.8 Hz), 7.45-7.50 (1H, m), 7.56 (1H, s).

Mass spectrum m/z (FAB): 351 (M$^+$+1)

Example 67

N,N-dimethyl-N'-[1-[2-(2-phenoxyethoxy)phenyl]-1-(1,2,4-triazol-1-yl)methylidene]hydrazine
(Compound No. 67)

In the same manner as in Example 18, the object compound was obtained (yellow liquid, yield from acylhydrazine compound 14%).

$^1$H-NMR spectrum (CDCl$_3$) δppm: 2.62 (6H, s), 4.04 (2H, t, J=5.0 Hz), 4.25 (2H, br s), 6.83 (2H, d, J=7.8 Hz), 6.96 (1H, t, J=7.3 Hz), 7.04 (1H, d, J=8.2 Hz), 7.10 (1H, t, J=7.3 Hz), 7.26-7.34 (2H, m), 7.44-7.49 (2H, m), 7.86 (1H, s), 8.50 (1H, s).

Mass spectrum m/z (FAB): 352 (M$^+$+1)

Example 68

N'-[1-[2-[2-(4-fluorophenoxy)ethoxy]phenyl]-1-imidazol-1-ylmethylidene]-N,N-dimethylhydrazine
(Compound No. 68)

In the same manner as in Example 36, a carboxylic acid compound 2-[2-(4-fluorophenoxy)ethoxy]benzoic acid was obtained. Then, in the same manner as in Example 3, the object compound was obtained (yellow liquid, yield from acylhydrazine compound 29%).

$^1$H-NMR spectrum (CDCl$_3$) δppm: 2.47 (6H, s), 4.05 (2H, t, J=5.0 Hz), 4.26 (2H, br s), 6.72-6.78 (2H, m), 6.9-6.98 (2H, m), 6.99 (1H, s), 7.06 (1H, d, J=8.2 Hz), 7.10 (1H, td, J=7.3, 0.9 Hz), 7.26 (1H, s), 7.35 (1H, dd, J=7.3, 1.8 Hz), 7.48 (1H, td, J=7.3, 1.8 Hz), 7.55 (1H, s).

Mass spectrum m/z (FAB): 369 (M$^+$+1)

Example 69

N'-[1-imidazol-1-yl-1-[2-[2-(4-methoxyphenoxy)ethoxy]phenyl]methylidene]-N,N-dimethylhydrazine (Compound No. 69)

In the same manner as in Example 36, a carboxylic acid compound 2-[2-(4-methoxyphenoxy)ethoxy]benzoic acid was obtained. Then, in the same manner as in Example 3, the object compound was obtained (pale-yellow powder, yield from acylhydrazine compound 49%).

$^1$H-NMR spectrum (CDCl$_3$) δppm: 2.48 (6H, s), 3.77 (3H, s), 4.04 (2H, t, J=5.0 Hz), 4.25 (2H, br s), 6.75 (2H, d, J=9.2 Hz), 6.81 (2H, d, J=9.2 Hz), 7.00 (1H, s), 7.06 (1H, d, J=8.7 Hz), 7.10 (1H, d, J=7.3 Hz), 7.26 (1H, s), 7.35 (1H, dd, J=7.3, 1.4 Hz), 7.47 (1H, td, J=7.8, 1.4 Hz), 7.57 (1H, s).

Mass spectrum m/z (FAB): 381 (M$^+$+1)

Example 70

N'-[1-imidazol-1-yl-1-[2-(3-phenoxypropoxy)phenyl]methylidene]-N,N-dimethylhydrazine (Compound No. 70)

In the same manner as in Example 36, a carboxylic acid compound 2-(3-phenoxypropoxy)benzoic acid was obtained. Then, in the same manner as in Example 3, the object compound was obtained (yellow liquid, yield from acylhydrazine compound 27%).

$^1$H-NMR spectrum (CDCl$_3$) δppm: 2.05 (2H, quin, J=6.0 Hz), 2.45 (6H, s), 3.85 (2H, t, J=6.0 Hz), 4.11 (2H, br s), 6.82 (2H, d, J=7.8 Hz), 6.93 (1H, t, J=7.3 Hz), 6.97 (1H, s), 7.01 (1H, d, J=8.2 Hz), 7.06 (1H, t, J=7.3 Hz), 7.2-7.3 (3H, m), 7.35 (1H, dd, J=7.3, 1.8 Hz), 7.45 (1H, td, J=7.3, 1.8 Hz), 7.59 (1H, s).

Mass spectrum m/z (FAB): 365 (M$^+$+1)

Example 71

N'-[1-imidazol-1-yl-1-[2-(4-phenoxybutoxy)phenyl]methylidene]-N,N-dimethylhydrazine (Compound No. 71)

In the same manner as in Example 36, a carboxylic acid compound 2-(4-phenoxybutoxy)benzoic acid was obtained. Then, in the same manner as in Example 3, the object compound was obtained (yellow liquid, yield from acylhydrazine compound 12%).

$^1$H-NMR spectrum (CDCl$_3$) δppm: 1.64-1.81 (4H, m), 2.49 (6H, s), 3.87 (2H, t, J=6.0 Hz), 3.99 (2H, br s), 6.86 (2H, d, J=7.8 Hz), 6.91-7.08 (4H, m), 7.25-7.29 (2H, m), 7.36 (1H, dd, J=7.8, 1.4 Hz), 7.43-7.48 (1H, m), 7.56 (1H, s).

Mass spectrum m/z (FAB): 379 (M$^+$+1)

Example 72

N'-[1-imidazol-1-yl-1-[2-(2-phenylsulfanylethoxy)phenyl]methylidene]-N,N-dimethylhydrazine (Compound No. 72)

In the same manner as in Example 36, a carboxylic acid compound 2-(2-phenylsulfanylethoxy)benzoic acid was obtained. Then, in the same manner as in Example 3, the object compound was obtained (yellow liquid, yield from acylhydrazine compound 19%).

$^1$H-NMR spectrum (CDCl$_3$) δppm: 2.50 (6H, s), 3.03 (2H, t, J=7.3 Hz), 4.06-4.08 (2H, m), 6.91 (1H, d, J=8.2 Hz), 7.02 (1H, s), 7.07 (1H, t, J=7.3 Hz), 7.19-7.36 (7H, m), 7.40-7.45 (1H, m), 7.56 (1H, s).

Mass spectrum m/z (FAB): 367 (M$^+$+1)

Example 73

N'-[1-[2-(2,3-dihydrobenzo[1,4]dioxin-2-ylmethoxy)phenyl]-1-imidazol-1-ylmethylidene]-N,N-dimethylhydrazine (Compound No. 73)

In the same manner as in Example 36, a carboxylic acid compound 2-(2,3-dihydrobenzo[1,4]dioxin-2-ylmethoxy)benzoic acid was obtained. Then, in the same manner as in Example 3, the object compound was obtained (yellow liquid, yield from acylhydrazine compound 16%).

$^1$H-NMR spectrum (CDCl$_3$) δppm: 2.50 (6H, s), 3.85 (1H, br s), 4.04-4.20 (3H, m), 4.31 (1H, br s), 6.82-6.90 (4H, m), 7.01-7.04 (2H, m), 7.12 (1H, t, J=7.3 Hz), 7.28 (1H, s), 7.39 (1H, d, J=6.4 Hz), 7.48 (1H, t, J=8.2 Hz), 7.56 (1H, s).

Mass spectrum m/z (FAB): 379 (M$^+$+1)

Example 74

N'-[1-imidazol-1-yl-1-[2-(pyridin-2-ylmethoxy)phenyl]methylidene]-N,N-dimethylhydrazine (Compound No. 74)

In the same manner as in Example 36, a carboxylic acid compound 2-(pyridin-2-ylmethoxy)benzoic acid was obtained. Then, in the same manner as in Example 3, the object compound was obtained (yellow liquid, yield from acylhydrazine compound 8%).

$^1$H-NMR spectrum (CDCl$_3$) δppm: 2.51 (6H, s), 5.17 (2H, s), 6.99 (1H, d, J=7.8 Hz), 7.05-7.12 (3H, m), 7.16-7.19 (1H, m), 7.32 (1H, s), 7.40 (1H, d, J=7.3 Hz), 7.44-7.48 (1H, m), 7.62 (1H, t, J=7.8 Hz), 7.65 (1H, s), 8.52 (1H, d, J=5.0 Hz).

Mass spectrum m/z (FAB): 322 (M$^+$+1)

Example 75

N'-[1-imidazol-1-yl-1-[2-(2-pyridin-2-ylethoxy)phenyl]methylidene]-N,N-dimethylhydrazine (Compound No. 75)

In the same manner as in Example 36, a carboxylic acid compound 2-(2-pyridin-2-ylethoxy)benzoic acid was obtained. Then, in the same manner as in Example 3, the object compound was obtained (yellow liquid, yield from acylhydrazine compound 54%).

$^1$H-NMR spectrum (CDCl$_3$) δppm: 2.37 (6H, s), 3.02 (2H, t, J=6.4 Hz), 4.31 (2H, br), 6.95 (1H, d, J=7.8 Hz), 7.00-7.10 (2H, m), 7.11 (2H, s), 7.22 (1H, s), 7.30 (1H, dd, J=7.3, 1.8 Hz), 7.42-7.46 (1H, m), 7.51 (1H, td, J=7.8, 1.8 Hz), 7.55 (1H, s), 8.46-8.48 (1H, m).

Mass spectrum m/z (FAB): 336 (M$^+$+1)

Example 76

N'-[1-imidazol-1-yl-1-[2-[2-(3-pyridyloxy)ethoxy]phenyl]methylidene]-N,N-dimethylhydrazine (Compound No. 76)

In the same manner as in Example 36, a carboxylic acid compound 2-[2-(3-pyridyloxy)ethoxy]benzoic acid was obtained. Then, in the same manner as in Example 3, the object compound was obtained (pale-yellow powder, yield from acylhydrazine compound 33%).

$^1$H-NMR spectrum (CDCl$_3$) δppm: 2.47 (6H, s), 4.14 (2H, t, J=4.6 Hz), 4.30 (2H, br s), 6.99 (1H, s), 7.06-7.14 (4H, m), 7.19-7.22 (1H, m), 7.37 (1H, dd, J=7.3, 1.4 Hz), 7.47-7.52 (1H, m), 7.54 (1H, s), 8.22-8.23 (2H, m).

Mass spectrum m/z (FAB): 352 (M$^+$+1)

Example 77

N'-[1-[2-[2-(4-chlorophenyl)thiazol-4-ylmethoxy]phenyl]-1-imidazol-1-ylmethylidene]-N,N-dimethylhydrazine (Compound No. 77)

In the same manner as in Example 64, the object compound was obtained (yellow liquid, yield 19%).

$^1$H-NMR spectrum (CDCl$_3$) δppm: 2.51 (6H, s), 5.23 (2H, s), 6.88 (1H, s), 7.04 (1H, s), 7.09-7.14 (2H, m), 7.33 (1H, s), 7.39 (1H, s), 7.40 (2H, d, J=8.7 Hz), 7.48 (1H, td, J=8.2, 1.8 Hz), 7.65 (1H, s), 7.84 (2H, d, J=8.7 Hz).

Mass spectrum m/z (FAB): 438 (M$^+$+1)

Example 78

N'-[1-[2-(5-chlorobenzothiophen-2-ylmethoxy)phenyl]-1-imidazol-1-ylmethylidene]-N,N-dimethylhydrazine (Compound No. 78)

In the same manner as in Example 64, the object compound was obtained (yellow liquid, yield 24%).

$^1$H-NMR spectrum (CDCl$_3$) δppm: 2.47 (6H, s), 5.22 (2H, s), 6.99 (1H, s), 7.09-7.16 (2H, m), 7.25 (1H, s), 7.26 (1H, s), 7.31 (1H, dd, J=8.7, 1.8 Hz), 7.37 (1H, dd, J=7.3, 1.8 Hz), 7.49 (1H, t, J=7.3 Hz), 7.55 (1H, s), 7.64 (1H, d, J=2.3 Hz), 7.74 (1H, d, J=8.7 Hz).

Mass spectrum m/z (FAB): 411 (M$^+$+1)

Example 79

N'-[1-imidazol-1-yl-1-(2-methylthiophenyl)methylidene]-N,N-dimethylhydrazine (Compound No. 79)

In the same manner as in Example 3, the object compound was obtained (pale-yellow powder, yield from acylhydrazine compound 57%).

$^1$H-NMR spectrum (CDCl$_3$) δppm: 2.42 (3H, s), 2.54 (6H, s), 7.05 (1H, s), 7.24-7.37 (4H, m), 7.45-7.49 (1H, m), 7.51 (1H, s).

Mass spectrum m/z (FAB): 261 (M$^+$+1)

Example 80

N'-[1-(2-ethylthiophenyl)-1-imidazol-1-ylmethylidene]-N,N-dimethylhydrazine (Compound No. 80)

In the same manner as in Example 3, the object compound was obtained (yellow liquid, yield from acylhydrazine compound 4%).

$^1$H-NMR spectrum (CDCl$_3$) δppm: 1.23 (3H, t, J=7.3 Hz), 2.53 (6H, s), 2.84-2.98 (2H, m), 7.05 (1H, s), 7.25-7.33 (3H, m), 7.42-7.48 (2H, m), 7.52 (1H, s).

Mass spectrum m/z (FAB): 275 (M$^+$+1)

Example 81

N'-[1-imidazol-1-yl-1-(2-propylthiophenyl)methylidene]-N,N-dimethylhydrazine (Compound No. 81)

In the same manner as in Example 3, the object compound was obtained (yellow liquid, yield from acylhydrazine compound 5%).

$^1$H-NMR spectrum (CDCl$_3$) δppm: 0.93 (3H, t, J=7.3 Hz), 1.52-1.60 (2H, m), 2.53 (6H, s), 2.78-2.93 (2H, m), 7.04 (1H, s), 7.26-7.32 (3H, m), 7.43-7.45 (2H, m), 7.52 (1H, s).

Mass spectrum m/z (FAB): 289 (M$^+$+1)

Example 82

N'-[1-(2-butylthiophenyl)-1-imidazol-1-ylmethylidene]-N,N-dimethylhydrazine (Compound No. 82)

In the same manner as in Example 3, the object compound was obtained (yellow liquid, yield from acylhydrazine compound 14%).

$^1$H-NMR spectrum (CDCl$_3$) δppm: 0.87 (3H, t, J=7.3 Hz), 1.31-1.40 (2H, m), 1.49-1.59 (2H, m), 2.53 (6H, s), 2.83-2.92 (2H, m), 7.04 (1H, s), 7.26-7.31 (3H, m), 7.42-7.45 (2H, m), 7.52 (1H, s).

Mass spectrum m/z (FAB): 303 (M$^+$+1)

Example 83

N'-[1-imidazol-1-yl-1-(2-pentylthiophenyl)methylidene]-N,N-dimethylhydrazine (Compound No. 83)

To a solution of methyl thiosalicylate (1.063 g, 6.32 mmol) in N,N-dimethylformamide (10 ml) were added 1-iodopentane (0.87 ml, 6.57 mmol) and potassium carbonate (0.997 g, 7.22 mmol), and the mixture was stirred at 80° C. for 5 hr. Ethyl acetate was added to the reaction mixture, the mixture was washed with water, and the organic layer was dried over sodium sulfate. The solvent was evaporated under reduced pressure, and the obtained residue was purified by silica gel column chromatography (hexane:ethyl acetate) to give methyl 2-pentylthiobenzoate quantitatively. This was dissolved in methanol (15 ml), 1N-aqueous sodium hydroxide solution (15 ml) was added at room temperature, and the mixture was stirred at 50° C. for 1.5 hr. The reaction mixture was concentrated under reduced pressure and neutralized with 1N-aqueous hydrochloric acid solution, and the mixture was extracted with ethyl acetate. The extract was dried over sodium sulfate, and the solvent was evaporated under reduced pressure to give a carboxylic acid compound 2-pentylthiobenzoic acid (1.370 g, 6.11 mmol, yield 97%).

Using the obtained carboxylic acid compound and in the same manner as in Example 3, the object compound was obtained (yellow liquid, yield from acylhydrazine compound 31%).

$^1$H-NMR spectrum (CDCl$_3$) δppm: 0.86 (3H, t, J=6.9 Hz), 1.22-1.32 (4H, m), 1.54-1.58 (2H, m), 2.53 (6H, s), 2.81-2.93 (2H, m), 7.04 (1H, br s), 7.26-7.33 (3H, m), 7.43-7.47 (2H, m), 7.53 (1H, br s).

Mass spectrum m/z (FAB): 317 (M$^+$+1)

Example 84

N'-[1-imidazol-1-yl-1-(2-phenethylthiophenyl)methylidene]-N,N-dimethylhydrazine
(Compound No. 84)

In the same manner as in Example 83, the object compound was obtained (yellow liquid, yield from acylhydrazine compound 44%).

$^1$H-NMR spectrum (CDCl$_3$) δppm: 2.52 (6H, s), 2.79-2.84 (2H, m), 3.08-3.15 (2H, m), 7.06 (1H, s), 7.14 (2H, d, J=7.3 Hz), 7.19-7.34 (6H, m), 7.46 (2H, d, J=3.2 Hz), 7.56 (1H, s).

Mass spectrum m/z (FAB): 351 (M$^+$+1)

Example 85

N'-[1-imidazol-1-yl-1-[2-(2-phenoxyethylthio)phenyl]methylidene]-N,N-dimethylhydrazine
(Compound No. 85)

In the same manner as in Example 83, the object compound was obtained (pale-yellow powder, yield from acylhydrazine compound 3%).

$^1$H-NMR spectrum (CDCl$_3$) δppm: 2.52 (6H, s), 3.18-3.35 (2H, m), 4.00-4.04 (2H, m), 6.79 (2H, d, J=7.8 Hz), 6.95 (1H, t, J=7.8 Hz), 7.03 (1H, s), 7.23-7.28 (4H, m), 7.32-7.33 (2H, m), 7.45-7.49 (1H, m), 7.57 (1H, s).

Mass spectrum m/z (FAB): 367 (M$^+$+1)

Example 86

N'-[1-imidazol-1-yl-1-(2-methanesulfonylphenyl)methylidene]-N,N-dimethylhydrazine
(Compound No. 86)

To a solution of 2-methanesulfonylbenzoic acid (0.508 g, 2.54 mmol) in 1,2-dichloroethane (6 ml) were added oxalyl chloride (0.24 ml, 2.76 mmol) and N,N-dimethylformamide (0.01 ml), and the mixture was stirred at room temperature for 2 hr. The reaction solvent was evaporated under reduced pressure, and the residue was dissolved in 1,2-dichloroethane (6 ml). N,N-Dimethylhydrazine (0.21 ml, 2.76 mmol) and N-methylmorpholine (0.36 ml, 3.23 mmol) were added under ice-cooling, and the mixture was stirred at room temperature for 20 hr. The reaction mixture was washed with water, and the organic layer was dried over sodium sulfate. The solvent was evaporated under reduced pressure, and the obtained residue was purified by silica gel column chromatography (hexane:ethyl acetate) to give an acylhydrazine compound N',N'-dimethyl-2-methanesulfonylbenzohydrazide (0.070 g, 0.29 mmol, yield 11%) as a white powder.

The obtained acylhydrazine compound N',N'-dimethyl-2-methanesulfonylbenzohydrazide (0.068 g, 0.28 mmol) was dissolved in toluene (1 ml), phosphorus oxychloride (0.3 ml) was added, and the mixture was stirred at 60° C. for 3 hr. The reaction solvent was evaporated under reduced pressure, imidazole (0.099 g, 1.45 mmol) was added to a solution of the residue in 1,2-dichloroethane (2 ml), and the mixture was stirred at 60° C. for 18 hr. The reaction mixture was washed with water, and the organic layer was dried over sodium sulfate and evaporated under reduced pressure. The residue was purified by silica gel column chromatography (hexane:ethyl acetate) to give the object compound (0.01 g, 0.03 mmol, yield 11%) as a yellow liquid.

$^1$H-NMR spectrum (CDCl$_3$) δppm: 2.54 (6H, s), 2.81 (3H, s), 7.04 (1H, s), 7.17 (1H, s), 7.55-7.57 (2H, m), 7.73-7.82 (2H, m), 8.16 (1H, dd, J=7.3, 1.4 Hz).

Mass spectrum m/z (FAB): 293 (M$^+$+1)

Example 87

N'-[1-imidazol-1-yl-1-[2-(N-methyl-N-pentylamino)phenyl]methylidene]-N,N-dimethylhydrazine
(Compound No. 87)

3,1-Benzoxazin-2,4-(1H)-dione (1.0 g, 6.13 mmol) was dissolved in N,N-dimethylformamide (10 ml), 60% sodium hydride (0.296 g, 7.39 mmol) was added under ice-cooling, and the mixture was stirred at room temperature for 1 hr. 1-Iodopentane (0.97 ml, 7.32 mmol) was added, and the mixture was stirred at room temperature for 2 hr. Ethyl acetate was added to the reaction mixture, the mixture was washed with water, and the organic layer was dried over sodium sulfate. The solvent was evaporated under reduced pressure, and the obtained residue was purified by silica gel column chromatography (hexane:ethyl acetate) to give 1-pentyl-3,1-benzoxazin-2,4-(1H)-dione (0.634 g, 2.72 mmol, yield 44%).

The obtained 1-pentyl-3,1-benzoxazin-2,4-(1H)-dione (0.301 g, 1.29 mmol) was dissolved in toluene (4 ml), N,N-dimethylhydrazine (0.10 ml, 1.32 mmol) was added, and the mixture was stirred at 100° C. for 2 hr. The reaction mixture was evaporated under reduced pressure, and the obtained residue was purified by silica gel column chromatography (hexane:ethyl acetate) to give N',N'-dimethyl-2-pentylaminobenzohydrazide (0.218 g, 0.87 mmol, yield 67%). This was dissolved in methanol (3 ml), 36% formalin (0.35 ml, 4.31 mmol), sodium cyanoborohydride (0.174 g, 2.62 mmol) and acetic acid (0.1 ml) were added, and the mixture was stirred at room temperature for 20 hr. The reaction mixture was concentrated under reduced pressure, and ethyl acetate was added. The mixture was washed with water, and the organic layer was dried over sodium sulfate. The solvent was evaporated under reduced pressure, and the obtained residue was purified by silica gel column chromatography (hexane:ethyl acetate) to give an acylhydrazine compound N',N'-dimethyl-2-(N-methyl-N-pentylamino)benzohydrazide (0.103 g, 0.39 mmol, yield 45%).

Using the obtained acylhydrazine compound and in the same manner as in Example 3, the object compound was obtained (yellow liquid, yield from acylhydrazine compound 34%).

$^1$H-NMR spectrum (CDCl$_3$) δppm: 0.85 (3H, t, J=7.3 Hz), 1.06-1.13 (2H, m), 1.19-1.28 (2H, m), 1.31-1.43 (2H, m), 2.55 (6H, s), 2.67 (3H, s), 2.95 (2H, t, J=7.8 Hz), 6.91-6.95 (1H, m), 7.00-7.02 (2H, m), 7.26-7.32 (2H, m), 7.34-7.39 (1H, m), 7.59 (1H, s).

Mass spectrum m/z (FAB): 314 (M$^+$+1)

Example 88

N'-[1-imidazol-1-yl-1-[2-[N-methyl-N-(2-phenoxyethyl)amino]phenyl]methylidene]-N,N-dimethylhydrazine (Compound No. 88)

In the same manner as in Example 87, the object compound was obtained (yellow liquid, yield from acylhydrazine compound 31%).
$^1$H-NMR spectrum (CDCl$_3$) δppm: 2.54 (6H, s), 2.81 (3H, s), 3.45 (2H, t, J=6.0 Hz), 3.92 (2H, t, J=6.0 Hz), 6.78 (2H, d, J=7.8 Hz), 6.91-7.02 (3H, m), 7.12 (1H, d, J=8.2 Hz), 7.23-7.28 (3H, m), 7.32 (1H, dd, J=7.8, 1.8 Hz), 7.37-7.43 (1H, m), 7.62 (1H, s).
Mass spectrum m/z (FAB): 364 (M$^+$+1)

Example 89

N'-[1-[2-(N-benzyl-N-methylamino)phenyl]-1-imidazol-1-ylmethylidene]-N,N-dimethylhydrazine (Compound No. 89)

In the same manner as in Example 87, the object compound was obtained (yellow liquid, yield from acylhydrazine compound 22%).
$^1$H-NMR spectrum (CDCl$_3$) δppm: 2.54 (6H, s), 2.59 (3H, s), 4.14 (1H, d, J=15.1 Hz), 4.24 (1H, d, J=14.7 Hz), 7.01-7.07 (4H, m), 7.11 (1H, d, J=8.2 Hz), 7.21-7.35 (5H, m), 7.39-7.43 (1H, m), 7.61 (1H, s).
Mass spectrum m/z (FAB): 334 (M$^+$+1)

Example 90

N'-[1-[2-(N-benzyl-N-methylamino)-5-bromophenyl]-1-imidazol-1-ylmethylidene]-N,N-dimethylhydrazine (Compound No. 90)

In the same manner as in Example 87, the object compound was obtained (pale-yellow powder, yield from acylhydrazine compound 37%).
$^1$H-NMR spectrum (CDCl$_3$) δppm: 2.56 (6H, s), 2.59 (3H, s), 4.17 (1H, d, J=16.0 Hz), 4.23 (1H, d, J=15.0 Hz), 6.94 (1H, J=8.7 Hz), 7.03-7.08 (3H, m), 7.22-7.27 (4H, m), 7.42-7.49 (2H, m), 7.65 (1H, s).
Mass spectrum m/z (FAB): 412 (M$^+$+1)

Example 91

N'-[1-imidazol-1-yl-1-(2-methanesulfonamidophenyl)methylidene]-N,N-dimethylhydrazine (Compound No. 91)

2-Methanesulfonamidobenzoic acid (1.00 g, 4.65 mmol) was dissolved in N,N-dimethylformamide (10 ml), 1-ethyl-3-(3-dimethylaminopropyl)carbodiimide hydrochloride (1.073 g, 5.60 mmol), 1-hydroxybenzotriazole (0.857 g, 5.60 mmol) and N,N-dimethylhydrazine (0.39 ml, 5.13 mmol) was successively added under ice-cooling, and the mixture was stirred at room temperature for 24 hr. Ethyl acetate was added to the reaction mixture, the mixture was washed successively with saturated aqueous sodium hydrogen carbonate solution and water, and the organic layer was dried over sodium sulfate. The solvent was evaporated under reduced pressure, and the obtained residue was purified by silica gel column chromatography (hexane:ethyl acetate) to give an acylhydrazine compound N',N'-dimethyl-2-(2-methanesulfonamido)benzohydrazide (0.614 g, 2.39 mmol, yield 51%).

The obtained acylhydrazine compound (0.397 g, 1.54 mmol) was dissolved in toluene (4 ml), phosphorus oxychloride (2.0 ml) was added, and the mixture was stirred at 60° C. for 2 hr. The reaction solvent was evaporated under reduced pressure, imidazole (0.557 g, 8.18 mmol) was added to a solution of the residue in N,N-dimethylformamide (5 ml), and the mixture was stirred at 60° C. for 4 hr. Ethyl acetate was added to the reaction mixture, the mixture was washed with water, and the organic layer was dried over sodium sulfate. The solvent was evaporated under reduced pressure, and the obtained residue was purified by silica gel column chromatography (hexane:ethyl acetate) to give the object compound (0.04 g, 0.13 mmol, yield 8%) as a yellow liquid.
$^1$H-NMR spectrum (CDCl$_3$) δppm: 2.64 (6H, s), 2.86 (3H, s), 7.10 (1H, br s), 7.17 (1H, br s), 7.24-7.25 (1H, m), 7.29-7.33 (1H, m), 7.59-7.63 (1H, m), 7.73 (1H, br s), 7.78 (1H, d, J=8.2 Hz), 9.78 (1H, br s).
Mass spectrum m/z (FAB): 308 (M$^+$+1)

Example 92

N'-[1-imidazol-1-yl-1-(1-pentyloxynaphthalen-2-yl)methylidene]-N,N-dimethylhydrazine (Compound No. 92)

In the same manner as in Example 36, a carboxylic acid compound 1-pentyloxynaphthalene-2-carboxylic acid was obtained. Then, in the same manner as in Example 3, the object compound was obtained (yellow liquid, yield from acylhydrazine compound 3%).
$^1$H-NMR spectrum (CDCl$_3$) δppm: 0.89 (3H, t, J=7.3 Hz), 1.25-1.36 (4H, m), 1.67-1.74 (2H, m), 2.56 (6H, s), 3.93-3.96 (2H, m), 7.06 (1H, s), 7.32 (1H, s), 7.37 (1H, d, J=8.2 Hz), 7.53-7.66 (3H, m), 7.70 (1H, s), 7.87-7.89 (1H, m), 8.20-8.22 (1H, m).
Mass spectrum m/z (FAB): 351 (M$^+$+1)

Example 93

N'-[1-imidazol-1-yl-1-(2-pentyloxynaphthalen-1-yl)methylidene]-N,N-dimethylhydrazine (Compound No. 93)

In the same manner as in Example 36, a carboxylic acid compound 2-pentyloxynaphthalene-1-carboxylic acid was obtained. Then, in the same manner as in Example 3, the object compound was obtained (yellow liquid, yield from acylhydrazine compound 38%).
$^1$H-NMR spectrum (CDCl$_3$) δppm: 0.86 (3H, t, J=6.9 Hz), 1.21-1.30 (4H, m), 1.58-1.67 (2H, m), 2.48 (6H, s), 3.94-4.00 (1H, m), 4.10-4.16 (1H, m), 7.00 (1H, s), 7.29-7.32 (2H, m), 7.37-7.41 (1H, m), 7.45-7.49 (2H, m), 7.54 (1H, d, J=8.2 Hz), 7.84 (1H, d, J=8.2 Hz), 7.98 (1H, d, J=9.2 Hz).
Mass spectrum m/z (FAB): 351 (M$^+$+1)

Example 94

N'-[1-imidazol-1-yl-1-(3-propyloxypyridin-2-yl)methylidene]-N,N-dimethylhydrazine (Compound No. 94)

To a solution of methyl 3-hydroxypicolinate (0.472 g, 3.08 mmol) in N,N-dimethylformamide (6 ml) were added 1-iodopropane (0.33 ml, 3.38 mmol) and potassium carbonate (0.519 g, 3.76 mmol), and the mixture was stirred at 80° C. for 3 hr. Ethyl acetate was added to the reaction mixture, the mixture was washed with water, and the organic layer was dried over sodium sulfate. The solvent was evaporated under reduced pressure, and the obtained residue was purified by silica gel column chromatography (hexane:ethyl acetate) to give methyl 3-propyloxypicolinate (0.418 g, 2.14 mmol, yield 69%). This was dissolved in methanol (5 ml), 1N-aqueous sodium hydroxide m solution (5 ml) was added at room temperature, and the mixture was stirred at 60° C. for 3.5 hr. The reaction mixture was concentrated under reduced pressure and neutralized with 5%-aqueous citric acid solution, and the mixture was extracted with ethyl acetate. The extract was dried over sodium sulfate, and the solvent was evaporated under reduced pressure to give a carboxylic acid compound 3-propyloxypicolinic acid (0.248 g, 1.37 mmol, yield 64%).

The obtained carboxylic acid compound (0.248 g, 1.37 mmol) was dissolved in N,N-dimethylformamide (4 ml), 1-ethyl-3-(3-dimethylaminopropyl)carbodiimide hydrochloride (0.330 g, 1.72 mmol), 1-hydroxybenzotriazole (0.264 g, 1.72 mmol) and N,N-dimethylhydrazine (0.11 ml, 1.45 mmol) were successively added under ice-cooling, and the mixture was stirred at room temperature for 15 hr. Ethyl acetate was added to the reaction mixture, the mixture was washed successively with saturated aqueous sodium hydrogen carbonate solution and water, and the organic layer was dried over sodium sulfate. The solvent was evaporated under reduced pressure, and the obtained residue was purified by silica gel column chromatography (hexane:ethyl acetate) to give an acylhydrazine compound 3-propyloxypicolinic acid N',N'-dimethylhydrazide (0.157 g, 0.703 mmol, yield 51%).

Using the obtained acylhydrazine compound and in the same manner as in Example 3, the object compound was obtained (yellow liquid, yield from acylhydrazine compound 12%).

$^1$H-NMR spectrum (CDCl$_3$) δppm: 0.88 (3H, t, J=7.3 Hz), 1.64-1.73 (2H, m), 2.54 (6H, s), 3.93 (2H, t, J=6.4 Hz), 7.03 (1H, s), 7.26 (1H, s), 7.31 (1H, dd, J=8.2, 0.9 Hz), 7.37-7.40 (1H, m), 7.53 (1H, s), 8.32 (1H, dd, J=4.6, 1.4 Hz).

Mass spectrum m/z (FAB): 274 (M$^+$+1)

Example 95

N'-[1-imidazol-1-yl-1-(3-pentyloxypyridin-2-yl)methylidene]-N,N-dimethylhydrazine
(Compound No. 95)

In the same manner as in Example 94, the object compound was obtained (yellow liquid, yield from acylhydrazine compound 37%).

$^1$H-NMR spectrum (CDCl$_3$) δppm: 0.85-0.96 (3H, m), 1.25-1.69 (4H, m), 1.86-1.93 (2H, m), 2.54, 2.71 (6H, s each), 3.95-4.13 (2H, m), 7.03, 7.07 (1H, s each), 7.21-7.42 (3H, m), 7.52, 7.86 (1H, each), 8.23-8.32 (1H, m).

Mass spectrum m/z (FAB): 302 (M$^+$+1)

Example 96

N'-[1-imidazol-1-yl-1-[3-(4-methoxybenzyloxy)pyridin-2-yl]methylidene]-N,N-dimethylhydrazine
(Compound No. 96)

In the same manner as in Example 94, the object compound was obtained (yellow liquid, yield from acylhydrazine compound 10%).

$^1$H-NMR spectrum (CDCl$_3$) δppm: 2.53 (6H, s), 3.80 (3H, s), 5.03 (2H, s), 6.85 (2H, d, J=8.7 Hz), 7.05 (1H, s), 7.12 (2H, d, J=8.7 Hz), 7.24 (1H, d, J=0.9 Hz), 7.36 (2H, d, J=3.2 Hz), 7.54 (1H, s), 8.32-8.33 (1H, m).

Mass spectrum m/z (FAB): 352 (M$^+$+1)

Example 97

N'-[1-imidazol-1-yl-1-[3-(2-phenoxyethoxy)pyridin-2-yl]methylidene]-N,N-dimethylhydrazine
(Compound No. 97)

In the same manner as in Example 94, the object compound was obtained (yellow liquid, yield from acylhydrazine compound 58%).

$^1$H-NMR spectrum (CDCl$_3$) δppm: 2.51 (6H, s), 4.18-4.20 (2H, m), 4.34-4.37 (2H, m), 6.83 (2H, d, J=8.7 Hz), 6.95-7.01 (2H, m), 7.23-7.29 (3H, m), 7.41-7.44 (2H, m), 7.55 (1H, s), 8.36-8.37 (1H, m).

Mass spectrum m/z (FAB): 352 (M$^+$+1)

Example 98

N'-[1-imidazol-1-yl-1-[3-(3-phenoxypropoxy)pyridin-2* yl]methylidene]-N,N-dimethylhydrazine
(Compound No. 98)

In the same manner as in Example 94, the object compound was obtained (yellow liquid, yield from acylhydrazine compound 6%).

$^1$H-NMR spectrum (CDCl$_3$) δppm: 2.14 (2H, quin, J=6.0 Hz), 2.51 (6H, s), 3.95 (2H, t, J=6.0 Hz), 4.20 (2H, t, J=6.0 Hz), 6.83 (2H, d, J=7.8 Hz), 6.89-6.96 (2H, m), 7.02 (1H, s), 7.21 (1H, s), 7.25-7.29 (1H, m), 7.37-7.41 (2H, m), 7.61 (1H, s), 8.33-8.34 (1H, m).

Mass spectrum m/z (FAB): 366 (M$^+$+1)

Example 99

N'-[1-(2-ethoxypyridin-3-yl)-1-imidazol-1-ylmethylidene]-N,N-dimethylhydrazine
(Compound No. 99)

In the same manner as in Example 94, the object compound was obtained (yellow liquid, yield from acylhydrazine compound 36%).

$^1$H-NMR spectrum (CDCl$_3$) δppm: 1.22 (3H, t, J=6.9 Hz), 2.48 (6H, s), 4.36 (2H, q, J=6.9 Hz), 6.99-7.04 (2H, m), 7.60 (1H, s), 7.67 (1H, dd, J=7.3, 1.8 Hz), 8.30 (1H, dd, J=5.0, 1.8 Hz).

Mass spectrum m/z (FAB): 260 (M$^+$+1)

Example 100

N'-[1-imidazol-1-yl-1-(3-methylthiophen-2-yl)methylidene]-N,N-dimethylhydrazine
(Compound No. 100)

In the same manner as in Example 1, the object compound was obtained (yellow liquid, yield from acylhydrazine compound 19%).

$^1$H-NMR spectrum (CDCl$_3$) δppm: 1.96 (3H, s), 2.52 (6H, s), 6.84 (1H, d, J=5.0 Hz), 7.17 (1H, s), 7.23 (1H, d, J=5.0 Hz), 7.26 (1H, s), 7.80 (1H, s).

Mass spectrum m/z (FAB): 235 (M$^+$+1)

Example 101

N'-[1-imidazol-1-yl-1-[3-(2-phenoxyethoxy)thiophen-2-yl]methylidene]-N,N-dimethylhydrazine (Compound No. 101)

To a solution of methyl 3-hydroxythiophene-2-carboxylate (0.992 g, 6.27 mmol) in N,N-dimethylformamide (12 ml) were added β-bromophenetole (1.268 g, 6.31 mmol) and potassium carbonate (1.059 g, 7.66 mmol), and the mixture was stirred at 80° C. for 4.5 hr. Ethyl acetate was added to the reaction mixture, the mixture was washed with water, and the organic layer was dried over sodium sulfate. The solvent was evaporated under reduced pressure, and the obtained residue was purified by silica gel column chromatography (hexane:ethyl acetate) to give methyl 3-(2-phenoxyethoxy)thiophene-2-carboxylate (1.624 g, 5.83 mmol, yield 93%). This was dissolved in methanol (12 ml), 1N-aqueous sodium hydroxide solution (12 ml) was added at room temperature, and the mixture was stirred at 60° C. for 2 hr. The reaction mixture was concentrated under reduced pressure and neutralized with 1N-aqueous hydrochloric acid solution, and the mixture was extracted with ethyl acetate. The extract was dried over sodium sulfate, and the solvent was evaporated under reduced pressure to give a carboxylic acid compound 3-(2-phenoxyethoxy)thiophene-2-carboxylic acid (1.491 g, 5.64 mmol, yield 97%).

To a solution of the obtained 3-(2-phenoxyethoxy)thiophene-2-carboxylic acid (0.661 g, 2.50 mmol) in toluene (10 ml) were added oxalyl chloride (0.24 ml, 2.75 mmol) and N,N-dimethylformamide (0.01 ml), and the mixture was stirred at room temperature for 2 hr. N,N-Dimethylhydrazine (0.95 ml, 12.4 mmol) was added under ice-cooling, and the mixture was stirred at room temperature for 21 hr. The reaction mixture was washed with water, and the organic layer was dried over sodium sulfate. The solvent was evaporated under reduced pressure, and the obtained residue was purified by silica gel column chromatography (hexane:ethyl acetate) to give an acylhydrazine compound 3-(2-phenoxyethoxy)thiophene-2-carboxylic acid N',N'-dimethylhydrazide (0.739 g, 2.41 mmol, yield 96%) as a white powder.

The obtained acylhydrazine compound 3-(2-phenoxyethoxy)thiophene-2-carboxylic acid N',N'-dimethylhydrazide (0.733 g, 2.39 mmol) was dissolved in 1,2-dichloroethane (7 ml), phosphorus oxychloride (0.67 ml, 7.19 mmol) was added, and the mixture was stirred at 80° C. for 3 hr. The reaction solvent was evaporated under reduced pressure, imidazole (0.815 g, 12.0 mmol) and triethylamine (0.75 ml, 5.42 mmol) were added to a solution of the residue in 1,2-dichloroethane (8 ml), and the mixture was stirred at 80° C. for 5 hr. The reaction mixture was washed with water, the organic layer was dried over sodium sulfate and evaporated under reduced pressure. The residue was purified by silica gel column chromatography (hexane:ethyl acetate) to give the object compound (0.157 g, 0.44 mmol, yield 18%) as a yellow liquid.

$^1$H-NMR spectrum (CDCl$_3$) δppm: 2.58 (6H, s), 4.03 (2H, t, J=5.5 Hz), 4.27 (2H, t, J=5.0 Hz), 6.83 (2H, d, J=7.8 Hz), 6.89 (1H, d, J=6.0 Hz), 6.96 (1H, t, J=7.3 Hz), 6.99 (1H, s), 7.21 (1H, s), 7.27 (2H, t, J=7.3 Hz), 7.50 (1H, d, J=5.5 Hz), 7.71 (1H, s).

Mass spectrum m/z (FAB): 357 (M$^+$+1)

Example 102

N'-(1-imidazol-1-yl-1-pyrrol-2-ylmethylidene)-N,N-dimethylhydrazine (Compound Nos. 102, 103)

To a solution of pyrrole-2-carboxylic acid (4.366 g, 39.3 mmol) in 1,2-dichloroethane (40 ml) were added oxalyl chloride (3.77 ml, 43.2 mmol) and N,N-dimethylformamide (0.01 ml), and the mixture was stirred at room temperature for 3 hr. The reaction solvent was evaporated under reduced pressure, and the residue was dissolved in 1,2-dichloroethane (40 ml). N,N-Dimethylhydrazine (3.30 ml, 43.2 mmol) and N-methylmorpholine (5.62 ml, 51.1 mmol) were added under ice-cooling, and the mixture was stirred at room temperature for 3 hr. The reaction mixture was washed with water, and the organic layer was dried over sodium sulfate. The solvent was evaporated under reduced pressure, and the obtained residue was purified by silica gel column chromatography (hexane:ethyl acetate) to give an acylhydrazine compound pyrrole-2-carboxylic acid N',N'-dimethylhydrazide (4.75 g, 31.0 mmol, yield 79%).

The obtained acylhydrazine compound (3.07 g, 20.0 mmol) was dissolved in 1,2-dichloroethane (60 ml), phosphorus oxychloride (5.60 ml, 60.0 mmol) was added, and the mixture was stirred at 80° C. for 1.5 hr. 1,2-Dichloroethane (60 ml), imidazole (6.810 g, 100.0 mmol) and triethylamine (6.10 ml, 44.0 mmol) were added, and the mixture was stirred at 80° C. for 5 hr. The reaction mixture was washed with water, and the organic layer was dried over sodium sulfate and evaporated under reduced pressure. The residue was purified by silica gel column chromatography (hexane:ethyl acetate) to give the Compound No. 103 (lower polar isomer, 0.329 g, 1.62 mmol, yield 8%), and the Compound No. 102 (higher polar isomer, 1.262 g, 6.21 mmol, yield 31%) as a pale-yellow powder.

Compound No. 102

$^1$H-NMR spectrum (CDCl$_3$) δppm: 2.59 (6H, s), 6.26-6.28 (1H, m), 6.45-6.46 (1H, m), 7.07 (1H, m), 7.12 (1H, s), 7.35 (1H, d, J=1.4 Hz), 7.94 (1H, d, J=0.9 Hz), 11.84 (1H, br s).

Mass spectrum m/z (FAB): 204 (M$^+$+1)

Compound No. 103

$^1$H-NMR spectrum (CDCl$_3$) δppm: 2.43 (6H, d, J=0.9 Hz), 6.14 (1H, m), 6.20-6.22 (1H, m), 6.90 (1H, m), 7.18 (1H, s), 7.30 (1H, s), 7.86 (1H, s), 9.07 (1H, br s).

Mass spectrum m/z (FAB): 204 (M$^+$+1)

Example 103

N'-[1-(1-hexylpyrrol-2-yl)-1-imidazol-1-ylmethylidene]-N,N-dimethylhydrazine (Compound No. 104)

To a solution of methylpyrrole-2-carboxylate (1.01 g, 8.07 mmol) in N,N-dimethylformamide (12 ml) were added 1-bromohexane (1.36 ml, 9.69 mmol) and potassium carbonate (1.474 g, 10.7 mmol), and the mixture was stirred at 80° C. for 20 hr. Ethyl acetate was added to the reaction mixture, the mixture was washed with water, and the organic layer was dried over sodium sulfate. The solvent was evaporated under reduced pressure, and the obtained residue was purified by silica gel column chromatography (hexane:ethyl acetate) to give methyl 1-hexylpyrrole-2-carboxylate (0.980 g, 4.68 mmol, yield 58%). This was dissolved in methanol (8 ml), 1N-aqueous sodium hydroxide solution (8 ml) was added at room temperature, and the mixture was stirred at 60° C. for 20 hr. The reaction mixture was concentrated under reduced pressure and neutralized with 1N-aqueous hydrochloric acid solution, and the mixture was extracted with ethyl acetate. The extract was dried over sodium sulfate, and the solvent was evaporated under reduced pressure to give a carboxylic acid compound 1-hexylpyrrole-2-carboxylic acid (0.877 g, 4.49 mmol, yield 96%).

To a solution of the obtained 1-hexylpyrrole-2-carboxylic acid (0.148 g, 0.76 mmol) in 1,2-dichloroethane (3 ml) were added oxalyl chloride (0.08 ml, 0.92 mmol) and N,N-dimethylformamide (0.01 ml), and the mixture was stirred at room temperature for 3 hr. The reaction solvent was evaporated under reduced pressure, and the residue was dissolved in 1,2-dichloroethane (3 ml). N,N-Dimethylhydrazine (0.07 ml, 0.92 mmol) and N-methylmorpholine (0.11 ml, 1.00 mmol) were added under ice-cooling, and the mixture was stirred at room temperature for 20 hr. The reaction mixture was washed with water, and the organic layer was dried over sodium sulfate. The solvent was evaporated under reduced pressure, and the obtained residue was purified by silica gel column chromatography (hexane:ethyl acetate) to give an acylhydrazine compound 1-hexylpyrrole-2-carboxylic acid N',N'-dimethylhydrazide (0.152 g, 0.64 mmol, yield 84%) as a white powder.

The obtained acylhydrazine compound (0.152 g, 0.641 mmol) was dissolved in toluene (3 ml), phosphorus oxychloride (0.7 ml) was added, and the mixture was stirred at 60° C. for 0.5 hr. The reaction solvent was evaporated under reduced pressure, imidazole (0.226 g, 3.32 mmol) and triethylamine (0.54 ml, 3.88 mmol) were added to a solution of the residue in 1,2-dichloroethane (4 ml), and the mixture was stirred at 60° C. for 5 hr. The reaction mixture was washed with water, and the organic layer was dried over sodium sulfate and evaporated under reduced pressure. The residue was purified by silica gel column chromatography (hexane:ethyl acetate) to give the object compound (0.045 g, 0.156 mmol, yield 24%) as a yellow liquid.

$^1$H-NMR spectrum (CDCl$_3$) δppm: 0.82-0.91 (3H, m), 1.18-1.25 (4H, m), 1.60-1.79 (4H, m), 2.44, 2.51 (6H, s each), 3.85, 4.21 (2H, t each, J=7.3 Hz), 6.00-6.28 (2H, m), 6.78-6.83 (1H, m), 7.05, 7.14 (1H, s each), 7.24-7.31 (1H, m), 7.77, 7.78 (1H, s each).

Mass spectrum m/z (FAB): 288 (M$^+$+1)

Example 104

N'-[1-(1-benzylpyrrol-2-yl)-1-imidazol-1-ylmethylidene]-N,N-dimethylhydrazine
(Compound No. 105)

In the same manner as in Example 103, the object compound was obtained as a mixture of geometric isomers (yellow liquid, yield from acylhydrazine compound 19%).

$^1$H-NMR spectrum (CDCl$_3$) δppm: 2.23, 2.52 (6H, s each), 5.08, 5.53 (2H, s each), 6.07-6.31 (2H, m), 6.87-6.89 (1H, m), 6.96-7.13 (4H, m), 7.20-7.32 (3H, m), 7.57, 7.67 (1H, s each).

Mass spectrum m/z (FAB): 294 (M$^+$+1)

Example 105

N'-[1-imidazol-1-yl-1-[1-(4-methoxybenzyl)pyrrol-2-yl]methylidene]-N,N-dimethylhydrazine
(Compound No. 106)

In the same manner as in Example 103, the object compound was obtained as a mixture of geometric isomers (yellow liquid, yield from acylhydrazine compound 59%).

$^1$H-NMR spectrum (CDCl$_3$) δppm: 2.29, 2.52 (6H, d each, J=0.9 Hz), 3.74, 3.78 (3H, s each), 5.00, 5.45 (2H, s each), 6.06-6.29 (2H, m), 6.75-7.15 (7H, m), 7.59, 7.68 (1H, d each, J=0.9 Hz).

Mass spectrum m/z (FAB): 324 (M$^+$+1)

Example 106

N'-[1-imidazol-1-yl-1-[1-(2-phenoxyethyl)pyrrol-2-yl]methylidene]-N,N-dimethylhydrazine
(Compound No. 107)

In the same manner as in Example 103, the object compound was obtained as a mixture of geometric isomers (yellow liquid, yield from acylhydrazine compound 58%).

$^1$H-NMR spectrum (CDCl$_3$) δppm: 2.43, 2.50 (6H, s each), 4.08, 4.33 (2H, t each, J=5.0 Hz), 4.31, 4.68 (2H, t each, J=5.5 Hz), 6.02-6.11 (1H, m), 6.25-6.28 (1H, m), 6.70, 6.86 (2H, d each, J=7.8 Hz), 6.91-7.00 (2H, m), 7.05, 7.14 (1H, s each), 7.21-7.33 (3H, m), 7.78, 7.81 (1H, s each).

Mass spectrum m/z (FAB): 324 (M$^+$+1)

Example 107

N'-[1-imidazol-1-yl-1-[1-(3-phenoxypropyl)pyrrol-2-yl]methylidene]-N,N-dimethylhydrazine
(Compound No. 108)

In the same manner as in Example 103, the object compound was obtained as a mixture of geometric isomers (yellow liquid, yield from acylhydrazine compound 62%).

$^1$H-NMR spectrum (CDCl$_3$) δppm: 2.05, 2.29 (2H, quin each, J=6.4 Hz), 2.45, 2.52 (6H, s each), 3.82, 3.95 (2H, t each, J=6.0 Hz), 4.14, 4.78 (2H, t each, J=6.9 Hz), 6.01-6.07 (1H, m), 6.21-6.30 (1H, m), 6.78-6.84 (2H, m), 6.89-6.98 (2H, m), 7.03, 7.14 (1H, s each), 7.21-7.32 (3H, m), 7.77, 7.78 (1H, s each).

Mass spectrum m/z (FAB): 338 (M$^+$+1)

Example 108

N'-[1-[1-[2-(4-chlorophenyl)thiazol-4-ylmethyl]pyrrol-2-yl]-1-imidazol-1-ylmethylidene]-N,N-dimethylhydrazine (Compound No. 109)

In the same manner as in Example 103, the object compound was obtained as a mixture of geometric isomers (yellow liquid, yield from acylhydrazine compound 57%).

$^1$H-NMR spectrum (CDCl$_3$) δppm: 2.31, 2.54 (6H, s each), 5.25, 5.69 (2H, s each), 6.08-6.31 (2H, m), 6.75, 6.83 (1H, s each), 6.97-7.24 (3H, m), 7.36-7.42 (2H, m), 7.70-7.76 (2H, m), 7.85-7.87 (1H, m).

Mass spectrum m/z (FAB): 411 (M$^+$+1)

Example 109

N'-[1-[1-(2,4-dichlorobenzyl)pyrrol-3-yl]-1-imidazol-1-ylmethylidene]-N,N-dimethylhydrazine
(Compound No. 110)

In the same manner as in Example 103, the object compound was obtained (yellow liquid, yield from acylhydrazine compound 10%).

$^1$H-NMR spectrum (CDCl$_3$) δppm: 2.56 (6H, s), 5.16 (2H, s), 6.56 (1H, dd, J=2.7, 1.8 Hz), 6.69 (1H, t, J=2.7 Hz), 6.83 (1H, d, J=8.7 Hz), 7.07 (1H, s), 7.24 (1H, dd, J=8.7, 1.8 Hz), 7.31 (1H, s), 7.37 (1H, t, J=1.8 Hz), 7.44 (1H, d, J=1.8 Hz), 7.86 (1H, s).

Mass spectrum m/z (FAB): 362 (M$^+$+1)

Example 110

N'-[1-imidazol-1-yl-1-[1-(2-phenoxyethyl)imidazol-2-yl]methylidene]-N,N-dimethylhydrazine
(Compound Nos. 111, 112)

To a solution of ethyl imidazole-2-carboxylate (0.505 g, 3.60 mmol) in N,N-dimethylformamide (6 ml) were added β-bromophenetole (0.804 g, 4.00 mmol) and potassium carbonate (0.598 g, 4.32 mmol), and the mixture was stirred at 80° C. for 1 hr. Ethyl acetate was added to the reaction mixture, the mixture was washed with water, and the organic layer was dried over sodium sulfate. The solvent was evaporated under reduced pressure, and the obtained residue was purified by silica gel column chromatography (hexane:ethyl acetate) to give ethyl 1-(2-phenoxyethyl)imidazole-2-carboxylate (0.869 g, 3.34 mmol, yield 93%). This was dissolved in methanol (9 ml), 1N-aqueous sodium hydroxide solution (9 ml) was added at room temperature, and the mixture was stirred at 60° C. for 3 hr. The reaction mixture was concentrated under reduced pressure and neutralized with 5%-aqueous citric acid solution, and the mixture was extracted with ethyl acetate. The extract was dried over sodium sulfate, and the solvent was evaporated under reduced pressure to give a carboxylic acid compound 1-(2-phenoxyethyl)imidazole-2-carboxylic acid (0.573 g, 2.47 mmol, yield 74%).

The obtained carboxylic acid compound (0.573 g, 2.47 mmol) was dissolved in N,N-dimethylformamide (7 ml), 1-ethyl-3-(3-dimethylaminopropyl)carbodiimide hydrochloride (0.576 g, 3.00 mmol), 1-hydroxybenzotriazole (0.460 g, 3.00 mmol) and N,N-dimethylhydrazine (0.21 ml, 2.76 mmol) were successively added under ice-cooling, and the mixture was stirred at room temperature for 16 hr. Ethyl acetate was added to the reaction mixture, the mixture was washed successively with saturated aqueous sodium hydrogen carbonate solution and water, and the organic layer was dried over sodium sulfate. The solvent was evaporated under reduced pressure, and the obtained residue was purified by silica gel column chromatography (hexane:ethyl acetate) to give an acylhydrazine compound 1-(2-phenoxyethyl)imidazole-2-carboxylic acid N',N'-dimethylhydrazide (0.444 g, 1.62 mmol, yield 66%).

To the obtained acylhydrazine compound (0.208 g, 0.747 mmol) was added phosphorus oxychloride (1.0 ml), and the mixture was stirred at 60° C. for 2 hr. The reaction solvent was evaporated under reduced pressure, imidazole (0.509 g, 7.48 mmol) was added to a solution of the residue in N,N-dimethylformamide (7 ml), and the mixture was stirred at 100° C. for 14 hr. The reaction mixture was washed with water, and the organic layer was dried over sodium sulfate and evaporated under reduced pressure. The residue was purified by silica gel column chromatography (hexane:ethyl acetate) to give the Compound No. 111 (lower polar isomer, 0.016 g, 0.05 mmol, yield 7%), and the Compound No. 112 (higher polar isomer, 0.009 g, 0.03 mmol, yield 4%) as a yellow liquid.

Compound No. 111

$^1$H-NMR spectrum (CDCl$_3$) δppm: 2.57 (6H, s), 4.13 (2H, t, J=5.0 Hz), 4.33 (2H, t, J=5.0 Hz), 6.69 (2H, d, J=8.7 Hz), 6.94-6.97 (1H, m), 7.06 (1H, s), 7.21-7.31 (5H, m), 7.77 (1H, s).

Mass spectrum m/z (FAB): 325 (M$^+$+1)

Compound No. 112

$^1$H-NMR spectrum (CDCl$_3$) δppm: 2.59 (6H, s), 4.33 (2H, t, J=5.0 Hz), 4.70 (2H, t, J=5.0 Hz), 6.86 (2H, d, J=7.8 Hz), 6.98 (1H, t, J=7.3 Hz), 7.05 (1H, d, J=0.9 Hz), 7.13 (1H, d, J=0.9 Hz), 7.17 (1H, s), 7.23-7.31 (3H, m), 7.84 (1H, s).

Mass spectrum m/z (FAB): 325 (M$^+$+1)

Example 111

N-ethyl-N'-[1-[2-(4-fluorobenzyloxy)phenyl]-1-imidazol-1-ylmethylidene]-N-methylhydrazine
(Compound No. 113)

Carboxylic acid compound 2-(4-fluorobenzyloxy)benzoic acid (1.512 g, 6.14 mmol) was dissolved in N,N-dimethylformamide (25 ml), N-methylmorpholine (0.81 ml, 7.37 mmol), tert-butyl carbazate (0.893 g, 6.75 mmol), 1-hydroxybenzotriazole (1.080 g, 7.98 mmol) and 1-ethyl-3-(3-dimethylaminopropyl)carbodiimide hydrochloride (1.530 g, 7.98 mmol) were successively added at room temperature, and the mixture was stirred for 20 hr. Ethyl acetate was added to the reaction mixture, the mixture was washed successively with saturated aqueous sodium hydrogen carbonate solution and water, and the organic layer was dried over sodium sulfate. The solvent was evaporated under reduced pressure, and the obtained residue was dissolved in dioxane (10 ml). 4N-hydrogen chloride/dioxane solution (10 ml) was added, and the mixture was stirred at room temperature for 9 hr. The reaction mixture was evaporated under reduced pressure to give 2-(4-fluorobenzyloxy)benzohydrazide hydrochloride (2.427 g).

The obtained 2-(4-fluorobenzyloxy)benzohydrazide hydrochloride (0.740 g, 2.84 mmol) was dissolved in methanol (7.0 ml), acetaldehyde (1.77 ml, 28.4 mmol) was added, and the mixture was stirred at room temperature for 3 hr. The reaction mixture was evaporated under reduced pressure and dissolved in methanol (6.5 ml). 36% Formalin (0.711 g, 8.52 mmol), sodium cyanoborohydride (0.892 g, 14.2 mmol) and acetic acid (0.2 ml) were added, and the mixture was stirred at room temperature for 8 hr. The reaction mixture was concentrated under reduced pressure, and ethyl acetate was added. The mixture was washed with water, and the organic layer was dried over sodium sulfate. The solvent was evaporated under reduced pressure, and the obtained residue was purified by silica gel column chromatography (hexane:ethyl acetate) to give an acylhydrazine compound N'-ethyl-N'-methyl-2-(4-fluorobenzyloxy)benzohydrazide (0.331 g, 1.09 mmol, yield 39%).

Using the obtained acylhydrazine compound and in the same manner as in Example 3, the object compound was obtained (yellow liquid, yield from acylhydrazine compound 45%).

$^1$H-NMR spectrum (CDCl$_3$) δppm: 1.02 (2H, t, J=7.3 Hz), 2.35 (3H, s), 2.83 (2H, q, J=6.9 Hz), 4.98 (2H, s), 6.96-7.11 (7H, m), 7.29 (1H, s), 7.37 (1H, d, J=7.3 Hz), 7.43-7.47 (1H, m), 7.60 (1H, s).

Mass spectrum m/z (FAB): 353 (M$^+$+1)

Example 112

N-ethyl-N'-[1-imidazol-1-yl-1-[2-(2-phenoxyethoxy)phenyl]methylidene]-N-methylhydrazine
(Compound No. 114)

In the same manner as in Example 111, the object compound was obtained (yellow liquid, yield from acylhydrazine compound 36%).

$^1$H-NMR spectrum (CDCl$_3$) δppm: 1.03 (3H, t, J=7.1 Hz), 2.35 (3H, s), 2.81 (2H, q, J=7.1 Hz), 4.08 (2H, t, J=4.8 Hz), 4.28 (2H, br), 6.81 (2H, d, J=8.2 Hz), 6.95 (1H, t, J=7.3 Hz), 7.00 (1H, s), 7.08 (2H, dd, J=14.9, 8.2 Hz), 7.24-7.28 (3H, m), 7.34 (1H, dd, J=7.3, 1.4 Hz), 7.45-7.49 (1H, m), 7.57 (1H, s).

Mass spectrum m/z (FAB): 365 (M$^+$+1)

Example 113

N-ethyl-N'-[1-imidazol-1-yl-1-[2-(3-phenoxypropoxy)phenyl]methylidene]-N-methylhydrazine
(Compound No. 115)

In the same manner as in Example 111, the object compound was obtained (yellow liquid, yield from acylhydrazine compound 57%).
$^1$H-NMR spectrum (CDCl$_3$) δppm: 1.02 (3H, t, J=7.3 Hz), 2.04 (2H, quin, J=6.0 Hz), 2.80 (2H, q, J=7.3 Hz), 3.83 (2H, t, J=6.0 Hz), 4.11 (2H, br), 6.80-6.83 (2H, m), 6.93 (1H, t, J=7.3 Hz), 6.97 (1H, s), 7.01 (1H, d, J=8.2 Hz), 7.06 (1H, t, J=7.3 Hz), 7.24-7.29 (3H, m), 7.34 (1H, d, J=7.8 Hz), 7.45 (1H, t, J=8.2 Hz), 7.61 (1H, s).
Mass spectrum m/z (FAB): 379 (M$^+$+1)

Example 114

N-ethyl-N'-[1-imidazol-1-yl-1-[2-(4-phenoxybutoxy)phenyl]methylidene]-N-methylhydrazine
(Compound No. 116)

In the same manner as in Example 111, the object compound was obtained (yellow liquid, yield from acylhydrazine compound 41%).
$^1$H-NMR spectrum (CDCl$_3$) δppm: 1.05 (3H, t, J=7.0 Hz), 1.62-1.69 (2H, m), 1.74-1.80 (2H, m), 2.36 (3H, s), 2.83 (2H, q, J=7.1 Hz), 3.86 (2H, t, J=6.0 Hz), 3.98 (2H, br), 6.84-6.86 (2H, m), 6.93 (1H, t, J=7.3 Hz), 6.98 (1H, d, J=8.2 Hz), 7.01 (1H, s), 7.06 (1H, t, J=7.6 Hz), 7.25-7.29 (3H, m), 7.35 (1H, dd, J=7.1, 1.8 Hz), 7.42-7.47 (1H, m), 7.57 (1H, s).
Mass spectrum m/z (FAB): 393 (M$^+$+1)

Example 115

N,N-diethyl-N'-[1-[2-(4-fluorobenzyloxy)phenyl]-1-imidazol-1-ylmethylidene]hydrazine
(Compound No. 117)

In the same manner as in Example 111, the object compound was obtained (yellow liquid, yield from acylhydrazine compound 45%).
$^1$H-NMR spectrum (CDCl$_3$) δppm: 0.90 (6H, t, J=7.3 Hz), 2.72-2.80 (4H, m), 4.96 (2H, s), 6.95-7.11 (4H, m), 7.31 (1H, s), 7.39 (1H, dd, J=7.6, 1.8 Hz), 7.42-7.46 (1H, m), 7.62 (1H, s).
Mass spectrum m/z (FAB): 367 (M$^+$+1)

Example 116

N'-[1-[2-(4-chlorobenzyloxy)phenyl]-1-imidazol-1-ylmethylidene]-N,N-diethylhydrazine
(Compound No. 118)

In the same manner as in Example 111, the object compound was obtained (yellow liquid, yield from acylhydrazine compound 36%).
$^1$H-NMR spectrum (CDCl$_3$) δppm: 0.91 (6H, t, J=7.3 Hz), 2.74-2.81 (4H, m), 4.97 (2H, s), 7.01 (2H, dd, J=8.5, 2.7 Hz), 7.04 (1H, s), 7.09 (1H, t, J=7.1 Hz), 7.25-7.27 (3H, m), 7.32 (1H, s), 7.39 (1H, dd, J=7.6, 1.8 Hz), 7.42-7.46 (1H, m), 7.62 (1H, s).
Mass spectrum m/z (FAB): 383 (M$^+$+1)

Example 117

N,N-diethyl-N'-[1-imidazol-1-yl-1-[2-(2-phenoxyethoxy)phenyl]methylidene]hydrazine
(Compound No. 119)

In the same manner as in Example 111, the object compound was obtained (yellow liquid, yield from acylhydrazine compound 30%).
$^1$H-NMR spectrum (CDCl$_3$) δppm: 0.92 (6H, t, J=7.3 Hz), 2.75 (4H, q, J=7.3 Hz), 4.06 (2H, t, J=5.0 Hz), 4.26 (2H, br), 6.80 (2H, d, J=7.8 Hz), 6.95 (1H, t, J=7.3 Hz), 7.00 (1H, s), 7.04-7.13 (2H, m), 7.24-7.28 (3H, m), 7.37 (1H, dd, J=7.6, 1.8 Hz), 7.44-7.48 (1H, m), 7.60 (1H, s).
Mass spectrum m/z (FAB): 379 (M$^+$+1)

Example 118

N,N-diethyl-N'-[1-imidazol-1-yl-1-[2-(3-phenoxypropoxy)phenyl]methylidene]hydrazine
(Compound No. 120)

In the same manner as in Example 111, the object compound was obtained (yellow liquid, yield from acylhydrazine compound 58%).
$^1$H-NMR spectrum (CDCl$_3$) δppm: 0.90 (6H, t, J=7.1 Hz), 2.02 (2H, quin, J=6.0 Hz), 2.72 (4H, q, J=7.3 Hz), 3.80 (2H, t, J=6.0 Hz), 4.10 (2H, br), 6.81 (2H, d, J=8.7 Hz), 6.91-6.95 (1H, m), 6.97 (1H, s), 7.00 (1H, d, J=8.2 Hz), 7.06 (1H, t, J=7.8 Hz), 7.25-7.29 (3H, m), 7.37 (1H, d, J=7.3 Hz), 7.44 (1H, t, J=8.2 Hz), 7.64 (1H, s).
Mass spectrum m/z (FAB): 393 (M$^+$+1)

Example 119

N'-[1-(2-chlorophenyl)-1-imidazol-1-ylmethylidene]-N,N-dipropylhydrazine
(Compound No. 121)

In the same manner as in Example 111, the object compound was obtained (yellow liquid, yield from acylhydrazine compound 69%).
$^1$H-NMR spectrum (CDCl$_3$) δppm: 0.70 (6H, t, J=7.3 Hz), 1.32-1.48 (4H, m), 2.60-2.80 (4H, m), 7.05 (1H, s), 7.24 (1H, s), 7.35-7.53 (4H, m), 7.59 (1H, s).
Mass spectrum m/z (FAB): 305 (M$^+$+1)

Example 120

N'-[1-(2-chlorophenyl)-1-imidazol-1-ylmethylidene]-N-ethyl-N-hexylhydrazine
(Compound No. 122)

In the same manner as in Example 111, the object compound was obtained (yellow liquid, yield from acylhydrazine compound 62%).
$^1$H-NMR spectrum (CDCl$_3$) δppm: 0.85 (3H, t, J=7.3 Hz), 0.96 (3H, t, J=7.3 Hz), 1.00-1.45 (8H, m), 2.65-2.90 (4H, m), 7.06 (1H, dd, J=1.3, 1.0 Hz), 7.25 (1H, t, J=1.3 Hz), 7.30-7.50 (4H, m), 7.60 (1H, t, J=1.0 Hz).
Mass spectrum m/z (FAB): 333 (M$^+$+1)

Example 121

N'-[1-(2-chlorophenyl)-1-imidazol-1-ylmethylidene]-N-hexyl-N-propylhydrazine
(Compound No. 123)

In the same manner as in Example 111, the object compound was obtained (yellow liquid, yield from acylhydrazine compound 69%).
$^1$H-NMR spectrum (CDCl$_3$) δppm: 0.71 (3H, t, J=7.3 Hz), 0.85 (3H, t, J=7.3 Hz), 1.00-1.45 (10H, m), 2.60-2.85 (4H, m), 7.05 (1H, s), 7.24 (1H, s), 7.40-7.55 (4H, m), 7.60 (1H, s).
Mass spectrum m/z (FAB): 347 (M$^+$+1)

Example 122

N'-[1-(2-chlorophenyl)-1-imidazol-1-ylmethylidene]-N,N-dihexylhydrazine
(Compound No. 124)

In the same manner as in Example 111, the object compound was obtained (yellow liquid, yield from acylhydrazine compound 55%).
$^1$H-NMR spectrum (CDCl$_3$) δppm: 0.85 (6H, t, J=7.3 Hz), 1.00-1.45 (16H, m), 2.60-2.85 (4H, m), 7.05 (1H, s), 7.24 (1H, s), 7.40-7.55 (4H, m), 7.60 (1H, s).
Mass spectrum m/z (FAB): 389 (M$^+$+1)

Example 123

N'-[1-(2-chlorophenyl)-1-imidazol-1-ylmethylidene]-N-ethyl-N-(3-methylbutyl)hydrazine
(Compound No. 125)

In the same manner as in Example 111, the object compound was obtained (yellow liquid, yield from acylhydrazine compound 69%).
$^1$H-NMR spectrum (CDCl$_3$) δppm: 0.78 (6H, d, J=6.6 Hz), 0.97 (3H, t, J=7.3 Hz), 1.15-1.50 (3H, m), 2.65-2.90 (4H, m), 7.06 (1H, s), 7.25 (1H, s), 7.35-7.53 (4H, m), 7.60 (1H, s).
Mass spectrum m/z (FAB): 319 (M$^+$+1)

Example 124

N'-[1-(2-chlorophenyl)-1-imidazol-1-ylmethylidene]-N,N-bis(3-methylbutyl)hydrazine
(Compound No. 126)

In the same manner as in Example 111, the object compound was obtained (yellow liquid, yield from acylhydrazine compound 74%).
$^1$H-NMR spectrum (CDCl$_3$) δppm: 0.79 (12H, d, J=6.6 Hz), 1.18-1.58 (6H, m), 2.70-2.78 (4H, m), 7.05 (1H, s), 7.26 (1H, s), 7.40-7.52 (4H, m), 7.60 (1H, s).
Mass spectrum m/z (FAB): 361 (M$^+$+1)

Example 125

N'-[1-(2-chlorophenyl)-1-imidazol-1-ylmethylidene]-N-(2,2-dimethylpropyl)-N-ethylhydrazine
(Compound No. 127)

In the same manner as in Example 111, the object compound was obtained (yellow liquid, yield from acylhydrazine compound 78%).
$^1$H-NMR spectrum (CDCl$_3$) δppm: 0.77 (3H, t, J=6.9 Hz), 0.90 (9H, s), 2.60-2.90 (4H, m), 7.03 (1H, d, J=1.0 Hz), 7.18 (1H, d, J=1.0 Hz), 7.35-7.55 (4H, m), 7.57 (1H, d, J=1.0 Hz).
Mass spectrum m/z (FAB): 319 (M$^+$+1)

Example 126

N-cyclopentyl-N'-[1-imidazol-1-yl-1-[2-(2-phenoxyethoxy)phenyl]methylidene]-N-methylhydrazine
(Compound No. 128)

In the same manner as in Example 111, the object compound was obtained (yellow liquid, yield from acylhydrazine compound 41%).
$^1$H-NMR spectrum (CDCl$_3$) δppm: 1.50-1.76 (8H, m), 2.27 (3H, s), 3.23 (1H, quin, J=7.3 Hz), 4.08 (2H, t, J=5.0 Hz), 4.27 (2H, br), 6.80-6.82 (2H, m), 6.95 (1H, t, J=7.8 Hz), 6.99 (1H, s), 7.06 (1H, d, J=8.7 Hz), 7.08 (1H, t, J=7.8 Hz), 7.24-7.28 (3H, m), 7.33-7.35 (1H, m), 7.44-7.48 (1H, m), 7.57 (1H, s).
Mass spectrum m/z (FAB): 405 (M$^+$+1)

Example 127

N-(4-chlorobenzyl)-N'-[1-(2-chlorophenyl)-1-imidazol-1-ylmethylidene]-N-ethylhydrazine
(Compound No. 129)

2-Chlorobenzohydrazide hydrochloride (1.00 g, 4.86 mmol) obtained in the same manner as in Example 111 was dissolved in methanol (15 ml), 4-chlorobenzaldehyde (0.76 g, 5.41 mmol) was added, and the mixture was stirred at room temperature for 20 hr. The reaction mixture was evaporated under reduced pressure and dissolved in trifluoroacetic acid (20 ml), triethylsilane (1.71 ml, 10.71 mmol) was added, and the mixture was stirred for 6 hr under ice-cooling. Ethyl acetate was added to the reaction mixture, the mixture was washed successively with water, 1N-aqueous sodium hydroxide solution and water, and the organic layer was dried over sodium sulfate. The solvent was evaporated under reduced pressure, and hexane was added to the obtained residue. The precipitate was collected by filtration to give N'-(4-chlorobenzyl)-2-chlorobenzohydrazide (1.120 g). The obtained N'-(4-chlorobenzyl)-2-chlorobenzohydrazide (0.330 g, 1.12 mmol) here was dissolved in methanol (20 ml), acetaldehyde (0.09 ml, 1.60 mmol), sodium cyanoborohydride (0.216 g, 3.43 mmol) and acetic acid (0.2 ml) were added, and the mixture was stirred at room temperature for 8 hr. The reaction mixture was concentrated under reduced pressure, and ethyl acetate was added. The mixture was washed with water, and the organic layer was dried over sodium sulfate. The solvent was evaporated under reduced pressure, and the obtained residue was purified by silica gel column chromatography (hexane:ethyl acetate) to give an acylhydrazine compound N'-(4-chlorobenzyl)-N'-ethyl-2-chlorobenzohydrazide (0.196 g, 0.606 mmol, yield 42%).
Using the obtained acylhydrazine compound and in the same manner as in Example 1, the object compound was obtained (yellow liquid, yield from acylhydrazine compound 78%).
$^1$H-NMR spectrum (CDCl$_3$) δppm: 0.99 (3H, t, J=7.3 Hz), 2.74 (2H, q, J=7.32 Hz), 3.76 (1H, d, J=12.9 Hz), 3.83 (1H, d, J=12.9 Hz), 6.88 (2H, d, J=8.6 Hz), 7.08 (1H, d, J=1.0 Hz), 7.17 (2H, d, J=8.6 Hz), 7.20-7.53 (5H, m), 7.62 (1H, d, J=1.0 Hz).
Mass spectrum m/z (FAB): 373 (M$^+$+1)

Example 128

N'-[1-(2-chlorophenyl)-1-imidazol-1-ylmethylidene]-N-(2,4-dichlorobenzyl)-N-propylhydrazine (Compound No. 130)

In the same manner as in Example 127, the object compound was obtained (yellow liquid, yield from acylhydrazine compound 33%).
$^1$H-NMR spectrum (CDCl$_3$) δppm: 0.72 (3H, t, J=7.3 Hz), 1.35-1.60 (2H, m), 2.60-2.90 (2H, m), 3.99 (2H, s), 7.00-7.15 (4H, m), 7.25-7.50 (5H, m), 7.58 (1H, d, J=1.0 Hz).
Mass spectrum m/z (FAB): 421 (M$^+$+1)

Example 129

N'-[1-(2-chlorophenyl)-1-imidazol-1-ylmethylidene]-N-(2,4-dichlorobenzyl)-N-hexylhydrazine (Compound No. 131)

In the same manner as in Example 127, the object compound was obtained (yellow liquid, yield from acylhydrazine compound 69%).
$^1$H-NMR spectrum (CDCl$_3$) δppm: 0.85 (3H, t, J=6.6 Hz), 1.00-1.55 (10H, m), 2.60-2.90 (2H, m), 3.99 (2H, s), 7.00-7.50 (9H, m), 7.58 (1H, s).
Mass spectrum m/z (FAB): 463 (M$^+$+1)

Example 130

N'-[1-(2-chlorophenyl)-1-imidazol-1-ylmethylidene]-N-methyl-N-(4-methylbenzyl)hydrazine (Compound No. 132)

In the same manner as in Example 127, the object compound was obtained (yellow liquid, yield from acylhydrazine compound 72%).
$^1$H-NMR spectrum (CDCl$_3$) δppm: 2.32 (3H, s), 2.38 (3H, s), 3.92 (2H, s), 7.00-7.55 (10H, m), 7.58 (1H, t, J=1.0 Hz).
Mass spectrum m/z (FAB): 338 (M$^+$+1)

Example 131

N-ethyl-N'-[1-imidazol-1-yl-1-(2-methylphenyl)methylidene]-N-(4-trifluoromethylbenzyl)hydrazine (Compound No. 133)

In the same manner as in Example 127, the object compound was obtained (yellow liquid, yield from acylhydrazine compound 77%).
$^1$H-NMR spectrum (CDCl$_3$) δppm: 1.01 (3H, t, J=7.3 Hz), 2.13 (3H, s), 2.74 (2H, q, J=7.3 Hz), 3.80 (2H, d, J=12.5 Hz), 3.90 (2H, d, J=12.5 Hz), 7.03 (2H, d, J=8.3 Hz), 7.07 (1H, s), 7.20-7.45 (5H, m), 7.44 (2H, d, J=8.3 Hz), 7.61 (1H, s).
Mass spectrum m/z (FAB): 387 (M$^+$+1)

Example 132

N-(4-tert-butylbenzyl)-N'-[1-(2-chlorophenyl)-1-imidazol-1-ylmethylidene]-N-propylhydrazine (Compound No. 134)

In the same manner as in Example 127, the object compound was obtained (yellow liquid, yield from acylhydrazine compound 99%).
$^1$H-NMR spectrum (CDCl$_3$) δppm: 0.72 (3H, t, J=7.3 Hz), 1.29 (9H, s), 1.35-1.55 (2H, m), 2.60-2.75 (2H, m), 3.75 (1H, d, J=12.9 Hz), 3.84 (1H, d, J=12.9 Hz), 6.81 (2H, d, J=8.3 Hz), 7.07 (1H, s), 7.17-7.50 (7H, m), 7.62 (1H, s).
Mass spectrum m/z (FAB): 409 (M$^+$+1)

Example 133

N-ethyl-N'-[1-imidazol-1-yl-1-(2-methylphenyl)methylidene]-N-(4-methoxybenzyl)hydrazine (Compound No. 135)

In the same manner as in Example 127, the object compound was obtained (yellow liquid, yield from acylhydrazine compound 58%).
$^1$H-NMR spectrum (CDCl$_3$) δppm: 0.98 (3H, t, J=7.3 Hz), 2.15 (3H, s), 2.72 (2H, q, J=7.3 Hz), 3.69 (2H, d, J=9.9 Hz), 3.76 (3H, s), 3.79 (2H, d, J=9.9 Hz), 6.73 (2H, d, J=8.9 Hz), 6.83 (2H, d, J=8.9 Hz), 7.07 (1H, s), 7.20-7.44 (5H, m), 7.62 (1H, s).
Mass spectrum m/z (FAB): 349 (M$^+$+1)

Example 134

N'-[1-(2-chlorophenyl)-1-imidazol-1-ylmethylidene]-N-ethyl-N-(3-phenylpropyl)hydrazine (Compound No. 136)

In the same manner as in Example 111, the object compound was obtained (yellow liquid, yield from acylhydrazine compound 77%).
$^1$H-NMR spectrum (CDCl$_3$) δppm: 0.94 (4H, t, J=7.3 Hz), 1.60-1.80 (2H, m), 2.43 (2H, t, J=7.9 Hz), 2.65-2.90 (4H, m), 7.05-7.52 (11 Hz, m), 7.60 (1H, s).
Mass spectrum m/z (FAB): 367 (M$^+$+1)

Example 135

N'-[1-(2-chlorophenyl)-1-imidazol-1-ylmethylidene]-N,N-bis(3-phenylpropyl)hydrazine (Compound No. 137)

In the same manner as in Example 111, the object compound was obtained (yellow liquid, yield from acylhydrazine compound 63%).
$^1$H-NMR spectrum (CDCl$_3$) δppm: 1.70 (4H, q, J=7.9 Hz), 2.41 (4H, t, J=7.9 Hz), 2.77 (4H, q, J=7.9 Hz), 7.00-7.60 (17H, m).
Mass spectrum m/z (FAB): 457 (M$^+$+1)

Example 136

N'-[1-(2-chlorophenyl)-1-imidazol-1-ylmethylidene]-N-methyl-N-phenylhydrazine (Compound No. 138)

N-Methyl-N-phenylhydrazine (3.038 g, 24.87 mmol) was dissolved in 1,2-dichloroethane (30 ml), 2-chlorobenzoyl chloride (3.45 ml, 27.24 mmol) and N-methylmorpholine (2.79 ml, 27.55 mmol) were added under ice-cooling, and the mixture was stirred for 1 hr under ice-cooling. The reaction mixture was washed with water, and the organic layer was dried over sodium sulfate. The solvent was evaporated under reduced pressure, and the obtained residue was purified by silica gel column chromatography (hexane:ethyl acetate) to give an acylhydrazine compound N'-methyl-N-phenyl-2-chlorobenzohydrazide (5.542 g, 21.3 mmol, yield 85%) as a white powder.

The obtained acylhydrazine compound N'-methyl-N-phenyl-2-chlorobenzohydrazide (0.500 g, 1.92 mmol) was dissolved in 1,2-dichloroethane (12 ml), phosphorus pentachloride (0.446 g, 2.14 mmol) was added, and the mixture was stirred at 60° C. for 2.5 hr. The reaction mixture was evaporated under reduced pressure, imidazole (0.654 g, 9.61 mmol) and triethylamine (0.32 ml, 2.31 mmol) were added to a solution of the residue in 1,2-dichloroethane (30 ml), and the mixture was stirred at 60 to 70° C. for 5 hr. The reaction mixture was washed with water (50 ml), the organic layer was dried over sodium sulfate, and the solvent was evaporated under reduced pressure. The residue was purified by silica gel column chromatography (hexane:ethyl acetate) to give the object compound (0.480 g, 1.55 mmol, yield 81%) as a yellow liquid.

$^1$H-NMR spectrum (CDCl$_3$) δppm: 2.97 (3H, s), 6.94 (1H, t, J=7.3 Hz), 7.08-7.55 (10H, m), 7.65 (1H, s).

Mass spectrum m/z (FAB): 311 (M$^+$+1)

Example 137

N'-[1-[2-(4-chlorobenzyloxy)phenyl]-1-imidazol-1-ylmethylidene]-N-methyl-N-phenylhydrazine (Compound No. 139)

In the same manner as in Example 136, the object compound was obtained (yellow liquid, yield from acylhydrazine compound 16%).

$^1$H-NMR spectrum (CDCl$_3$) δppm: 2.92 (3H, s), 4.96 (2H, d, J=3.7 Hz), 6.91 (1H, t, J=7.3 Hz), 6.97-7.11 (7H, m), 7.20-7.28 (4H, m), 7.35 (1H, dd, J=7.6, 1.8 Hz), 7.38 (1H, s), 7.45-7.49 (1H, m), 7.71 (1H, s).

Mass spectrum m/z (FAB): 417 (M$^+$+1)

Example 138

N'-[1-imidazol-1-yl-1-(3-methylthiophen-2-yl)methylidene]-N-methyl-N-phenylhydrazine (Compound No. 140)

In the same manner as in Example 136, the object compound was obtained as a mixture of geometric isomers (yellow liquid, yield from acylhydrazine compound 44%).

$^1$H-NMR spectrum (CDCl$_3$) δppm: 2.01, 2.08 (3H, s each), 2.90, 3.01 (3H, s each), 6.89, 6.94 (2H, d each, J=5.3 Hz), 7.10-7.50 (7H, m), 7.75, 7.83 (1H, s each).

Mass spectrum m/z (FAB): 297 (M$^+$+1)

Example 139

N-(4-chlorophenyl)-N'-[1-(2-chlorophenyl)-1-imidazol-1-ylmethylidene]-N-methylhydrazine (Compound No. 141)

In the same manner as in Example 136, the object compound was obtained (yellow liquid, yield from acylhydrazine compound 71%).

$^1$H-NMR spectrum (CDCl$_3$) δppm: 2.94 (3H, s), 7.00-7.60 (10H, m), 7.67 (1H, s).

Mass spectrum m/z (FAB): 345 (M$^+$+1)

Example 140

N-(4-chlorophenyl)-N'-[1-(2,4-dichlorophenyl)-1-imidazol-1-ylmethylidene]-N-methylhydrazine (Compound No. 142)

In the same manner as in Example 136, the object compound was obtained (yellow liquid, yield from acylhydrazine compound 45%).

$^1$H-NMR spectrum (CDCl$_3$) δppm: 2.95 (3H, s), 7.00 (2H, d, J=9.2 Hz), 7.13 (1H, s), 7.20-7.43 (5H, m), 7.56 (1H, s), 7.69 (1H, s).

Mass spectrum m/z (FAB): 379 (M$^+$+1)

Example 141

N-(4-chlorophenyl)-N'-[1-imidazol-1-yl-1-(3-methylthiophen-2-yl)methylidene]-N-methylhydrazine (Compound No. 143)

In the same manner as in Example 136, the object compound was obtained (yellow liquid, yield from acylhydrazine compound 35%).

$^1$H-NMR spectrum (CDCl$_3$) δppm: 2.06 (3H, s), 2.97 (3H, s), 6.95 (1H, d, J=5.0 Hz), 7.07 (2H, d, J=9.2 Hz), 7.12 (1H, s), 7.24 (2H, d, J=9.2 Hz), 7.33 (1H, s), 7.52 (1H, d, J=5.0 Hz), 7.82 (1H, s).

Mass spectrum m/z (FAB): 331 (M$^+$+1)

Example 142

N-(4-chlorophenyl)-N'-[1-(2-chlorophenyl)-1-imidazol-1-ylmethylidene]-N-ethylhydrazine (Compound No. 144)

In the same manner as in Example 136, the object compound was obtained (yellow liquid, yield from acylhydrazine compound 7%).

$^1$H-NMR spectrum (CDCl$_3$) δppm: 1.01 (3H, t, J=7.3 Hz), 3.38 (2H, q, J=7.3 Hz), 6.87 (2H, d, J=8.9 Hz), 7.12 (1H, s), 7.15 (2H, d, J=8.9 Hz), 7.17-7.47 (5H, m), 7.67 (1H, s).

Mass spectrum m/z (FAB): 359 (M$^+$+1)

Example 143

N-(4-chlorophenyl)-N'-[1-(2-chlorophenyl)-1-imidazol-1-ylmethylidene]-N-propylhydrazine (Compound No. 145)

In the same manner as in Example 136, the object compound was obtained (yellow liquid, yield from acylhydrazine compound 46%).

$^1$H-NMR spectrum (CDCl$_3$) δppm: 0.77 (3H, t, J=7.6 Hz), 1.35-1.58 (2H, m), 3.25 (2H, t, J=7.6 Hz), 6.88 (2H, d, J=9.2 Hz), 7.11 (1H, s), (2H, d, J=9.2 Hz), 7.20-7.47 (5H, m), 7.66 (1H, s).

Mass spectrum m/z (FAB): 373 (M$^+$+1)

Example 144

N'-[1-(2-chlorophenyl)-1-imidazol-1-ylmethylidene]-N-(2,4-dichlorophenyl)-N-methylhydrazine (Compound No. 146)

In the same manner as in Example 136, the object compound was obtained (yellow liquid, yield from acylhydrazine compound 82%).

$^1$H-NMR spectrum (CDCl$_3$) δppm: 3.03 (3H, s), 7.09 (1H, s), 7.14 (1H, s), 7.25-7.36 (7H, m), 7.63 (1H, s).

Mass spectrum m/z (FAB): 379 (M$^+$+1)

Example 145

N'-[1-(2-chlorophenyl)-1-imidazol-1-ylmethylidene]-N-(4-isopropylphenyl)-N-methylhydrazine (Compound No. 147)

In the same manner as in Example 136, the object compound was obtained (yellow liquid, yield from acylhydrazine compound 67%).
$^1$H-NMR spectrum (CDCl$_3$) δppm: 1.23 (6H, d, J=6.9 Hz), 2.86 (1H, sep, J=6.9 Hz), 2.95 (3H, s), 7.04 (2H, d, J=8.6 Hz), 7.10 (1H, s), 7.14 (2H, d, J=8.6 Hz), 7.29-7.53 (5H, m), 7.67 (1H, s).
Mass spectrum m/z (FAB): 353 (M$^+$+1)

Example 146

N-(4-tert-butylphenyl)-N'-[1-(2-chlorophenyl)-1-imidazol-1-ylmethylidene]-N-ethylhydrazine (Compound No. 148)

In the same manner as in Example 136, the object compound was obtained (pale-yellow powder, yield from acylhydrazine compound 72%).
$^1$H-NMR spectrum (CDCl$_3$) δppm: 1.05 (3H, t, J=7.3 Hz), 1.26 (9H, s), 3.41 (2H, q, J=7.3 Hz), 6.87 (2H, d, J=8.6 Hz), 7.10 (1H, s), 7.16-7.38 (7H, m), 7.66 (1H, s).
Mass spectrum m/z (FAB): 381 (M$^+$+1)

Example 147

N-benzyl-N'-[1-[2-(4-chlorobenzyloxy)phenyl]-1-imidazol-1-ylmethylidene]-N-phenylhydrazine (Compound No. 149)

In the same manner as in Example 136, the object compound was obtained (yellow liquid, yield from acylhydrazine compound 21%).
$^1$H-NMR spectrum (CDCl$_3$) δppm: 4.58 (2H, d, J=10.5 Hz), 4.72 (2H, dd, J=43.7, 11.9 Hz), 6.74 (1H, d, J=8.7 Hz), 6.86-7.22 (18H, m), 7.40 (1H, s), 7.65 (1H, s).
Mass spectrum m/z (FAB): 493 (M$^+$+1)

Example 148

N'-[1-[2-(4-chlorobenzyloxy)phenyl]-1-imidazol-1-ylmethylidene]-N,N-diphenylhydrazine (Compound No. 150)

In the same manner as in Example 136, the object compound was obtained (pale-yellow powder, yield from acylhydrazine compound 27%).
$^1$H-NMR spectrum (CDCl$_3$) δppm: 4.56 (1H, d, J=11.9 Hz), 4.73 (1H, d, J=11.9 Hz), 6.82-7.71 (21H, m).
Mass spectrum m/z (FAB): 479 (M$^+$+1)

Example 149

N'-[1-(2-chlorophenyl)-1-imidazol-1-ylmethylidene]-N-ethyl-N-furan-3-ylmethylhydrazine (Compound No. 151)

In the same manner as in Example 127, the object compound was obtained (yellow liquid, yield from acylhydrazine compound 58%).
$^1$H-NMR spectrum (CDCl$_3$) δppm: 1.01 (3H, t, J=7.3 Hz), 2.76 (2H, q, J=7.3 Hz), 3.67 (2H, s), 5.95 (1H, d, J=1.0 Hz), 7.08 (1H, s), 7.17 (1H, s), 7.27-7.54 (6H, m), 7.63 (1H, s).
Mass spectrum m/z (FAB): 329 (M$^+$+1)

Example 150

[1-(2-chlorophenyl)-1-imidazol-1-ylmethylidene]pyrrolidin-1-ylamine (Compound No. 152)

In the same manner as in Example 1, the object compound was obtained (yellow liquid, yield from acylhydrazine compound 11%).
$^1$H-NMR spectrum (CDCl$_3$) δppm: 1.78-1.86 (4H, m), 3.04-3.12 (4H, m), 7.10 (1H, s), 7.17 (1H, d, J=1.4 Hz), 7.26-7.40 (4H, m), 7.80 (1H, s).
Mass spectrum m/z (FAB): 275 (M$^+$+1)

Example 151

[1-(2-hydroxyphenyl)-1-imidazol-1-ylmethylidene]pyrrolidin-1-ylamine (Compound No. 153)

In the same manner as in Example 13, the object compound was obtained (pale-yellow powder, yield from acylhydrazine compound 40%).
$^1$H-NMR spectrum (CDCl$_3$) δppm: 1.75-1.85 (4H, m), 2.95-3.04 (4H, m), 6.56 (1H, d, J=8.2 Hz), 6.75 (1H, t, J=8.2 Hz), 6.99 (1H, d, J=8.2 Hz), 7.11 (1H, s), 7.23 (1H, t, J=8.2 Hz), 7.26 (1H, s), 7.68 (1H, s), 11.49 (1H, s).
Mass spectrum m/z (FAB): 267 (M$^+$+1)

Example 152

[1-imidazol-1-yl-1-(2-propoxyphenyl)methylidene]pyrrolidin-1-ylamine (Compound No. 154, lower polar isomer)

In the same manner as in Example 1, the object compound was obtained (pale-yellow powder, yield from acylhydrazine compound 8%).
$^1$H-NMR spectrum (CDCl$_3$) δppm: 0.82 (3H, t, J=7.3 Hz), 1.47 (2H, sex, J=7.3 Hz), 1.74-1.84 (4H, m), 3.01 (4H, t, J=6.9 Hz), 3.71 (2H, t, J=7.3 Hz), 6.82 (1H, d, J=8.2 Hz), 6.96 (1H, t, J=8.2 Hz), 7.04 (1H, s), 7.22 (1H, s), 7.35 (1H, t, J=7.8 Hz), 7.43 (1H, dd, J=7.3, 1.8 Hz), 7.77 (1H, s).
Mass spectrum m/z (FAB): 299 (M$^+$+1)

Example 153

[1-imidazol-1-yl-1-(2-propoxyphenyl)methylidene]pyrrolidin-1-ylamine (Compound No. 155, higher polar isomer)

In the same manner as in Example 3, the object compound was obtained (yellow liquid, yield from acylhydrazine compound 35%).
$^1$H-NMR spectrum (CDCl$_3$) δppm: 0.80 (3H, t, J=7.3 Hz), 1.58 (2H, sex, J=7.3 Hz), 1.72 (4H, m), 2.95 (4H, br), 3.87 (2H, br), 6.93 (1H, d, J=6.9 Hz), 6.98 (1H, s), 7.02 (1H, t, J=7.3 Hz), 7.17 (1H, s), 7.38-7.44 (2H, m), 7.54 (1H, s).
Mass spectrum m/z (FAB): 299 (M$^+$+1)

Example 154

[1-imidazol-1-yl-1-(2-pentyloxyphenyl)methylidene]pyrrolidin-1-ylamine (Compound No. 156, lower polar isomer)

In the same manner as in Example 1, the object compound was obtained (yellow liquid, yield from acylhydrazine compound 12%).

$^1$H-NMR spectrum (CDCl$_3$) δppm: 0.88 (3H, t, J=6.8 Hz), 1.14-1.32 (4H, m), 1.45 (2H, quin, J=6.8 Hz), 1.75-1.82 (4H, m), 2.96-3.04 (4H, m), 3.74 (2H, t, J=6.8 Hz), 6.82 (1H, d, J=8.2 Hz), 6.95 (1H, td, J=7.3, 0.9 Hz), 7.04 (1H, s), 7.24 (1H, t, J=1.4 Hz), 7.35 (1H, td, J=7.8, 1.8 Hz), 7.42 (1H, dd, J=7.8, 1.8 Hz), 7.75 (1H, s).

Mass spectrum m/z (FAB): 327 (M$^+$+1)

Example 155

[1-imidazol-1-yl-1-(2-pentyloxyphenyl)methylidene]pyrrolidin-1-ylamine (Compound No. 157, higher polar isomer)

In the same manner as in Example 3, the object compound was obtained (yellow liquid, yield from acylhydrazine compound 44%).

$^1$H-NMR spectrum (CDCl$_3$) δppm: 0.85 (3H, t, J=6.9 Hz), 1.10-1.30 (4H, m), 1.55 (2H, quin, J=6.9 Hz), 1.72 (4H, m), 2.94 (4H, br s), 3.89 (2H, br), 6.93 (1H, d, J=6.9 Hz), 6.98 (1H, s), 7.01 (1H, t, J=7.3 Hz), 7.17 (1H, s), 7.38-7.43 (2H, m), 7.52 (1H, s).

Mass spectrum m/z (FAB): 327 (M$^+$+1)

Example 156

[1-[2-(4-fluorobenzyloxy)phenyl]-1-imidazol-1-ylmethylidene]pyrrolidin-1-ylamine (Compound No. 158)

In the same manner as in Example 3, the object compound was obtained (yellow liquid, yield from acylhydrazine compound 30%).

$^1$H-NMR spectrum (CDCl$_3$) δppm: 1.69-1.72 (4H, m), 2.94 (4H, d, J=4.6 Hz), 4.96 (2H, d, J=16.0 Hz), 6.96-7.08 (7H, m), 7.18 (1H, s), 7.40-7.44 (2H, m), 7.57 (1H, s).

Mass spectrum m/z (FAB): 365 (M$^+$+1)

Example 157

[1-[2-(3-fluorobenzyloxy)phenyl]-1-imidazol-1-ylmethylidene]pyrrolidin-1-ylamine (Compound No. 159)

In the same manner as in Example 36, carboxylic acid compound 2-(3-fluorobenzyloxy)benzoic acid was obtained. Then, in the same manner as in Example 3, the object compound was obtained (yellow liquid, yield from acylhydrazine compound 31%).

$^1$H-NMR spectrum (CDCl$_3$) δppm: 1.70-1.74 (4H, m), 2.96 (4H, s), 5.01 (2H, d, J=6.4 Hz), 6.86-6.89 (2H, m), 6.98 (2H, J=8.7 Hz), 7.04 (1H, s), 7.07 (1H, t, J=7.3 Hz), 7.21 (1H, s), 7.24-7.29 (1H, m), 7.40-7.44 (2H, m), 7.58 (1H, s).

Mass spectrum m/z (FAB): 365 (M$^+$+1)

Example 158

[1-imidazol-1-yl-1-[2-(2-phenoxyethoxy)phenyl]methylidene]pyrrolidin-1-ylamine (Compound No. 160, lower polar isomer)

In the same manner as in Example 1, the object compound was obtained (yellow liquid, yield from acylhydrazine compound 16%).

$^1$H-NMR spectrum (CDCl$_3$) δppm: 1.68-1.79 (4H, m), 2.99 (4H, t, J=6.9 Hz), 3.93 (2H, t, J=5.0 Hz), 4.10 (2H, t, J=5.0 Hz), 6.84-7.04 (6H, m), 7.18 (1H, s), 7.25-7.32 (2H, m), 7.37 (1H, td, J=7.8, 1.8 Hz), 7.46 (1H, dd, J=7.3, 1.8 Hz), 7.69 (1H, s).

Mass spectrum m/z (FAB): 377 (M$^+$+1)

Example 159

[1-imidazol-1-yl-1-[2-(2-phenoxyethoxy)phenyl]methylidene]pyrrolidin-1-ylamine (Compound No. 161, higher polar isomer)

In the same manner as in Example 3, the object compound was obtained (yellow liquid, yield from acylhydrazine compound 49%).

$^1$H-NMR spectrum (CDCl$_3$) δppm: 1.67 (4H, br s), 2.93 (4H, br t, J=6.8 Hz), 4.07 (2H, t, J=5.0 Hz), 4.25 (2H, br s), 6.83 (2H, d, J=8.7 Hz), 6.95 (1H, t, J=7.3 Hz), 6.97 (1H, s), 7.04 (1H, d, J=8.7 Hz), 7.06 (1H, t, J=7.3 Hz), 7.14 (1H, s), 7.26 (2H, t, J=8.7 Hz), 7.41 (1H, dd, J=7.3, 1.8 Hz), 7.44 (1H, td, J=7.3, 1.8 Hz), 7.54 (1H, s).

Mass spectrum m/z (FAB): 377 (M$^+$+1)

Example 160

[1-[2-[2-(4-fluorophenoxy)ethoxy]phenyl]-1-imidazol-1-ylmethylidene]pyrrolidin-1-ylamine (Compound No. 162)

In the same manner as in Example 36, carboxylic acid compound 2-[2-(4-fluorophenoxy)ethoxy]benzoic acid was obtained. Then, in the same manner as in Example 1, the object compound was obtained (yellow liquid, yield from acylhydrazine compound 40%).

$^1$H-NMR spectrum (CDCl$_3$) δppm: 1.62-1.74 (4H, m), 2.88-2.98 (4H, m), 4.03 (2H, t, J=5.0 Hz), 4.25 (2H, br s), 6.73-6.80 (2H, m), 6.92-7.10 (5H, m), 7.15 (1H, s), 7.40-7.50 (2H, m), 7.54 (1H, s).

Mass spectrum m/z (FAB): 395 (M$^+$+1)

Example 161

[1-[2-[2-(4-chlorophenoxy)ethoxy]phenyl]-1-imidazol-1-ylmethylidene]pyrrolidin-1-ylamine (Compound No. 163)

In the same manner as in Example 36, carboxylic acid compound 2-[2-(4-chlorophenoxy)ethoxy]benzoic acid was obtained. Then, in the same manner as in Example 1, the object compound was obtained (yellow liquid, yield from acylhydrazine compound 20%).

$^1$H-NMR spectrum (CDCl$_3$) δppm: 1.70-1.80 (4H, m), 2.95-3.04 (4H, m), 3.89 (2H, t, J=5.0 Hz), 4.08 (2H, t, J=5.0 Hz), 6.80 (2H, d, J=8.7 Hz), 6.87 (1H, d, J=8.2 Hz), 6.94 (1H, s), 7.01 (1H, t, J=7.3 Hz), 7.16 (1H, s), 7.24 (2H, d, J=8.7 Hz), 7.37 (1H, t, J=7.8 Hz), 7.47 (1H, d, J=7.8 Hz), 7.67 (1H, s).

Mass spectrum m/z (FAB): 411 (M$^+$+1)

Example 162

[1-imidazol-1-yl-1-[2-(3-phenoxypropoxy)phenyl]methylidene]pyrrolidin-1-ylamine (Compound No. 164)

In the same manner as in Example 36, carboxylic acid compound 2-(3-phenoxypropoxy)benzoic acid was obtained. Then, in the same manner as in Example 1, the object compound was obtained (yellow liquid, yield from acylhydrazine compound 52%).

$^1$H-NMR spectrum (CDCl$_3$) δppm: 1.62-1.68 (4H, m), 2.03-2.05 (2H, m), 2.89 (4H, br), 3.84 (2H, br), 4.06-4.16 (2H, m), 6.83 (2H, d, J=7.8 Hz), 6.91-6.99 (2H, m), 7.01-7.05 (1H, m), 7.13 (1H, s), 7.25-7.29 (3H, m), 7.39-7.44 (2H, m), 7.58 (1H, s).

Mass spectrum m/z (FAB): 391 (M$^+$+1)

Example 163

[1-imidazol-1-yl-1-[2-(4-phenoxybutoxy)phenyl]methylidene]pyrrolidin-1-ylamine (Compound No. 165)

In the same manner as in Example 36, carboxylic acid compound 2-(4-phenoxybutoxy)benzoic acid was obtained. Then, in the same manner as in Example 1, the object compound was obtained (yellow liquid, yield from acylhydrazine compound 30%).

$^1$H-NMR spectrum (CDCl$_3$) δppm: 1.63-1.80 (8H, m), 2.94 (4H, br), 3.82-3.92 (3H, m), 3.93 (1H, br), 6.86 (2H, d, J=8.7 Hz), 6.93-6.96 (1H, m), 6.98 (1H, s), 7.03 (1H, t, J=7.6 Hz), 7.17 (1H, s), 7.25-7.29 (3H, m), 7.41 (2H, d, J=7.3 Hz), 7.54 (1H, s).

Mass spectrum m/z (FAB): 405 (M$^+$+1)

Example 164

[1-(2-chlorophenyl)-1-imidazol-1-ylmethylidene]hexahydrocyclopenta[C]pyrrol-2-ylamine (Compound No. 166)

In the same manner as in Example 1, the object compound was obtained (yellow liquid, yield from acylhydrazine compound 19%).

$^1$H-NMR spectrum (CDCl$_3$) δppm: 1.10-1.80 (6H, m), 2.40-2.70 (4H, m), 2.90-3.05 (2H, m), 7.04 (1H, s), 7.19 (1H, s), 7.30-7.60 (5H, m).

Mass spectrum m/z (FAB): 315 (M$^+$+1)

Example 165

[1-imidazol-1-yl-1-(2-methylphenyl)methylidene]-(1,3-dihydroisoindol-2-yl)amine (Compound No. 167)

In the same manner as in Example 1, the object compound was obtained (yellow liquid, yield from acylhydrazine compound 18%).

$^1$H-NMR spectrum (CDCl$_3$) δppm: 2.24 (3H, s), 4.23 (2H, d, J=13.2 Hz), 4.30 (2H, d, J=13 Hz), 7.05-7.50 (10H, m), 7.60 (1H, s).

Mass spectrum m/z (FAB): 303 (M$^+$+1)

Example 166

[1-(2-bromophenyl)-1-imidazol-1-ylmethylidene]-(5-trifluoromethyl-1,3-dihydroisoindol-2-yl)amine (Compound No. 168)

In the same manner as in Example 1, the object compound was obtained (yellow liquid, yield from acylhydrazine compound 5%).

$^1$H-NMR spectrum (CDCl$_3$) δppm: 4.28-4.44 (4H, m), 7.08 (1H, s), 7.19 (1H, s), 7.25 (1H, d, J=8.2 Hz), 7.39 (1H, s), 7.40-7.60 (5H, m), 7.76 (1H, dd, J=8.2, 1.4 Hz).

Mass spectrum m/z (FAB): 435 (M$^+$+1)

Example 167

3-chloroindol-1-yl-[1-(2-chlorophenyl)-1-imidazol-1-ylmethylidene]amine (Compound No. 169)

In the same manner as in Example 136, the object compound was obtained as a mixture of geometric isomers (pale-yellow powder, yield from acylhydrazine compound 40%).

$^1$H-NMR spectrum (CDCl$_3$) δppm: 6.38 (1H, s), 7.19 (1H, s), 7.26 (1H, t, J=7.3 Hz), 7.38 (1H, t, J=7.3 Hz), 7.43-7.57 (4H, m), 7.61-7.68 (2H, m), 7.73 (1H, d, J=8.2 Hz), 7.74 (1H, s).

Mass spectrum m/z (FAB): 355 (M$^+$+1)

Example 168

[1-(2-chlorophenyl)-1-imidazol-1-ylmethylidene]piperidin-1-ylamine (Compound No. 170)

In the same manner as in Example 1, the object compound was obtained (pale-yellow powder, yield from acylhydrazine compound 35%).

$^1$H-NMR spectrum (CDCl$_3$) δppm: 1.30-1.55 (6H, m), 2.60-2.85 (4H, m), 7.07 (1H, s), 7.28 (1H, s), 7.35-7.55 (4H, m), 7.60 (1H, s).

Mass spectrum m/z (FAB): 289 (M$^+$+1)

Example 169

[1-(2-hydroxyphenyl)-1-imidazol-1-ylmethylidene]piperidin-1-ylamine (Compound No. 171)

In the same manner as in Example 13, the object compound was obtained (pale-yellow powder, yield from acylhydrazine compound 35%).

$^1$H-NMR spectrum (CDCl$_3$) δppm: 1.54 (2H, quin, J=5.5 Hz), 1.73 (4H, quin, J=5.5 Hz), 2.94 (4H, t, J=5.5 Hz), 6.89 (1H, t, J=7.3 Hz), 7.04-7.12 (3H, m), 7.18 (1H, s), 7.47 (1H, t, J=7.3 Hz), 7.81 (1H, s), 12.06 (1H, s).

Mass spectrum m/z (FAB): 271 (M$^+$+1)

Example 170

[1-(2-acetoxyphenyl)-1-imidazol-1-ylmethylidene]piperidin-1-ylamine (Compound No. 172)

In the same manner as in Example 1, the object compound was obtained (yellow liquid, yield from acylhydrazine compound 6%).

$^1$H-NMR spectrum (CDCl$_3$) δppm: 1.40-1.50 (2H, m), 1.63 (4H, quin, J=5.5 Hz), 2.05 (3H, s), 2.73 (4H, t, J=5.5 Hz), 7.09 (1H, s), 7.14 (1H, dd, J=8.2, 0.9 Hz), 7.25-7.37 (3H, m), 7.47 (1H, td, J=8.2, 1.8 Hz), 8.05 (1H, s).
Mass spectrum m/z (FAB): 313 (M$^+$+1)

Example 171

[1-imidazol-1-yl-1-(2-pentyloxyphenyl)methylidene] piperidin-1-ylamine (Compound No. 173)

In the same manner as in Example 3, the object compound was obtained (yellow liquid, yield from acylhydrazine compound 28%).
$^1$H-NMR spectrum (CDCl$_3$) δppm: 0.84 (3H, t, J=5.3 Hz), 1.13-1.69 (12H, m), 2.72 (4H, t, J=5.3 Hz), 3.88 (2H, s), 6.94-7.04 (3H, m), 7.30 (1H, s), 7.37-7.44 (2H, m), 7.58 (1H, s).
Mass spectrum m/z (FAB): 341 (M$^+$+1)

Example 172

[1-[2-(3-fluorobenzyloxy)phenyl]-1-imidazol-1-ylmethylidene]piperidin-1-ylamine (Compound No. 174)

In the same manner as in Example 36, carboxylic acid compound 2-(3-fluorobenzyloxy)benzoic acid was obtained. Then, in the same manner as in Example 3, the object compound was obtained (yellow liquid, yield from acylhydrazine compound 35%).
$^1$H-NMR spectrum (CDCl$_3$) δppm: 1.36 (2H, dd, J=11.0, 5.5 Hz), 1.44-1.49 (4H, m), 2.73 (4H, t, J=5.5 Hz), 5.02 (2H, s), 6.86-7.09 (6H, m), 7.34 (1H, s), 7.39-7.45 (2H, m), 7.62 (1H, s).
Mass spectrum m/z (FAB): 379 (M$^+$+1)

Example 173

[1-imidazol-1-yl-1-[2-(2-phenoxyethoxy)phenyl]methylidene]piperidin-1-ylamine (Compound No. 175)

In the same manner as in Example 3, the object compound was obtained (yellow liquid, yield from acylhydrazine compound 28%).
$^1$H-NMR spectrum (CDCl$_3$) δppm: 1.34 (2H, dd, J=11.0, 5.5 Hz), 1.41-1.47 (4H, m), 2.70 (4H, t, J=5.5 Hz), 4.08 (2H, t, J=5.0 Hz), 4.27 (2H, s), 6.82 (2H, d, J=7.8 Hz), 6.95 (1H, t, J=7.3 Hz), 7.05-7.09 (2H, m), 7.24-7.28 (3H, m), 7.38 (1H, dd, J=7.6, 1.8 Hz), 7.46 (1H, td, J=8.0, 1.8 Hz), 7.60 (1H, s).
Mass spectrum m/z (FAB): 391 (M$^+$+1)

Example 174

[1-(2-chlorophenyl)-1-imidazol-1-ylmethylidene]-(2,6-dimethylpiperidin-1-yl)amine (Compound No. 176)

In the same manner as in Example 1, the object compound was obtained (yellow liquid, yield from acylhydrazine compound 34%).
$^1$H-NMR spectrum (CDCl$_3$) δppm: 1.01 (6H, d, J=6.3 Hz), 1.40-1.80 (6H, m), 2.50-2.70 (2H, m), 6.99 (1H, s), 7.30-7.65 (5H, m), 8.63 (1H, s).
Mass spectrum m/z (FAB): 317 (M$^+$+1)

Example 175

[1-(2-chlorophenyl)-1-imidazol-1-ylmethylidene] homopiperidin-1-ylamine (Compound No. 177)

In the same manner as in Example 1, the object compound was obtained (yellow liquid, yield from acylhydrazine compound 99%).
$^1$H-NMR spectrum (CDCl$_3$) δppm: 1.53 (8H, br s), 3.00-3.20 (4H, m), 7.03 (1H, s), 7.11 (1H, s), 7.25-7.50 (4H, m), 7.54 (1H, s).
Mass spectrum m/z (FAB): 303 (M$^+$+1)

Example 176

[1-(2,4-dichlorophenyl)-1-imidazol-1-ylmethylidene] homopiperidin-1-ylamine (Compound No. 178)

In the same manner as in Example 1, the object compound was obtained (yellow liquid, yield from acylhydrazine compound 7%).
$^1$H-NMR spectrum (CDCl$_3$) δppm: 1.54 (8H, br s), 3.00-3.20 (4H, m), 7.03 (1H, s), 7.07 (1H, s), 7.30-7.45 (2H, m), 7.50 (1H, s), 7.55 (1H, s).
Mass spectrum m/z (FAB): 337 (M$^+$+1)

Example 177

[1-(5-bromo-2-chlorophenyl)-1-imidazol-1-ylmethylidene]homopiperidin-1-ylamine (Compound No. 179)

In the same manner as in Example 1, the object compound was obtained (yellow liquid, yield from acylhydrazine compound 68%).
$^1$H-NMR spectrum (CDCl$_3$) δppm: 1.45-1.70 (8H, m), 3.05-3.20 (4H, m), 7.04 (1H, s), 7.07 (1H, s), 7.35 (1H, d, J=8.7 Hz), 7.51-7.58 (3H, m).
Mass spectrum m/z (FAB): 383 (M$^+$+1)

Example 178

[1-(2-chloro-4-hydroxyphenyl)-1-imidazol-1-ylmethylidene]homopiperidin-1-ylamine (Compound No. 180)

In the same manner as in Example 13, the object compound was obtained (pale-yellow powder, yield from acylhydrazine compound 32%).
$^1$H-NMR spectrum (CDCl$_3$) δppm: 1.45-1.65 (8H, m), 3.08-3.25 (4H, m), 6.81 (1H, d, J=8.2, 2.3 Hz), 6.91 (1H, d, J=2.3 Hz), 7.08 (1H, s), 7.21 (1H, s), 7.23 (2H, s), 7.50 (1H, s).
Mass spectrum m/z (FAB): 319 (M$^+$+1)

Example 179

[1-[2-chloro-4-(4-chlorobenzyloxy)phenyl]-1-imidazol-1-ylmethylidene]homopiperidin-1-ylamine (Compound No. 181)

Using the Compound No. 180 obtained in Example 178 and in the same manner as in Example 64, the object compound was obtained (yellow liquid, yield 78%).
$^1$H-NMR spectrum (CDCl$_3$) δppm: 1.45-1.65 (8H, br s), 3.00-3.20 (4H, br s), 5.07 (2H, s), 6.94 (1H, dd, J=8.7, 2.3

Hz), 7.02 (1H, s), 7.07 (1H, d, J=2.3 Hz), 7.12 (1H, s), 7.34-7.44 (5H, m), 7.55 (1H, s).

Mass spectrum m/z (FAB): 443 (M$^+$+1)

Example 180

[1-[2-chloro-4-(4-chloro-2-trifluoromethylquinolin-6-ylmethoxy)phenyl]-1-imidazol-1-ylmethylidene]homopiperidin-1-ylamine (Compound No. 182)

Using the Compound No. 180 obtained in Example 178 and in the same manner as in Example 64, the object compound was obtained (pale-yellow powder, yield 39%).

$^1$H-NMR spectrum (CDCl$_3$) δppm: 1.45-1.64 (8H, m), 3.02-3.20 (4H, m), 5.37 (2H, s), 7.00-7.05 (2H, m), 7.13 (1H, s), 7.16 (1H, d, J=2.7 Hz), 7.40 (1H, d, J=8.7 Hz), 7.55 (1H, s), 7.88 (1H, s), 7.96 (1H, dd, J=8.7, 1.8 Hz), 8.31 (1H, d, J=9.2 Hz), 8.37 (1H, d, J=0.9 Hz).

Mass spectrum m/z (FAB): 562 (M$^+$+1)

Example 181

[1-(2-bromo-5-methoxyphenyl)-1-imidazol-1-ylmethylidene]homopiperidin-1-ylamine (Compound No. 183)

In the same manner as in Example 1, the object compound was obtained (pale-yellow powder, yield from acylhydrazine compound 66%).

$^1$H-NMR spectrum (CDCl$_3$) δppm: 1.45-1.65 (8H, m), 3.05-3.20 (4H, m), 3.81 (3H, s), 6.88 (1H, dd, J=9.2, 3.2 Hz), 6.95 (1H, d, J=3.2 Hz), 7.03 (1H, s), 7.11 (1H, t, J=1.4 Hz), 7.52 (1H, d, J=9.2 Hz), 7.55 (1H, s).

Mass spectrum m/z (FAB): 377 (M$^+$+1)

Example 182

[1-(2-ethylphenyl)-1-imidazol-1-ylmethylidene]homopiperidin-1-ylamine (Compound No. 184)

In the same manner as in Example 1, the object compound was obtained (yellow liquid, yield from acylhydrazine compound 64%).

$^1$H-NMR spectrum (CDCl$_3$) δppm: 1.13 (3H, t, J=7.8 Hz), 1.50-1.69 (8H, m), 2.55 (2H, q, J=7.8 Hz), 2.97-3.10 (4H, m), 7.02 (1H, s), 7.16 (1H, s), 7.24-7.26 (2H, m), 7.32-7.34 (1H, m), 7.38-7.43 (1H, m), 7.54 (1H, s).

Mass spectrum m/z (FAB): 297 (M$^+$+1)

Example 183

[1-(2-hexylphenyl)-1-imidazol-1-ylmethylidene]homopiperidin-1-ylamine (Compound No. 185)

In the same manner as in Example 1, the object compound was obtained (yellow liquid, yield from acylhydrazine compound 64%).

$^1$H-NMR spectrum (CDCl$_3$) δppm: 0.84 (3H, t, J=6.9 Hz), 1.22-1.30 (6H, m), 1.47-1.69 (8H, m), 2.43-2.61 (2H, m), 2.95-3.11 (4H, m), 7.02 (1H, s), 7.15 (1H, s), 7.23-7.31 (3H, m), 7.36-7.40 (1H, m), 7.54 (1H, s).

Mass spectrum m/z (FAB): 353 (M$^+$+1)

Example 184

[1-(2-benzylphenyl)-1-imidazol-1-ylmethylidene]homopiperidin-1-ylamine (Compound No. 186)

In the same manner as in Example 1, the object compound was obtained (yellow liquid, yield from acylhydrazine compound 66%).

$^1$H-NMR spectrum (CDCl$_3$) δppm: 1.52-1.61 (8H, m), 2.97-3.12 (4H, m), 3.87 (1H, d, J=15.6 Hz), 3.94 (1H, d, J=15.6 Hz), 6.94 (1H, s), 6.99 (1H, s), 7.04-7.05 (2H, m), 7.11-7.28 (6H, m), 7.35-7.39 (2H, m).

Mass spectrum m/z (FAB): 359 (M$^+$+1)

Example 185 homopiperidin-1-yl-[1-imidazol-1-yl-1-(2-phenethylphenyl)methylidene]amine (Compound No. 187)

In the same manner as in Example 1, the object compound was obtained (yellow liquid, yield from acylhydrazine compound 52%).

$^1$H-NMR spectrum (CDCl$_3$) δppm: 1.51-1.63 (8H, m), 2.71-3.11 (8H, m), 7.01 (1H, s), 7.08 (2H, d, J=6.9 Hz), 7.13-7.43 (8H, m), 7.52 (1H, s).

Mass spectrum m/z (FAB): 373 (M$^+$+1)

Example 186 homopiperidin-1-yl-[1-imidazol-1-yl-1-(2-trifluoromethylphenyl)methylidene]amine (Compound No. 188)

In the same manner as in Example 1, the object compound was obtained (yellow liquid, yield from acylhydrazine compound 56%).

$^1$H-NMR spectrum (CDCl$_3$) δppm: 1.40-1.65 (8H, m), 2.95-3.10 (4H, m), 7.01 (1H, s), 7.12 (1H, s), 7.45-7.70 (4H, m), 7.76 (1H, s).

Mass spectrum m/z (FAB): 337 (M$^+$+1)

Example 187 homopiperidin-1-yl-[1-imidazol-1-yl-1-(2-phenoxymethylphenyl)methylidene]amine (Compound No. 189)

In the same manner as in Example 1, the object compound was obtained (pale-yellow powder, yield from acylhydrazine compound 59%).

$^1$H-NMR spectrum (CDCl$_3$) δppm: 1.40-1.60 (8H, m), 2.90-3.00 (2H, m), 3.02-3.12 (2H, m), 4.96 (1H, d, J=12.8 Hz), 5.04 (1H, J=12.8 Hz), 6.82 (2H, d, J=7.8 Hz), 6.93 (1H, t, J=7.8 Hz), 7.04 (1H, s), 7.15 (1H, s), 7.20-7.26 (2H, m), 7.33 (1H, dd, J=7.8, 1.4 Hz), 7.40 (1H, t, J=7.8 Hz), 7.50 (1H, td, J=7.8, 1.4 Hz), 7.60 (1H, s), 7.66 (1H, d, J=7.3 Hz).

Mass spectrum m/z (FAB): 375 (M$^+$+1)

Example 188

[1-(2-benzoyloxymethylphenyl)-1-imidazol-1-ylmethylidene]homopiperidin-1-ylamine (Compound No. 190)

In the same manner as in Example 1, the object compound was obtained (yellow liquid, yield from acylhydrazine compound 48%).

¹H-NMR spectrum (CDCl₃) δppm: 1.40-1.60 (8H, m), 2.90-3.00 (2H, m), 3.04-3.15 (2H, m), 5.30 (1H, d, J=12.8 Hz), 5.40 (1H, J=12.8 Hz), 7.01 (1H, s), 7.18 (1H, s), 7.30-7.60 (7H, m), 7.62 (1H, s), 7.84 (2H, dd, J=8.2, 0.9 Hz).
Mass spectrum m/z (FAB): 403 (M⁺+1)

Example 189 homopiperidin-1-yl-[1-imidazol-1-yl-1-(2-phenylthiomethylphenyl)methylidene]amine (Compound No. 191)

In the same manner as in Example 1, the object compound was obtained (yellow liquid, yield from acylhydrazine compound 67%).
¹H-NMR spectrum (CDCl₃) δppm: 1.40-1.60 (8H, m), 2.88-2.98 (2H, m), 3.05-3.15 (2H, m), 4.04 (1H, d, J=14.2 Hz), 4.20 (1H, d, J=14.2 Hz), 7.02 (1H, s), 7.13 (1H, s), 7.10-7.45 (9H, m), 7.54 (1H, s).
Mass spectrum m/z (FAB): 391 (M⁺+1)

Example 190

[1-(4-carboxyphenyl)-1-imidazol-1-ylmethylidene]homopiperidin-1-ylamine (Compound No. 192)

The Compound No. 193 (0.046 g, 0.141 mmol) obtained in Example 191 was dissolved in methanol (1.5 ml), aqueous solution (0.5 ml) of lithium hydroxide monohydrate (0.009 g, 0.21 mmol) was added, and the mixture was stirred at room temperature for 18 hr. Saturated aqueous ammonium chloride solution was added to the reaction mixture, and the mixture was extracted with ethyl acetate. The extract was dried over sodium sulfate and the mixture was concentrated under reduced pressure. The obtained residue was subjected to silica gel column chromatography to give the object compound (pale-yellow powder, yield 32%).
¹H-NMR spectrum (CDCl₃) δppm: 1.50-1.60 (4H, m), 1.62-1.71 (4H, m), 3.17-3.23 (4H, m), 7.07 (1H, s), 7.24-7.30 (4H, m), 7.72 (1H, s), 7.99 (2H, d, J=8.8 Hz).
Mass spectrum m/z (FAB): 313 (M⁺+1)

Example 191 homopiperidin-1-yl-[1-imidazol-1-yl-1-(4-methoxycarbonylphenyl)methylidene]amine (Compound No. 193)

In the same manner as in Example 1, the object compound was obtained (pale-yellow powder, yield from acylhydrazine compound 13%).
¹H-NMR spectrum (CDCl₃) δppm: 1.50-1.60 (4H, m), 1.60-1.70 (4H, m), 3.19 (4H, t, J=5.5 Hz), 3.90 (3H, s), 7.06 (1H, t, J=1.4 Hz), 7.23 (1H, s), 7.26 (2H, d, J=8.7 Hz), 7.63 (1H, s), 7.93 (2H, d, J=8.7 Hz).
Mass spectrum m/z (FAB): 327 (M⁺+1)

Example 192 homopiperidin-1-yl-[1-(2-hydroxyphenyl)-1-imidazol-1-ylmethylidene]amine (Compound No. 194)

Using the Compound No. 195 obtained in Example 193 and in the same manner as in Example 13, the object compound was obtained (yellow liquid, yield 11%).

¹H-NMR spectrum (CDCl₃) δppm: 1.60-1.76 (8H, m), 3.10-3.16 (4H, m), 6.90 (1H, t, J=6.9 Hz), 7.06-7.12 (3H, m), 7.16 (1H, s), 7.47 (1H, td, J=6.9, 1.8 Hz), 7.80 (1H, s).
Mass spectrum m/z (FAB): 285 (M⁺+1)

Example 193

[1-(2-acetoxyphenyl)-1-imidazol-1-ylmethylidene]homopiperidin-1-ylamine (Compound No. 195)

In the same manner as in Example 1, the object compound was obtained (yellow liquid, yield from acylhydrazine compound 9%).
¹H-NMR spectrum (CDCl₃) δppm: 1.45-1.65 (8H, m), 2.11 (3H, s), 3.00-3.10 (4H, m), 7.02 (1H, s), 7.05 (1H, s), 7.22-7.32 (2H, M) 7.38 (1H, dd, J=7.8, 1.8 Hz), 7.49 (1H, td, J=7.8, 1.8 Hz), 7.66 (1H, s).
Mass spectrum m/z (FAB): 327 (M⁺+1)

Example 194 homopiperidin-1-yl-[1-imidazol-1-yl-1-(2-methoxyphenyl)methylidene]amine (Compound No. 196)

In the same manner as in Example 1, the object compound was obtained (yellow liquid, yield from acylhydrazine compound 56%).
¹H-NMR spectrum (CDCl₃) δppm: 1.40-1.60 (8H, br s), 2.95-3.15 (4H, br s), 3.74 (3H, s), 6.96-7.05 (3H, m), 7.19 (1H, t, J=1.4 Hz), 7.35 (1H, dd, J=7.3, 1.8 Hz), 7.43 (1H, td, J=7.3, 1.8 Hz), 7.54 (1H, s).
Mass spectrum m/z (FAB): 299 (M⁺+1)

Example 195

[1-(2-ethoxyphenyl)-1-imidazol-1-ylmethylidene]homopiperidin-1-ylamine (Compound No. 197)

In the same manner as in Example 1, the object compound was obtained (yellow liquid, yield from acylhydrazine compound 59%).
¹H-NMR spectrum (CDCl₃) δppm: 1.17 (3H, t, J=6.9 Hz), 1.51-1.60 (8H, m), 3.07-3.10 (4H, m), 3.96 (2H, br s), 6.93 (1H, d, J=8.2 Hz), 6.99-7.03 (2H, m), 7.16 (1H, s), 7.36-7.42 (2H, m), 7.55 (1H, s).
Mass spectrum m/z (FAB): 313 (M⁺+1)

Example 196 homopiperidin-1-yl-[1-imidazol-1-yl-1-(2-isopropoxyphenyl)methylidene]amine (Compound No. 198)

In the same manner as in Example 1, the object compound was obtained (yellow liquid, yield from acylhydrazine compound 51%).
¹H-NMR spectrum (CDCl₃) δppm: 1.03-1.25 (4H, m), 1.52-1.64 (4H, m), 1.64 (6H, s), 3.06-3.09 (4H, m), 4.40-4.55 (1H, m), 6.90-6.99 (3H, m), 7.13 (1H, s), 7.36-7.40 (2H, m), 7.55 (1H, s).
Mass spectrum m/z (FAB): 327 (M⁺+1)

Example 197 homopiperidin-1-yl-[1-imidazol-1-yl-1-(2-propoxyphenyl)methylidene]amine (Compound No. 199)

In the same manner as in Example 1, the object compound was obtained (yellow liquid, yield from acylhydrazine compound 62%).

$^1$H-NMR spectrum (CDCl$_3$) δppm: 0.81 (3H, t, J=7.8 Hz), 1.51-1.64 (10H, m), 3.06-3.08 (4H, m), 3.84 (2H, br s), 6.87-7.02 (3H, m), 7.16 (1H, s), 7.36-7.42 (2H, m), 7.54 (1H, s).

Mass spectrum m/z (FAB): 327 (M$^+$+1)

Example 198 homopiperidin-1-yl-[1-imidazol-1-yl-1-[2-(2-propenyloxy)phenyl]methylidene]amine (Compound No. 200)

In the same manner as in Example 36, carboxylic acid compound 2-(2-propenyloxy)benzoic acid was obtained. Then, in the same manner as in Example 1, the object compound was obtained (yellow liquid, yield from acylhydrazine compound 57%).

$^1$H-NMR spectrum (CDCl$_3$) δppm: 1.51-1.66 (8H, m), 3.05-3.10 (4H, m), 4.47 (2H, br s), 5.15-5.22 (2H, m), 5.75-5.84 (1H, m), 6.94-7.05 (3H, m), 7.18 (1H, s), 7.36-7.43 (2H, m), 7.56 (1H, s).

Mass spectrum m/z (FAB): 325 (M$^+$+1)

Example 199 homopiperidin-1-yl-[1-imidazol-1-yl-1-[2-((Z)-propenyloxy)phenyl]methylidene]amine (Compound No. 201)

In the same manner as in Example 36, a carboxylic acid compound 2-((Z)-propenyloxy)benzoic acid was obtained. Then, in the same manner as in Example 1, the object compound was obtained (yellow liquid, yield from acylhydrazine compound 41%).

$^1$H-NMR spectrum (CDCl$_3$) δppm: 1.46-1.63 (11H, m), 3.08-3.10 (4H, m), 4.83-4.90 (1H, m), 6.29-6.31 (1H, m), 7.00-7.13 (3H, m), 7.16 (1H, s), 7.40-7.45 (2H, m), 7.60 (1H, s).

Mass spectrum m/z (FAB): 325 (M$^+$+1)

Example 200

[1-(2-butoxyphenyl)-1-imidazol-1-ylmethylidene]homopiperidin-1-ylamine (Compound No. 202)

In the same manner as in Example 1, the object compound was obtained (yellow liquid, yield from acylhydrazine compound 70%).

$^1$H-NMR spectrum (CDCl$_3$) δppm: 0.85 (3H, t, J=7.3 Hz), 1.22-1.27 (2H, m), 1.49-1.67 (10H, m), 3.05-3.11 (4H, m), 3.88 (2H, br s), 6.92-7.03 (3H, m), 7.15 (1H, s), 7.36-7.42 (2H, m), 7.54 (1H, s).

Mass spectrum m/z (FAB): 341 (M$^+$+1)

Example 201 homopiperidin-1-yl-[1-imidazol-1-yl-1-(2-pentyloxyphenyl)methylidene]amine (Compound No. 203)

In the same manner as in Example 1, the object compound was obtained (yellow liquid, yield from acylhydrazine compound 60%).

$^1$H-NMR spectrum (CDCl$_3$) δppm: 0.85 (3H, t, J=7.3 Hz), 1.10-1.30 (4H, m), 1.40-1.60 (10H, m), 2.95-3.20 (4H, m), 3.75-4.00 (2H, m), 6.93 (1H, d, J=8.2 Hz), 6.95-7.04 (2H, m), 7.16 (1H, s), 7.35-7.44 (2H, m), 7.53 (1H, s).

Mass spectrum m/z (FAB): 355 (M$^+$+1)

Example 202 homopiperidin-1-yl-[1-(2-pentyloxyphenyl)-1-(1,2,4-triazol-1-yl)methylidene]amine (Compound No. 204)

In the same manner as in Example 18, the object compound was obtained (yellow liquid, yield from acylhydrazine compound 18%).

$^1$H-NMR spectrum (CDCl$_3$) δppm: 0.86 (3H, t, J=7.3 Hz), 1.10-1.30 (4H, m), 1.45-1.80 (10H, m), 3.10-3.30 (4H, m), 3.85 (2H, br s), 6.90 (1H, d, J=8.2 Hz), 7.01 (1H, t, J=7.8 Hz), 7.36-7.42 (2H, m), 7.85 (1H, s), 8.45 (1H, s).

Mass spectrum m/z (FAB): 356 (M$^+$+1)

Example 203

[1-(2-hexyloxyphenyl)-1-imidazol-1-ylmethylidene]homopiperidin-1-ylamine (Compound No. 205)

In the same manner as in Example 1, the object compound was obtained (yellow liquid, yield from acylhydrazine compound 61%)

$^1$H-NMR spectrum (CDCl$_3$) δppm: 0.86 (3H, t, J=6.9 Hz), 1.22-1.25 (8H, m), 1.51-1.58 (8H, m), 3.06-3.10 (4H, m), 3.89 (2H, br s), 6.93 (1H, d, J=8.2 Hz), 6.98-7.02 (2H, m), 7.15 (1H, s), 7.36-7.41 (2H, m), 7.53 (1H, s).

Mass spectrum m/z (FAB): 369 (M$^+$+1)

Example 204

[1-(2-heptyloxyphenyl)-1-imidazol-1-ylmethylidene]homopiperidin-1-ylamine (Compound No. 206)

In the same manner as in Example 1, the object compound was obtained (yellow liquid, yield from acylhydrazine compound 71%).

$^1$H-NMR spectrum (CDCl$_3$) δppm: 0.87 (3H, t, J=7.3 Hz), 1.22-1.64 (18H, m), 3.05-3.15 (4H, m), 3.88 (2H, br s), 6.92-7.02 (3H, m), 7.16 (1H, s), 7.36-7.41 (2H, m), 7.53 (1H, s).

Mass spectrum m/z (FAB): 383 (M$^+$+1)

Example 205 homopiperidin-1-yl-[1-imidazol-1-yl-1-(2-octyloxyphenyl)methylidene]amine (Compound No. 207)

In the same manner as in Example 1, the object compound was obtained (yellow liquid, yield from acylhydrazine compound 58%).

$^1$H-NMR spectrum (CDCl$_3$) δppm: 0.88 (3H, t, J=7.3 Hz), 1.22-1.68 (20H, m), 3.06-3.08 (4H, m), 3.87 (2H, br s), 6.92-7.03 (3H, m), 7.16 (1H, s), 7.36-7.42 (2H, m), 7.53 (1H, s).

Mass spectrum m/z (FAB): 397 (M$^+$+1)

Example 206

[1-(5-fluoro-2-pentyloxyphenyl)-1-imidazol-1-ylm-ethylidene]homopiperidin-1-ylamine
(Compound No. 208)

In the same manner as in Example 36, a carboxylic acid compound 5-fluoro-2-pentyloxybenzoic acid was obtained. Then, in the same manner as in Example 1, the object compound was obtained (yellow liquid, yield from acylhydrazine compound 37%).
$^1$H-NMR spectrum (CDCl$_3$) δppm: 0.85 (3H, t, J=7.3 Hz), 1.18-1.27 (4H, m), 1.40-1.62 (10H, m), 3.07-3.10 (4H, m), 3.83 (2H, br s), 6.85-6.89 (1H, m), 6.99 (1H, s), 7.08-7.13 (3H, m), 7.54 (1H, s).
Mass spectrum m/z (FAB): 373 (M$^+$+1)

Example 207 homopiperidin-1-yl-[1-imidazol-1-yl-1-(3-methoxy-2-pentyloxyphenyl)methylidene]amine
(Compound No. 209)

In the same manner as in Example 36, a carboxylic acid compound 3-methoxy-2-pentyloxybenzoic acid was obtained. Then, in the same manner as in Example 1, the object compound was obtained (yellow liquid, yield from acylhydrazine compound 34%).
$^1$H-NMR spectrum (CDCl$_3$) δppm: 0.85 (3H, t, J=7.3 Hz), 1.21-1.54 (14H, m), 3.04-3.10 (4H, m), 3.47-3.50 (1H, m), 3.88 (3H, s), 4.05-4.10 (1H, m), 6.92-7.11 (4H, m), 7.16 (1H, s), 7.58 (1H, s).
Mass spectrum m/z (FAB): 385 (M$^+$+1)

Example 208 homopiperidin-1-yl-[1-imidazol-1-yl-1-(4-methoxy-2-pentyloxyphenyl)methylidene]amine
(Compound No. 210)

In the same manner as in Example 36, a carboxylic acid compound 4-methoxy-2-pentyloxybenzoic acid was obtained. Then, in the same manner as in Example 1, the object compound was obtained (yellow liquid, yield from acylhydrazine compound 29%).
$^1$H-NMR spectrum (CDCl$_3$) δppm: 0.85 (3H, t, J=7.3 Hz), 1.17-1.77 (14H, m), 3.02-3.15 (4H, m), 3.80-3.84 (2H, m), 3.85 (3H, s), 6.46 (1H, d, J=1.8 Hz), 6.53 (1H, dd, J=8.7, 2.3 Hz), 6.98 (1H, s), 7.16 (1H, s), 7.29 (1H, d, J=8.2 Hz), 7.54 (1H, s).
Mass spectrum m/z (FAB): 385 (M$^+$+1)

Example 209 homopiperidin-1-yl-[1-imidazol-1-yl-1-(5-methoxy-2-pentyloxyphenyl)methylidene]amine
(Compound No. 211)

In the same manner as in Example 36, a carboxylic acid compound 5-methoxy-2-pentyloxybenzoic acid was obtained. Then, in the same manner as in Example 1, the object compound was obtained (yellow liquid, yield from acylhydrazine compound 48%).
$^1$H-NMR spectrum (CDCl$_3$) δppm: 0.85 (3H, t, J=6.9 Hz), 1.18-1.54 (14H, m), 3.06-3.11 (4H, m), 3.78 (3H, s), 3.77-3.85 (2H, m), 6.86 (1H, d, J=8.7 Hz), 6.92-6.98 (3H, m), 7.16 (1H, s), 7.54% (1H, s).
Mass spectrum m/z (FAB): 385 (M$^+$+1)

Example 210 homopiperidin-1-yl-[1-imidazol-1-yl-1-(2-phenoxyphenyl)methylidene]amine (Compound No. 212)

In the same manner as in Example 1, the object compound was obtained (yellow liquid, yield from acylhydrazine compound 69%).
$^1$H-NMR spectrum (CDCl$_3$) δppm: 1.53-1.67 (8H, m), 3.11-3.14 (4H, M), 6.85-6.91 (3H, m), 7.00 (1H, s), 7.10-7.16 (2H, m), 7.21 (1H, s), 7.23-7.39 (3H, m), 7.45 (1H, dd, J=7.8, 1.4 Hz), 7.63 (1H, s).
Mass spectrum m/z (FAB): 361 (M$^+$+1)

Example 211

[1-(2-benzyloxyphenyl)-1-imidazol-1-ylmeth-ylidene]homopiperidin-1-ylamine
(Compound No. 213)

In the same manner as in Example 1, the object compound was obtained (yellow liquid, yield from acylhydrazine compound 67%).
$^1$H-NMR spectrum (CDCl$_3$) δppm: 1.46-1.60 (8H, m), 3.02-3.11 (4H, m), 5.02 (2H, br s), 7.00-7.17 (5H, m), 7.25-7.32 (2H, m), 7.38-7.49 (4H, m), 7.59 (1H, s).
Mass spectrum m/z (FAB): 375 (M$^+$+1)

Example 212

[1-[2-(4-chlorobenzyloxy)phenyl]-1-imidazol-1-ylmethylidene]homopiperidin-1-ylamine
(Compound No. 214)

In the same manner as in Example 1, the object compound was obtained (yellow liquid, yield from acylhydrazine compound 73%).
$^1$H-NMR spectrum (CDCl$_3$) δppm: 1.47-1.61 (8H, m), 3.05-3.11 (4H, m), 4.96-4.97 (2H, m), 6.98-7.08 (5H, m), 7.17 (1H, s), 7.26-7.29 (2H, m), 7.40 (2H, d, J=7.8 Hz), 7.57 (1H, s).
Mass spectrum m/z (FAB): 409 (M$^+$+1)

Example 213 homopiperidin-1-yl-[1-imidazol-1-yl-1-[2-(2-phenoxyethoxy)phenyl]methylidene]amine
(Compound No. 215)

In the same manner as in Example 1, the object compound was obtained (yellow liquid, yield from acylhydrazine compound 41%).
$^1$H-NMR spectrum (CDCl$_3$) δppm: 1.47-1.61 (8H, m), 3.04-3.07 (4H, m), 4.07 (2H, t, J=5.0 Hz), 4.27 (2H, br s), 6.83 (2H, d, J=7.8 Hz), 6.95-7.07 (4H, m), 7.13 (1H, s), 7.24-7.28 (2H, m), 7.37-7.45 (2H, m), 7.55 (1H, s).
Mass spectrum m/z (FAB): 405 (M$^+$+1)

Example 214 homopiperidin-1-yl-[1-imidazol-1-yl-1-[2-(3-phenoxypropoxy)phenyl]methylidene]amine (Compound No. 216)

In the same manner as in Example 36, a carboxylic acid compound 2-(3-phenoxypropoxy)benzoic acid was obtained.

Then, in the same manner as in Example 1, the object compound was obtained (yellow liquid, yield from acylhydrazine compound 48%).

$^1$H-NMR spectrum (CDCl$_3$) δppm: 1.42-1.70 (8H, m), 2.02-2.07 (2H, m), 2.98-3.09 (4H, m), 3.82-3.87 (2H, m), 4.03-4.18 (2H, m), 6.84 (2H, d, J=7.8 Hz), 6.91-7.04 (4H, m), 7.11 (1H, s), 7.25-7.29 (2H, m), 7.37-7.43 (2H, m), 7.57 (1H, s).

Mass spectrum m/z (FAB): 419 (M$^+$+1)

Example 215 homopiperidin-1-yl-[1-imidazol-1-yl-1-[2-(4-phenoxybutoxy)phenyl]methylidene]amine
(Compound No. 217)

In the same manner as in Example 36, a carboxylic acid compound 2-(4-phenoxybutoxy)benzoic acid was obtained. Then, in the same manner as in Example 1, the object compound was obtained (yellow liquid, yield from acylhydrazine compound 31%).

$^1$H-NMR spectrum (CDCl$_3$) δppm: 1.51-1.78 (12H, m), 3.06-3.09 (4H, m), 3.87-3.90 (4H, m), 6.85-7.04 (6H, m), 7.15 (1H, s), 7.26-7.29 (2H, m), 7.38-7.43 (2H, m), 7.54 (1H, s).

Mass spectrum m/z (FAB): 433 (M$^+$+1)

Example 216 homopiperidin-1-yl-[1-imidazol-1-yl-1-[2-(pyridin-2-yloxy)phenyl]methylidene]amine
(Compound No. 218)

In the same manner as in Example 36, a carboxylic acid compound 2-(pyridin-2-yloxy)benzoic acid was obtained. Then, in the same manner as in Example 1, the object compound was obtained (yellow liquid, yield from acylhydrazine compound 49%).

$^1$H-NMR spectrum (CDCl$_3$) δppm: 1.48-1.62 (8H, m), 3.08-3.10 (4H, m), 5.14 (2H, s), 7.00-7.09 (4H, m), 7.16-7.20 (2H, m), 7.42 (2H, d, J=7.8 Hz), 7.63-7.64 (2H, m), 8.52 (1H, d, J=4.6 Hz).

Mass spectrum m/z (FAB): 376 (M$^+$+1)

Example 217 homopiperidin-1-yl-[1-imidazol-1-yl-1-(2-trifluoromethoxyphenyl)methylidene]amine
(Compound No. 219)

In the same manner as in Example 1, the object compound was obtained (yellow liquid, yield from acylhydrazine compound 41%).

$^1$H-NMR spectrum (CDCl$_3$) δppm: 1.51-1.66 (8H, m), 3.04-3.07 (4H, m), 7.03 (1H, s), 7.09-7.12 (1H, m), 7.35-7.44 (3H, m), 7.50-7.54 (1H, m), 7.58 (1H, s).

Mass spectrum m/z (FAB): 353 (M$^+$+1)

Example 218

[1-(2-ethylthiophenyl)-1-imidazol-1-ylmethylidene]homopiperidin-1-ylamine (Compound No. 220)

In the same manner as in Example 1, the object compound was obtained (yellow liquid, yield from acylhydrazine compound 69%).

$^1$H-NMR spectrum (CDCl$_3$) δppm: 1.23 (3H, t, J=7.3 Hz), 1.52-1.62 (8H, m), 2.83-2.97 (2H, m), 3.08-3.10 (4H, m), 7.02 (1H, s), 7.14 (1H, s), 7.20-7.26 (1H, m), 7.33-7.42 (3H, m), 7.50 (1H, s).

Mass spectrum m/z (FAB): 329 (M$^+$+1)

Example 219

[1-(2-dimethylaminophenyl)-1-imidazol-1-ylmethylidene]homopiperidin-1-ylamine
(Compound No. 221)

In the same manner as in Example 1, the object compound was obtained (yellow liquid, yield from acylhydrazine compound 71%).

$^1$H-NMR spectrum (CDCl$_3$) δppm: 1.50-1.67 (8H, m), 2.77 (6H, s), 3.02-3.12 (4H, m), 6.81-6.85 (1H, m), 6.91 (1H, d, J=8.2 Hz), 7.01 (1H, br s), 7.19-7.33 (3H, m), 7.67 (1H, s).

Mass spectrum m/z (FAB): 312 (M$^+$+1)

Example 220 homopiperidin-1-yl-[1-imidazol-1-yl-1-[2-(N-methyl-N-pentylamino)phenyl]methylidene]amine
(Compound No. 222)

In the same manner as in Example 87, the object compound was obtained (yellow liquid, yield from acylhydrazine compound 50%).

$^1$H-NMR spectrum (CDCl$_3$) δppm: 0.85 (3H, t, J=7.3 Hz), 1.09-1.46 (12H, m), 1.63-1.82 (2H, m), 2.69 (6H, s), 2.96-3.12 (6H, m), 6.83-6.87 (1H, m), 6.93 (1H, d, J=8.2 Hz), 7.01 (1H, s), 7.21-7.33 (3H, m), 7.65 (1H, s).

Mass spectrum m/z (FAB): 368 (M$^+$+1)

Example 221 homopiperidin-1-yl-[1-imidazol-1-yl-1-(3-methylsulfanylpyridin-2-yl)methylidene]amine
(Compound No. 223)

In the same manner as in Example 1, the object compound was obtained (pale-yellow powder, yield from acylhydrazine compound 68%).

$^1$H-NMR spectrum (CDCl$_3$) δppm: 1.40-1.70 (8H, m), 2.53 (3H, s), 3.10-3.20 (4H, m), 7.03 (1H, s), 7.06-7.11 (2H, m), 7.52 (1H, s), 7.56 (1H, dd, J=7.6, 1.7 Hz), 8.53 (1H, dd, J=4.6, 1.7 Hz).

Mass spectrum m/z (FAB): 316 (M$^+$+1)

Example 222

[1-(2,5-dichlorothiophen-3-yl)-1-imidazol-1-ylmethylidene]homopiperidin-1-ylamine
(Compound No. 224)

In the same manner as in Example 1, the object compound was obtained (yellow liquid, yield from acylhydrazine compound 24%).

$^1$H-NMR spectrum (CDCl$_3$) δppm: 1.50-1.70 (8H, m), 3.15-3.30 (4H, m), 6.86 (1H, s), 7.11 (1H, s), 7.15 (1H, s), 7.64 (1H, s).

Mass spectrum m/z (FAB): 343 (M$^+$+1)

Example 223

[1-(1-hexylpyrrol-2-yl)-1-imidazol-1-ylmethylidene]homopiperidin-1-ylamine (Compound No. 225)

In the same manner as in Example 103, the object compound was obtained as a mixture of geometric isomers (yellow liquid, yield from acylhydrazine compound 32%).
$^1$H-NMR spectrum (CDCl$_3$) δppm: 0.82-0.90 (3H, m), 1.15-1.31 (6H, m), 1.53-1.61 (10H, m), 2.94, 3.04 (4H, t each, J=5.5 Hz), 3.81, 4.21 (2H, t each, J=7.3 Hz), 5.81-6.28 (2H, m), 6.73-6.89 (1H, m), 7.03-7.24 (2H, m), 7.57, 7.72 (1H, s each).
Mass spectrum m/z (FAB): 341 (M$^+$+1)

Example 224 homopiperidin-1-yl-[1-imidazol-1-yl-1-(2-methylfuran-3-yl)methylidene]amine (Compound No. 226)

In the same manner as in Example 1, the object compound was obtained (yellow liquid, yield from acylhydrazine compound 28%).
$^1$H-NMR spectrum (CDCl$_3$) δppm: 1.50-1.70 (8H, m), 2.20 (3H, s), 3.09-3.14 (4H, m), 6.41 (1H, d, J=2.0 Hz), 7.05 (1H, s), 7.21 (1H, s), 7.36 (1H, d, J=2.0 Hz), 7.72 (1H, s).
Mass spectrum m/z (FAB): 273 (M$^+$+1)

Example 225 homopiperidin-1-yl-[1-imidazol-1-yl-1-(3-methylbenzofuran-2-yl)methylidene]amine (Compound No. 227)

In the same manner as in Example 1, the object compound was obtained (pale-yellow powder, yield from acylhydrazine compound 10%).
$^1$H-NMR spectrum (CDCl$_3$) δppm: 1.57 (4H, br s), 1.68 (4H, br s), 2.09 (3H, s), 3.18 (4H, t, J=6.0 Hz), 7.15 (1H, s), 7.20 (1H, s), 7.20-7.30 (2H, m), 7.36 (1H, d, J=7.8 Hz), 7.47 (1H, d, J=7.8 Hz), 7.71 (1H, s).
Mass spectrum m/z (FAB): 323 (M$^+$+1)

Example 226

[1-(2-chlorophenyl)-1-imidazol-1-ylmethylidene]morpholin-4-ylamine (Compound No. 228)

In the same manner as in Example 1, the object compound was obtained as a mixture of geometric isomers (pale-yellow powder, yield from acylhydrazine compound 34%).
$^1$H-NMR spectrum (CDCl$_3$) δppm: 2.79, 2.90 (4H, t each, J=4.6 Hz), 3.60, 3.81 (4H, t each, J=4.6 Hz), 7.09, 7.10 (1H, s each), 7.27-7.55 (5H, m), 7.60, 8.02 (1H, s each).
Mass spectrum m/z (FAB): 291 (M$^+$+1)

Example 227

[1-imidazol-1-yl-1-(2-trifluoromethylphenyl)methylidene]morpholin-4-ylamine (Compound No. 229)

In the same manner as in Example 1, the object compound was obtained (pale-yellow powder, yield from acylhydrazine compound 10%).
$^1$H-NMR spectrum (CDCl$_3$) δppm: 2.09-2.79 (4H, m), 3.48-3.61 (4H, m), 7.08 (1H, s), 7.31-7.85 (6H, m).
Mass spectrum m/z (FAB): 325 (M$^+$+1)

Example 228

[1-imidazol-1-yl-1-[2-(2-phenoxyethoxy)phenyl]methylidene]morpholin-4-ylamine (Compound No. 230)

To a solution of methyl salicylate (1.377 g, 9.05 mmol) in N,N-dimethylformamide (14 ml) were added β-bromophenetole (1.876 g, 9.33 mmol) and potassium carbonate (1.509 g, 10.91 mmol), and the mixture was stirred at 80° C. for 1.5 hr. Water was added to the reaction mixture, and the precipitated crystals were collected by filtration and washed with water and hexane to give methyl 2-(2-phenoxyethoxy)benzoate (1.545 g, 5.67 mmol, yield 63%). This was dissolved in methanol (10 ml), 2N-aqueous sodium hydroxide solution (10 ml) was added at room temperature, and the mixture was stirred at 60° C. for 3.5 hr. The reaction mixture was concentrated under reduced pressure and neutralized with 2N-aqueous hydrochloric acid solution, and the mixture was extracted with ethyl acetate. The extract was dried over sodium sulfate, and the solvent was evaporated under reduced pressure to give a carboxylic acid compound 2-(2-phenoxyethoxy)benzoic acid (1.407 g, 5.45 mmol, yield 96%).

Using the obtained carboxylic acid compound and in the same manner as in Example 3, the object compound was obtained (yellow liquid, yield from acylhydrazine compound 58%).
$^1$H-NMR spectrum (CDCl$_3$) δppm: 2.75 (4H, t, J=4.6 Hz), 3.56 (4H, t, J=4.6 Hz), 4.09 (2H, t, J=4.6 Hz), 4.28 (2H, br s), 6.80 (2H, d, J=8.2 Hz), 6.95 (1H, t, J=7.3 Hz), 7.01 (1H, s), 7.06-7.11 (2H, m), 7.25-7.30 (3H, m), 7.37 (1H, dd, J=7.3, 1.4 Hz), 7.46-7.51 (1H, m), 7.59 (1H, s).
Mass spectrum m/z (FAB): 393 (M$^+$+1)

Example 229

[1-imidazol-1-yl-1-(2-trifluoromethylphenyl)methylidene]-(4-methylpiperazin-1-yl)amine (Compound No. 231)

In the same manner as in Example 136, the object compound was obtained (pale-yellow powder, yield from acylhydrazine compound 91%).
$^1$H-NMR spectrum (CDCl$_3$) δppm: 2.19 (3H, s), 2.20-2.40 (4H, m), 2.65-2.85 (4H, m), 7.06 (1H, s), 7.29 (1H, s), 7.30-7.45 (1H, m), 7.54 (1H, s), 7.60-7.70 (2H, m), 7.75-7.85 (1H, m).
Mass spectrum m/z (FAB): 338 (M$^+$+1)

Example 230

[1-[2-(4-chlorobenzyloxy)phenyl]-1-imidazol-1-ylmethylidene]-(4-methylpiperazin-1-yl)amine (Compound No. 232)

In the same manner as in Example 136, the object compound was obtained (yellow liquid, yield from acylhydrazine compound 46%).
$^1$H-NMR spectrum (CDCl$_3$) δppm: 2.29 (3H, s), 2.51 (4H, s), 2.85 (4H, t, J=5.0 Hz), 4.86 (2H, s), 6.91-7.08 (6H, m), 7.28-7.50 (4H, m), 7.95 (1H, s).
Mass spectrum m/z (FAB): 410 (M$^+$+1)

Example 231

[1-imidazol-1-yl-1-[2-(2-phenoxyethoxy)phenyl]
methylidene]-(4-methylpiperazin-1-yl)amine
(Compound No. 233)

In the same manner as in Example 228, the object compound was obtained (pale-yellow powder, yield from acylhydrazine compound 34%).

$^1$H-NMR spectrum (CDCl$_3$) δppm: 2.19 (3H, s), 2.30-2.33 (4H, m), 2.81 (4H, t, J=5.0 Hz), 4.08 (2H, t, J=5.0 Hz), 4.28 (2H, br s), 6.81 (2H, d, J=7.8 Hz), 6.93-7.00 (3H, m), 7.06-7.11 (2H, m), 7.24-7.29 (2H, m), 7.36-7.38 (1H, m), 7.44-7.50 (1H, m), 7.58 (1H, s).

Mass spectrum m/z (FAB): 406 (M$^+$+1)

Example 232

[1-[2-(4-chlorobenzyloxy)phenyl]-1-imidazol-1-ylmethylidene]-(4-cyclopentylpiperazin-1-yl)amine
(Compound No. 234)

In the same manner as in Example 136, the object compound was obtained (yellow liquid, yield from acylhydrazine compound 43%).

$^1$H-NMR spectrum (CDCl$_3$) δppm: 1.25-1.81 (8H, m), 2.32-2.40 (5H, m), 2.82 (4H, t, J=4.8 Hz), 4.99 (2H, s), 6.99-7.08 (5H, m), 7.28-7.49 (5H, m), 7.60 (1H, s).

Mass spectrum m/z (FAB): 464 (M$^+$+1)

Formulation Example 1

Dose in Ointment (1 g)

| | | |
|---|---|---|
| (1) | compound No. 1 | 10 mg |
| (2) | white petrolatum | 990 mg |

(1) and (2) are heat-blended (75° C.) in a water bath, and the mixture is stirred with cooling to solidness.

Formulation Example 2

Dose in Cream (1 g)

| | | |
|---|---|---|
| (1) | compound No. 1 | 10 mg |
| (2) | white petrolatum | 250 mg |
| (3) | stearyl alcohol | 200 mg |
| (4) | propylene glycol | 120 mg |
| (5) | polyoxyethylene hydrogenated castor oil 60 | 40 mg |
| (6) | glycerol monostearate | 10 mg |
| (7) | methyl parahydroxybenzoate | 1 mg |
| (8) | p-hydroxybenzoic acid | 1 mg |
| (9) | purified water | e.q. |

(1), (2) and (3) are heat-blended (75° C.) in a water bath, a solution obtained by dissolving (4) to (8) in purified water and heating same to 75° C. is added and the mixture is stirred with cooling to solidness.

Formulation Example 3

Dose in Tablet

| | | |
|---|---|---|
| (1) | compound No. 1 | 100 mg |
| (2) | lactose | 353 mg |
| (3) | calcium carboxymethylcellulose | 30 mg |
| (4) | hydroxymethylcellulose | 7 mg |
| (5) | magnesium stearate | 5 mg |
| (6) | crystalline cellulose | 5 mg |

(1) to (4) and (6) are uniformly mixed. The mixture is granulated and sieved. (5) is added and the mixture is stirred to a certain extent. The mixture is tableted.

Formulation Example 4

Dose in Liquid (1 ml)

| | | |
|---|---|---|
| (1) | compound No. 1 | 10 mg |
| (2) | ethanol | 500 µg |
| (3) | glycerol | 200 µg |
| (4) | propylene glycol | 200 µg |
| (5) | purified water | e.q. |

(1) and (2) are dissolved by stirring, and a solution obtained by dissolving (3) and (4) in purified water is added.

Experimental Example 1

Antifungal Activity Evaluation Test

The minimum inhibitory concentration (MIC) for *Trichophyton mentagrophytes, Trichophyton rubrum*, and *Malassezia furfur* was measured according to the following procedure.

Test compound solution: A test compound was dissolved in dimethyl sulfoxide (DMSO) at a concentration of 5 mg/mL as a stock solution. Diluting this solution with DMSO, a 2-fold dilution series was prepared.

Preparation of MU medium: Peptone (1 g/L), glucose (1 g/L), sodium chloride (5 g/L), potassium dihydrogen phosphate (2 g/L), urea (20 g/L), phenol red (0.012 g/L), Tween 40 (5 mL/L) and Tween 80 (1 mL/L) were dissolved in distilled water, and the solution was sterilized by filtration through a membrane filter.

Test strain: *Trichophyton mentagrophytes* KD-04, *Trichophyton mentagrophytes* SM-110, *Trichophyton rubrum* KD-101, *Trichophyton rubrum* KD-107, and *Malassezia furfur* IFO-0656 were used.

Preparation of fungal inoculum: The above-mentioned 5 test strains were suspended in 0.05% Tween 80-containing physiological saline, and adjusted to a fungus concentration of 2×10$^6$ cells/mL using a counting chamber. Then, as a test medium, a fungal solution of *Trichophyton* species was 100-fold diluted with Sabouraud Dextrose Broth (Difco), and a fungal solution of *Malassezia furfur* IFO-0656 was 100-fold diluted with MU medium to give each inoculum (2×10$^4$ cells/mL).

Measurement of MIC of *Trichophyton* fungi: Sabouraud Dextrose Broth (Difco) was dispensed by 100 µL to a given well of a 96 well flat microplate. Then, a test compound solution (2 µL) was added, and the mixture was thoroughly mixed with a plate mixer. A fungal solution (100 µL) was inoculated and cultured at 30° C. for 7 days. The presence or absence of the cell growth was visually observed, and the minimum medicament concentration at which the cell growth was prevented was taken as MIC (µg/mL).

Measurement of MIC of *Malassezia furfur*: Since the urease activity of this fungus and the fungus growth rate are co-related, MIC was evaluated by the following method using urease activity as an index. MU medium was dispensed by 100 µL to a given well of a 96 well flat microplate. Then, a test compound solution (2 µL) was added, and the mixture was thoroughly mixed with a plate mixer. A fungal solution (100 μL) was inoculated and cultured at 30° C. The culture was stopped on day 4 or 5 of culture when the color tone of the MU medium changes from yellow to red in visual observation of the fungus growth in a well free of addition of a test substance. Then the plate was stirred until the fungus became uniform, and the urease activity was measured based on the measurement of absorbance at 550 nm using a plate reader. With the urease activity of the well free of addition of a test substance as 100%, the minimum medicament concentration of a well that showed urease activity of 20% or below was taken as MIC (μg/mL).

The results are shown in Table 3.

The abbreviations in Table 3 mean the following fungi and compounds.

T. men.: *Trichophyton mentagrophytes*
T. rub.: *Trichophyton rubrum*
M. fur.: *Malassezia furfur*
AMF: amorolfine
ITCZ: itraconazole

TABLE 3

| | MIC (μg/mL) | | | | |
|---|---|---|---|---|---|
| Compound No. | T. men. KD-04 | T. men. SM-110 | T. rub. KD-101 | T. rub. KD-107 | M. fur. IFO-0656 |
| 4 | 0.39 | 0.78 | 0.78 | 0.78 | >25 |
| 6 | 0.05 | 0.10 | 0.10 | 0.05 | 0.78 |
| 9 | 0.05 | 0.20 | 0.05 | 0.05 | 0.2 |
| 16 | 0.20 | 0.39 | 0.20 | 0.20 | 12.5 |
| 17 | 0.20 | 0.39 | 0.20 | 0.20 | 3.13 |
| 19 | 0.20 | 0.20 | 0.78 | 0.20 | 25 |
| 20 | 0.20 | 0.39 | 0.10 | 0.10 | 12.5 |
| 21 | 0.20 | 0.39 | 0.20 | 0.20 | 6.25 |
| 22 | 1.56 | 1.56 | 1.56 | 0.39 | 12.5 |
| 23 | 0.10 | 0.20 | 0.10 | 0.10 | 0.39 |
| 25 | 0.05 | 0.10 | 0.05 | 0.05 | 0.39 |
| 32 | 0.20 | 0.78 | 0.39 | 0.39 | 6.25 |
| 33 | 0.78 | 1.56 | 0.78 | 0.39 | 6.25 |
| 34 | 0.20 | 0.20 | 0.20 | 0.10 | 0.62 |
| 52 | 0.20 | 0.39 | 0.05 | 0.05 | 0.39 |
| 53 | 0.20 | 0.39 | 0.20 | 0.10 | 0.78 |
| 60 | 0.20 | 0.39 | 0.20 | 0.10 | 0.2 |
| 61 | 0.05 | 0.10 | 0.05 | 0.025 | 0.2 |
| 66 | 0.10 | 0.20 | 0.10 | 0.05 | 0.39 |
| 69 | 0.20 | 0.39 | 0.05 | 0.05 | 1.56 |
| 71 | 0.05 | 0.10 | 0.05 | 0.025 | 0.05 |
| 79 | 0.39 | 0.39 | 0.39 | 0.39 | >25 |
| 80 | 0.20 | 0.78 | 0.39 | 0.39 | 12.5 |
| 81 | 0.20 | 0.39 | 0.39 | 0.20 | 3.13 |
| 82 | 0.05 | 0.20 | 0.10 | 0.05 | 0.78 |
| 85 | 0.10 | 0.20 | 0.10 | 0.05 | 0.05 |
| 87 | 0.05 | 0.10 | 0.05 | 0.05 | 0.78 |
| 93 | 0.20 | 0.39 | 0.10 | 0.10 | 6.25 |
| 95 | 1.56 | 3.13 | 1.56 | 0.78 | >25 |
| 101 | 0.05 | 0.20 | 0.05 | 0.05 | 0.2 |
| 104 | 0.025 | 0.05 | 0.025 | 0.025 | >25 |
| 105 | 0.20 | 0.39 | 0.20 | 0.20 | 25 |
| 114 | 0.20 | 0.39 | 0.10 | 0.05 | 0.2 |
| 118 | 0.10 | 0.20 | 0.10 | 0.05 | 0.39 |
| 141 | 0.20 | 0.39 | 0.39 | 0.20 | >10 |
| 157 | 0.05 | 0.10 | 0.05 | 0.05 | 0.2 |
| 158 | 0.20 | 0.20 | 0.20 | 0.10 | 1.56 |
| 161 | 0.20 | 0.39 | 0.10 | 0.10 | 0.39 |
| 173 | 0.20 | 0.20 | 0.10 | 0.10 | 0.39 |
| 184 | 0.05 | 0.10 | 0.05 | 0.05 | 1.56 |
| 198 | 0.10 | 0.20 | 0.20 | 0.10 | 0.78 |
| 200 | 0.10 | 0.10 | 0.10 | 0.10 | 0.2 |
| 211 | 0.20 | 0.39 | 0.20 | 0.10 | 1.56 |
| 212 | 0.39 | 0.78 | 0.78 | 0.39 | 25 |
| 218 | 1.56 | 3.13 | 1.56 | 0.78 | 6.25 |
| AMF | 0.10 | 0.05 | 0.025 | 0.025 | 0.05 |
| ITCZ | 0.10 | 0.20 | 0.10 | 0.05 | 0.05 |

As is clear from Table 3, the compound of the present invention shows a growth inhibitory action on *Trichophyton mentagophytes* and *Trichophyton rubrum*, which are pathogenic fungi of superficial mycosis, at a concentration of 3.13 μg/mL or below, and the compounds include a compound that showed an activity comparable to that of amorolfine or itraconazole, which are commercially available antifungal agents. Moreover, many of these compounds also show a strong growth inhibitory action on *Malassezia furfur*, and include a compound that showed an activity comparable to that of amorolfine or itraconazole, which are commercially available antifungal agents.

Experimental Example 2

Influence of Keratin Addition on Anti-*Trichophyton* Activity

The MIC increase rate by the addition of keratin to a medium was measured by the following procedure.

Test compound solution: A test compound was dissolved in dimethyl sulfoxide (DMSO) at a concentration of 5 mg/mL as a stock solution. Diluting this solution with DMSO, a 2-fold dilution series was prepared.

Test strain: *Trichophyton mentagrophytes* KD-04 was used.

Preparation of Fungal Inoculum: the Above-Mentioned Strain was suspended in 0.05% Tween 80-containing physiological saline, and adjusted to a fungus concentration of $2 \times 10^6$ cells/mL using a counting chamber. Then, as a test medium, the suspension was 100-fold diluted with Sabouraud Dextrose Broth (Difco) to give inoculum ($2 \times 10^4$ cells/mL).

Measurement of MIC increase rate by keratin addition: Keratin (manufactured by MP Biomedicals) (50 mg) was measured in a sterilized test tube, physiological saline (3 mL) was added, and the mixture was sterilized by autoclave at 121° C. for 15 min. The physiological saline was removed, and the mixture was further washed once with physiological saline (3 mL). The physiological saline was removed, and a test compound solution (10 μL) and Sabouraud Dextrose Broth (Difco) (500 μL) were added to keratin, and the mixture was sufficiently stirred. Then, inoculum (500 μL) of *T. mentagrophytes* KD-04 was added, and the mixture was cultured at 30° C. for 7 days. As a comparison control, an experiment similar to the above was performed under conditions free of keratin addition. The growth of the fungus was visually observed, and the minimum medicament concentration at which the cell growth was completely prevented was taken as MIC (μg/mL).

The results are shown in Table 4.

The abbreviations in Table 4 mean the following compounds and medium.

AMF: amorolfine
ITCZ: itraconazole
SDB: Sabouraud dextrose broth

TABLE 4

| | MIC (μg/mL) | | |
|---|---|---|---|
| Compound No. | SDB alone | SDB + keratin | MIC increase rate |
| 4 | 0.39 | 0.78 | 2 |
| 16 | 0.39 | 0.39 | 1 |
| 17 | 0.05 | 0.10 | 2 |
| 20 | 0.10 | 0.20 | 2 |
| 21 | 0.20 | 0.20 | 1 |

TABLE 4-continued

| Compound No. | MIC (µg/mL) SDB alone | MIC (µg/mL) SDB + keratin | MIC increase rate |
|---|---|---|---|
| 22 | 1.56 | 3.13 | 2 |
| 23 | 0.10 | 0.20 | 2 |
| 32 | 0.10 | 0.20 | 2 |
| 33 | 0.39 | 0.39 | 1 |
| 52 | 0.10 | 0.20 | 2 |
| 60 | 0.10 | 0.20 | 2 |
| 66 | 0.05 | 0.10 | 2 |
| 69 | 0.20 | 0.39 | 2 |
| 80 | 0.78 | 0.78 | 1 |
| 81 | 0.39 | 0.39 | 1 |
| 82 | 0.10 | 0.20 | 2 |
| 105 | 0.39 | 0.78 | 2 |
| AMF | 0.05 | 0.39 | 8 |
| ITCZ | 0.05 | 25 | 512 |

As is clear from Table 4, MIC of amorolfine and itraconazole, which are commercially available antifungal agents, for *Trichophyton* increased 8-fold and 512-fold, respectively, by the addition of keratin to medium, and the activity of these commercially available drugs decreased strikingly. In contrast, the MIC of 17 compounds of the present invention increased 1- or 2-fold by the addition of keratin to medium. Thus, it was confirmed that the anti-*Trichophyton* activity of these compounds is not easily influenced by the addition of keratin to medium as compared to commercially available antifungal agents.

Therefrom it is presumed that the compound of the present invention will maintain high activity in the keratinous tissues such as stratum corneum layer, nail and the like, where *Trichophyton* lives, and exhibit a superior effectiveness for tinea pedis and tinea unguium.

Experimental Example 2

Anti-inflammatory Activity Evaluation Test

The test compound was adjusted to 1 w/v % when in use with a solvent (acetone:olive oil=1:1, v/v)) and put to use. FK506 (control substance) was adjusted to 0.1 w/v % and used.

2,4,6-Trinitrochlorobenzene (TNCB)—induced Dermatitis Model

The fur on the abdomen of male BALB/c mouse was shaved with a hair clipper, and 100 µL of 7 w/v % TNCB sensitizing liquid (solvent was acetone:olive oil=4:1, v/v) was applied. Six days after the sensitization, the thickness of the right auricle was measured with a micrometer (pre-value). After the measurement, 10 µL of 1 w/v % TNCB challenge liquid (solvent was acetone:olive oil=1:9, v/v) was applied to the inside of the right auricle to induce ear edema. About 5 minutes after the application of the challenge liquid, 20 µL of the test compound was applied to the outside of the auricle.

After 24 hours from the induction of ear edema, the thickness of the right auricle was measured by a method similar to the pre-value (post-value). The difference between the post-value and the pre-value of ear edema by each test compound was determined, based on which the inhibition rate was calculated. The activity of each test compound was calculated with the ear edema inhibition rate of FK506 as 1.0 (ear edema inhibition rate of each test compound/ear edema inhibition rate of FK506).

Ovalbumin (OVA)—induced Dermatitis Model

Male ICR mouse was sensitized by the administration of 0.2 mL of OVA-hydroxide aluminum gel suspension to the abdominal cavity. After 14 days from the sensitization, the thickness of the right auricle was measured with a micrometer (pre-value). After the measurement, 20 µL of 0.5 µg/mL OVA challenge liquid (solvent was physiological saline) was subcutaneously administered to the inside of the auricle to induce ear edema. About 5 minutes after the administration of the challenge liquid, 20 µL of the test compound was applied to the outside of the auricle. After 24 hours from the induction of ear edema, the thickness of the right auricle was measured by a method similar to the pre-value (post-value). The difference between the post-value and the pre-value of ear edema by each test compound was determined, based on which the inhibition rate was calculated. The activity of each test compound was calculated with the ear edema inhibition rate of FK506 as 1.0 (ear edema inhibition rate of each test compound/ear edema inhibition rate of FK506).

The results are shown in Tables 5-1 and 5-2.

TABLE 5-1

| Compound No. | with ear edema inhibition rate of FK506 as 1.0 | |
|---|---|---|
| | TNCB-induced dermatitis | OVA-induced dermatitis |
| 5 | 0.6 | 1.2 |
| 6 | 0.7 | 1.4 |
| 9 | 0.7 | 1.2 |
| 24 | 0.5 | 0.9 |
| 35 | 0.6 | 0.9 |
| 38 | 0.7 | 1.1 |
| 40 | 0.7 | 1.0 |
| 48 | 0.5 | 1.0 |
| 52 | 0.7 | 1.1 |
| 56 | 0.7 | 1.2 |
| 57 | 0.8 | 1.8 |
| 58 | 0.9 | 1.0 |
| 66 | 0.8 | 1.1 |
| 71 | 0.9 | 0.9 |
| 73 | 0.7 | 1.1 |
| 82 | 0.6 | 1.1 |
| 84 | 0.9 | 1.4 |
| 101 | 0.8 | 1.4 |

TABLE 5-2

| Compound No. | with ear edema inhibition rate of FK506 as 1.0 | |
|---|---|---|
| | TNCB-induced dermatitis | OVA-induced dermatitis |
| 108 | 0.9 | 1.4 |
| 113 | 0.6 | 1.7 |
| 114 | 0.7 | 0.9 |
| 115 | 0.7 | 1.4 |
| 116 | 0.7 | 1.1 |
| 119 | 0.9 | 1.1 |
| 157 | 0.8 | 1.3 |
| 161 | 0.7 | 0.9 |
| 175 | 0.6 | 1.4 |
| 197 | 0.7 | 1.1 |
| 202 | 0.7 | 1.0 |
| 203 | 0.9 | 1.0 |
| 215 | 0.8 | 1.2 |
| 216 | 0.5 | 1.5 |
| 219 | 0.6 | 1.1 |
| 220 | 0.5 | 1.1 |
| FK506 | 1.0 | 1.0 |

As is clear from Tables 5-1 and 5-2, the compound of the present invention shows a clear inhibitory effect against mouse TNCB-induced dermatitis and mouse OVA-induced dermatitis.

Industrial Applicability

The azolylmethylidenehydrazine derivative of the present invention or a salt thereof shows a superior antifungal activity against the pathogenic fungi of deep mycosis and superficial mycosis, and an antifungal agent containing same as an active ingredient is useful for the prophylaxis or treatment of fungi infection of mammals including human.

The azolylmethylidenehydrazine derivative of the present invention or a salt thereof is also useful for the treatment of various inflammations and allergic diseases.

This application is based on Japanese patent application No. 2007-160777, the contents of which are incorporated in full herein by this reference.

The invention claimed is:
1. An azolylmethylidenehydrazine derivative represented by the formula (I)

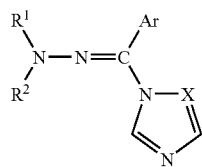

(I)

wherein Ar is an aryl group optionally having 1 to 5 substituents selected from substituent group A or a heteroaryl group selected from the group consisting of pyridyl, pyrimidyl, pyridazinyl, pyrazyl, furyl, thienyl, pyrrolyl, pyrazolyl, oxazolyl, isoxazolyl, thiazolyl, triazolyl, tetrazolyl, indolyl, isoindolyl, quinolizinyl, isoquinolyl, quinolyl, naphthyridyl, quinazolinyl, benzofuranyl, benzothienyl, and benzothiazolyl, wherein the heteroaryl group optionally has 1 to 5 substituents selected from substituent group A, $R^1$ and $R^2$ are the same or different and each is a $C_{1-8}$ alkyl group, a $C_{3-8}$ cycloalkyl group, a $C_{7-15}$ aralkyl group optionally having 1 to 5 substituents selected from substituent group A, an aryl group optionally having 1 to 5 substituents selected from substituent group A, a heteroarylalkyl group optionally having 1 to 5 substituents selected from substituent group A, or $R^1$ and $R^2$ are bonded to each other to form a nitrogen-containing heterocyclic group optionally having 1 to 5 substituents selected from substituent group A, X is CH or a nitrogen atom, substituent group A is a $C_{1-8}$ alkyl group optionally having 1 to 5 substituents selected from substituent group B, a $C_{2-8}$ alkenyl group optionally having 1 to 5 substituents selected from substituent group B, a $C_{3-8}$ cycloalkyl group, a $C_{7-15}$ aralkyl group optionally having 1 to 5 substituents selected from substituent group B, a $C_{1-8}$ alkoxy group optionally having 1 to 5 substituents selected from substituent group B, a $C_{1-8}$ alkylthio group optionally having 1 to 5 substituents selected from substituent group B, an amino group, a mono- or di-($C_{1-8}$ alkyl)amino group optionally having 1 to 5 substituents selected from substituent group B (two alkyls may be the same or different), a $C_{1-8}$ alkylsulfinyl group optionally having 1 to 5 substituents selected from substituent group B, a $C_{1-8}$ alkylsulfonyl group optionally having 1 to 5 substituents selected from substituent group B, a $C_{1-8}$ alkylsulfonylamino group, an acyl group, an acyloxy group, an acylamino group, a $C_{1-8}$ alkoxycarbonyl group, a halogen atom, a hydroxyl group, a carboxyl group, a nitro group, a cyano group, an aryl group optionally having 1 to 5 substituents selected from substituent group B, an aryloxy group optionally having 1 to 5 substituents selected from substituent group B, a heteroaryloxy group, an arylthio group, a $C_{7-15}$ aralkyloxy group optionally having 1 to 5 substituents selected from substituent group B, $C_{2-8}$ alkenyloxy group optionally having 1 to 5 substituents selected from substituent group B, a $C_{2-8}$ alkynyloxy group optionally having 1 to 5 substituents selected from substituent group B, a heterocyclylalkyl group optionally having 1 to 5 substituents selected from substituent group B or a heterocyclylalkyloxy group optionally having 1 to 5 substituents selected from substituent group B, substituent group B is a $C_{1-8}$ alkyl group optionally having 1 to 5 substituents selected from substituent group C, a $C_{1-8}$ alkoxy group optionally having 1 to 5 substituents selected from substituent group C, an amino group, a mono- or di-($C_{1-8}$ alkyl)amino group (two alkyls may be the same or different), an acyloxy group, an acylamino group, a halogen atom, a cyano group, an aryl group optionally having 1 to 5 substituents selected from substituent group C, an aryloxy group optionally having 1 to 5 substituents selected from substituent group C, a $C_{7-15}$ aralkyloxy group, an arylthio group or a heteroaryloxy group, and substituent group C is a halogen atom, a $C_{1-8}$ alkyl group or a $C_{1-8}$ alkoxy group, or a pharmacologically acceptable salt thereof.

2. The azolylmethylidenehydrazine derivative according to claim 1, wherein Ar is a phenyl group optionally having 1 to 5 substituents selected from substituent group A, and $R^1$ and $R^2$ are methyl groups, or a pharmacologically acceptable salt thereof.

3. The azolylmethylidenehydrazine derivative according to claim 1, wherein Ar is 2-ethylphenyl group, 2-ethoxyphenyl group, 2-propoxyphenyl group, 2-isopropoxyphenyl group, 2-butoxyphenyl group, 2-allyloxyphenyl group, 2-propynyloxyphenyl group, 2-(2-phenoxyethoxy)phenyl group, 2-trifluoromethoxyphenyl group, 2-methylthiophenyl group, 2-ethylthiophenyl group, 2-propylthiophenyl group, 2-butylthiophenyl group, 2-phenethylthiophenyl group, 2-(4-methoxybenzyloxy)phenyl group, 2-(4-fluorophenethyloxy)phenyl group, 2-(4-dimethylaminophenethyloxy)phenyl group, 2-[2-(4-methoxyphenoxy)ethoxy]phenyl group or 2-(3-phenoxypropoxy)phenyl group, or a pharmacologically acceptable salt thereof.

4. The azolylmethylidenehydrazine derivative according to claim 1, which is selected from N'-[1-(2-ethylphenyl)-1-imidazol-1-ylmethylidene]-N,N-dimethylhydrazine, N'-[1-(2-ethoxyphenyl)-1-imidazol-1-ylmethylidene]-N,N-dimethylhydrazine, N'-[1-imidazol-1-yl-1-(2-propoxyphenyl)methylidene]-N,N-dimethylhydrazine, N'-[1-imidazol-1-yl-1-(2-isopropoxyphenyl)methylidene]-N,N-dimethylhydrazine, N'-[1-(2-butoxyphenyl)-1-imidazol-1-ylmethylidene]-N,N-dimethylhydrazine, N'-[1-(2-allyloxyphenyl)-1-imidazol-1-ylmethylidene]-N,N-dimethylhydrazine, N'-[1-imidazol-1-yl-1-[2-(2-phenoxyethoxy)phenyl]methylidene]-N,N-dimethylhydrazine, N'-[1-imidazol-1-yl-1-(2-trifluoromethoxyphenyl)methylidene]-N,N-dimethylhydrazine, N'-[1-imidazol-1-yl-1-(2-methylthiophenyl)methylidene]-N,N-dimethylhydrazine, N'-[1-(2-ethylthiophenyl)-1-imidazol-1-ylmethylidene]-N,N-dimethylhydrazine, N'-[1-imidazol-1-yl-1-(2-propylthiophenyl)methylidene]-N,N-dimethylhydrazine, N'-[1-(2-butylthiophenyl)-1-imidazol-1-ylmethylidene]-N,N-dimethylhydrazine, N'-[1-imidazol-1-yl-1-(2-phenethylthiophenyl)methylidene]-N,N-dimethylhydrazine, N'-[1-imidazol-1-yl-1-[2-(4-methoxybenzyloxy)phenyl]methylidene]-N,N-dimethylhydrazine, N'-[1-[2-[2-(4-fluorophenypethoxy]phenyl]-1-imidazol-1-ylmethylidene]-N,N-dimethylhydrazine, N'-[1-imidazol-1-yl-1-[2-(4-dimethylaminophenethyloxy)phenyl]methylidene]-N,N-dimethylhydrazine, N'-[1-imidazol-1-yl-1-[2-[2-(4-methoxyphenoxy)ethoxy]phenyl]methylidene]-N,N-dimethylhydrazine, and N'-[1-imidazol-1-yl-1-[2-(3-phenoxypropoxy)phenyl]methylidene]-N,N-dimethylhydrazine, or a pharmacologically acceptable salt thereof.

5. A medicament comprising (a) the azolylmethylidenehydrazine derivative according to claim 1 or a pharmacologically acceptable salt thereof, and (b) a pharmacologically acceptable carrier.

6. The medicament according to claim 5, which is an antifungal agent.

7. The medicament according to claim 5, which is an anti-inflammatory agent or antiallergic agent.

8. The azolylmethylidenehydrazine derivative according to claim 1 or a pharmacologically acceptable salt thereof for use as an antifungal agent.

9. The azolylmethylidenehydrazine derivative according to claim 1 or a pharmacologically acceptable salt thereof for use as an anti-inflammatory agent or an antiallergic agent.

10. A method for the treatment of mycosis, comprising administering an effective amount of the azolylmethylidenehydrazine derivative according to claim 1 or a pharmacologically acceptable salt thereof to a mammal in need thereof.

11. A method for the treatment of inflammation or allergy, comprising administering an effective amount of the azolylmethylidenehydrazine derivative according to claim 1 or a pharmacologically acceptable salt thereof to a mammal in need thereof.

12. A method for the treatment of mycosis, comprising administering an effective amount of the azolylmethylidenehydrazine derivative according to claim 2 or a pharmacologically acceptable salt thereof to a mammal in need thereof.

13. A method for the treatment of mycosis, comprising administering an effective amount of the azolylmethylidenehydrazine derivative according to claim 3 or a pharmacologically acceptable salt thereof to a mammal in need thereof.

14. A method for the treatment of mycosis, comprising administering an effective amount of the azolylmethylidenehydrazine derivative according to claim 4 or a pharmacologically acceptable salt thereof to a mammal in need thereof.

15. A method for the treatment of inflammation or allergy, comprising administering an effective amount of the azolylmethylidenehydrazine derivative according to claim 2 or a pharmacologically acceptable salt thereof to a mammal in need thereof.

16. A method for the treatment of inflammation or allergy, comprising administering an effective amount of the azolylmethylidenehydrazine derivative according to claim 3 or a pharmacologically acceptable salt thereof to a mammal in need thereof.

17. A method for the treatment of inflammation or allergy, comprising administering an effective amount of the azolylmethylidenehydrazine derivative according to claim 4 or a pharmacologically acceptable salt thereof to a mammal in need thereof.

18. A medicament comprising (a) the azolylmethylidenehydrazine derivative according to claim 2 or a pharmacologically acceptable salt thereof, and (b) a pharmacologically acceptable carrier.

19. A medicament comprising (a) the azolylmethylidenehydrazine derivative according to claim 3 or a pharmacologically acceptable salt thereof, and (b) a pharmacologically acceptable carrier.

20. A medicament comprising (a) the azolylmethylidenehydrazine derivative according to claim 4 or a pharmacologically acceptable salt thereof, and (b) a pharmacologically acceptable carrier.

* * * * *